United States Patent [19]

Edgington et al.

[11] Patent Number: 5,437,864
[45] Date of Patent: Aug. 1, 1995

[54] METHOD OF INHIBITING BLOOD COAGULATION IN EXTRACORPOREAL CIRCULATION BY INHIBITING HUMAN TISSUE FACTOR

[75] Inventors: Thomas S. Edgington, La Jolla, Calif.; Robert W. Colman, Moylan, Pa.; Janos Kappelmayer, Debrecen, Hungary; L. Henry Edmunds, Jr., Bryn Mawr; Alvise Bernabei, Philadelphia, both of Pa.

[73] Assignees: The Scripps Research Institute, La Jolla, Calif.; Trustees of the University of Pennsylvania; Temple University - Of the Commonwealth Systems of Higher Education, both of Phialdelphia, Pa.

[21] Appl. No.: 977,281

[22] Filed: Nov. 16, 1992

Related U.S. Application Data

[63] Continuation-in-part of Ser. No. 165,939, Mar. 9, 1988, Pat. No. 5,223,427, which is a continuation-in-part of Ser. No. 67,103, Jun. 25, 1987, Pat. No. 5,110,730, which is a continuation-in-part of Ser. No. 33,047, Mar. 31, 1987, abandoned.

[51] Int. Cl.$^6$ .................. A61K 39/395; G07K 15/28
[52] U.S. Cl. ........................ 424/145.1; 424/130.1; 424/140.1; 424/141.1; 530/388.23; 530/388.24; 530/388.25; 604/4
[58] Field of Search ............... 530/388.23, 388.24, 530/388.25; 424/85.8, 130.1, 140.1, 141.1, 145.1, 152.1; 604/4

[56] References Cited

PUBLICATIONS

Osterud, B. et al., Biochem. Biophys. Res. Comm. 88:59–67 (May 14, 1979).
Tanaka, H., et al., Thrombosis Res. 40: 745–756 (1985).
Kohler, G., et al., Nature 256: 495–497 (Aug. 7, 1975).
Carson, et al., Monoclonal Antibodies Against Bovine Tissue Factor, Which Block Interaction with Factor VII, Blood, 66:152,156, 1985.
Guha, et al. Affinity Purification of Human Tissue Factor: Interaction of Factor VII and Tissue Factor in Detergent–Micelles, Proc. Natl. Acad. Sci. USA, 83:299–302, 1986, Biochemistry.
Yanina T. Wachtfogel, et al.,; Formation of $Cl_5$–Cl–Inhibitor, Kallikrein . . . Blood; vol. 73, No. 2; Feb., 19889; pp. 468–471.
Janos Kappelmayer, et al.; Upregulation of Mac–1 surface expression . . . Mosby/Journal Page 1 Sep. 11, 1992.
Yanina T. Wachtfogel, et al., Human Neutrophil Degranulation During . . . Blood, vol. 69, No. 1 Jan. 1987 pp. 324–330.
Jacek Musial, et al.; Loss of Fibrinogen Receptors from the Platelet . . . The Journal of Laboratory and Clinical Medicine; vol. 105, No. 4, pp. 514–522.
Robert W. Colman, MD; Platelet and Neutrophil Activation in Cardiopulmonary . . . The Society of Thoracic Surgeons; 1990.
L. H. Edmunds, Jr., et al.; Blood–Surface Interactions During Cardiopulmonary . . . Steinkopff Verlag Darmstadt; 1991; pp. 27–36.

*Primary Examiner*—Christine M. Nucker
*Assistant Examiner*—T. Cunningham
*Attorney, Agent, or Firm*—Spensley Horn Jubas & Lubitz

[57] ABSTRACT

This invention provides a method of inhibiting coagulation in extracorporeal circulation in a subject, comprising administration of a therapeutically effective amount of a monoclonal antibody which inhibits the ability of tissue factor to bind to factor VII/VIIa. The method prevents complex formation between tissue factor and factor VII/VIIa and thus inhibits coagulation of blood in extracorporeal procedures such as cardiopulmonary bypass and other shunt procedures. Anti-tissue factor monoclonal antibodies produced by hybridoma cell lines TFS-5G9 or TF9-6B4 may be used in the claimed methods.

9 Claims, 23 Drawing Sheets

```
              -30         -20         -10
         ME   TPAWPRVPRP  ETAVARTLLL  GWVFAQVAGA 10          20          30          40
SGTTNTVAAY   NLTWKSTNFK  TILEWEPKPV  NQVYTVQIST 50          60          70          80
KSGDWKSKCF   YTTDTECDLT  DEIVKDVKQT  YLARVFSYPA 90         100         110         120
GNVESTGSAG   EPLYENSPEF  TPYLETNLGQ  PTIQSFEQVG 130         140         150         160
TKVNVTVEDE   RTLVRRNNTF  LSLRDVFGKD  LIYTLYYWKS 170         180         190         200
SSSGKKTAKT   NTNEFLIDVD  KGENYCFSVQ  AVIPSRTVNR 210         220         230         240
KSTDSPVECM   GQEKGEFREI  FYIIGAVVFV  VIILVIILAI 250         260
SLHKCRKAGV   GQSWKENSPL  NVS
```

```
                                        M  E  T  P  A  W  P  R  V  P  R  P  E  T  A  V  A  R  T
CGTTCCGCTCGATCTCGCCGCCAACTGGTAGACATGGAGACCCCTGCCTGGCCCCGGGTCCCCGAGACCCCGTCGCTCGGACG
         10        20        30        40        50        60        70        80        90

L  L  L  G  W  V  F  A  Q  V  A  G  A  S  G  T  N  T  V  A  A  Y  N  L  T  W  K  S  T
CTCCTGCTCGGCTGGGTCTTCGCCCAGGTGGCCGGGGCTTCAGGCACTACTACAAATACTGTGGCAGCATATAATTAACTTGGAAATCAACT
        100       110       120       130       140       150       160       170       180

N  F  K  T  I  L  E  W  E  P  K  P  V  N  Q  V  Y  T  V  Q  I  S  T  K  S  G  D  W  K  S
AATTTCAAGACAATTTTGGAGTGGGAACCCAAACCCGTCAATCAAGTCTACACTGTTCAAATAAGCACTAAGTCAGGAGATTGGAAAAGC
        190       200       210       220       230       240       250       260       270

K  C  F  Y  T  D  T  E  C  D  L  T  D  E  I  V  K  D  V  K  Q  T  Y  L  A  R  V  F  S
AAATGCTTTTACACAGACACAGAGTGTGACCTCACCGACGAGATTGTGAAGGATGTGAAGCAGACGTACTACTTGGCACGGGTCTTCTCC
        280       290       300       310       320       330       340       350       360

Y  P  A  G  N  V  E  S  T  G  S  A  G  E  P  L  Y  E  N  S  P  E  F  T  P  Y  L  E  T  N
TACCCGGCAGGGAATGTGGAGAGCACCGGTTCTGCTGGGGAGCCTCTGTATGAGAACTCCCCAGAGTTCACACCTTACCTGGAGACAAAC
        370       380       390       400       410       420       430       440       450

L  G  Q  P  T  I  Q  S  F  E  Q  V  G  T  K  V  N  V  T  V  E  D  E  R  T  L  V  R  R  N
CTGGACAGCCAACAATTCAGAGTTTGAACAGGTGGGAACAAAAGTGACCGTAGAAGATGAACGGACTTTAGTCAGAAGGAAC
        460       470       480       490       500       510       520       530       540
```

FIG.2-2

```
     N  T  F  L  S  L  R  D  V  F  G  K  D  L  I  Y  T  L  Y  Y  W  K  S  S  S  G  K  K  T
     AACACTTCCTAAGCCTCCGGGATGTTTTTGGCAAGGACTTAATTTATACACTTTATTGAATCTTCAAGTTCAGGAAAGAAACA
             550       560       570       580       590       600       610       620       630

A  K  T  N  E  F  L  I  D  V  D  K  G  E  N  Y  C  F  S  V  Q  A  V  I  P  S  R  T
     GCCAAAACAAACACTAATGAGTTTTTGATTGATGTGGATAAAGGAGAAAACTACTGTTTCAGTGTTCAAGCAGTGATTCCCTCCGAACA
             640       650       660       670       680       690       700       710       720

V  N  R  K  S  T  D  S  P  V  E  C  M  G  Q  E  K  G  E  F  R  E  I  F  Y  I  I  G  A  V
     GTTAACCGGAAGAGTACAGACAGCCCGGTAGAGTGTATGGGGCAGGAGAAAGGGGAATTCAGAGAAATATTCTACATCATTGGAGCTGTG
             730       740       750       760       770       780       790       800       810

V  F  V  V  I  I  L  V  I  I  L  A  I  S  L  H  K  C  R  K  A  G  V  G  Q  S  W  K  E  N
     GTATTTGTTGTCATCATCCTTGTCATCATCCTGGCTATATCTCTACACAAGTGTAGAAGGCAGGAGTGGGGCAGAGCTGGAAGGAGAAC
             820       830       840       850       860       870       880       890       900

S  P  L  N  V  S  *
     TCCCCACTGAATGTTTCATAAAGGAAGCACTGTTGGAGCTACTGCACCGAGAACTTTTAAGAGTGCCCTA
             910       920       930       940       950       960       970       980       990

GGACAGAACCCTGTGCCAGAAAAGGAAGTAAAGGAACATGCCAAGAGGCAAGAACAGTGGAAGTCCAGAGGCCAAGAAGAACATGCCAGGATGCAGGTACAGG
             1000      1010      1020      1030      1040      1050      1060      1070      1080

AGGGTGCATAGCCCTGGCCTGAGTGCTGTGTTCTGGAAAGGAGTGG
             1090      1100      1110      1120
```

*p < .05 ent support
METHOD OF INHIBITING BLOOD COAGULATION IN EXTRACORPOREAL CIRCULATION BY INHIBITING HUMAN TISSUE FACTOR This invention was made with Government support under Grant No. PO 1HL16411 awarded by the National Institutes of Health. The Government has certain rights in this invention.

CROSS REFERENCE TO RELATED APPLICATION

This is a continuation-in-part application of Ser. No. 165,939, filed Mar. 9, 1988 now issued as U.S. Pat. No. 5,223,427; which is a continuation-in-part application of Ser. No. 067,103, filed Jun. 25, 1987, now issued as U.S. Pat. No. 5,110,730; which is a continuation-in-part of Ser. No. 033,047, filed Mar. 31, 1987, abandoned.

TECHNICAL FIELD

The present invention relates to a recombinant DNA molecule (rDNAs) carrying a structural gene that encodes the human tissue factor heavy chain protein (huTFh). More specifically, this invention relates to an expression vector capable of expressing huTFh in host cells containing that vector. The present invention also relates to a synthetic polypeptide analog of huTFh and monoclonal antibodies that bind huTFh and the polypeptide analogs.

BACKGROUND OF THE INVENTION

The clotting of blood involves a serial cascade of enzyme, cofactor, proteolytic and gelation reactions mediated by a group of cellular and plasma proteins known as coagulation factors. Initiation of this cascade can occur when the cellular receptor known as tissue factor (TF) binds coagulation factor VII or its derivative, factor VIIa, to form a catalytically active complex. In the absence of TF and without continued binding in a complex, factor VII/VIIa does not initiate coagulation. Thus, the chemical and biological characterization of TF is clearly important to understanding the mechanism of coagulation.

Tissue factor is a membrane-bound glycoprotein that is not normally found soluble in the circulation or accessible to plasma proteins including factor VII/VIIa and the other coagulation factors. While tissue factor is not normally expressed on the surface of cells that form the vasculature, its expression by monocytes within the vasculature can be induced by infectious agent constituents such as bacterial lipopolysaccharide, lymphokines derived from some antigen-stimulated T helper cells, directly by some stimulated T helper cells, and immune complexes. Certain inflammatory mediators of monocyte/macrophage origin, e.g. interlukin 1 and tumor necrosis factor alpha as well as bacterial lipopolysaccharide, can stimulate endothelial cells that line the humoral surface of blood vessels to express TF. Expression of TF in the vascular compartment typically results in disseminated intravascular coagulation or localized initiation of clotting, i.e., thrombogenesis.

Tissue factor is constitutively expressed on the surface of some extravascular cells in in vitro culture including fibroblasts, some as yet unidentified types of brain cells, and certain epithelia that are separated from the circulating plasma proteins by basement membrane barriers. The presence of TF on these cells results in clot formation upon contact with blood as a result of tissue damage. Thus, TF is the foundation upon which the hemostatic system is initiated.

The report of Howell, Am. J. Physiol, 31:1 (1912) was the first to suggest that an isolated tissue protein preparation containing TF could promote coagulation only when present as a phospholipid-protein (lipoprotein) complex. Reconstituting the functional procoagulant activity of TF by relipidating the isolated protein has been necessary because isolation of the TF-containing tissue protein typically results in removal of the phospholipids which are normally associated with the TF protein, such reconstitution has been studied by a number of investigators. For instance, recovery of coagulant activity has been reported to be influenced by the phospholipid type, the ratio of phospholipid to protein, and the detergent and ionic composition of the reconstitution mixture. See Nemerson, J. Clin. Invest., 47–72 (1968); Nemerson, J. Clin. Invest., 48–322 (1969); and Carson et al., Science, 208:307 (1980).

Both isolated and relipidated TF-containing protein preparations have been prepared by extraction from the tissues of various species. Historically, the methods used were difficult, time consuming and resulted in low yields because tissue factor is only present in extremely small quantities in naturally occurring tissues. For a review of the classical methods, see Nemerson et al., Prog. Hem. Thromb., 6:237–261 (1982).

More recently, Broze et al., J. Biol. Chem., 260:10917-20 (1985), Bom et al., Thromb. Res., 42:635–643 (1986) and Guha et al., Proc. Natl. Acad. Sci, USA, 83:299–302 (1986) have reported isolating human tissue factor (huTF) protein using a method based on the discovery that delipidated tissue factor protein can bind factor VII/VIIa when the protein is solubilized in an aqueous solution containing a non-ionic detergent and $CaCl_2$. However, the utility of that method, which employs a factor VII/VIIa affinity sorbent, as a means for isolating tissue factor protein is limited not only by the difficulty in obtaining significant quantities of isolated factor VII/VIIa but also by the lability of factor VII/VIIa.

Broze et al., supra, have suggested that the development of monoclonal antibodies specific for huTF and their use as immunoaffinity sorbents could circumvent problems caused by the limited availability of factor VII/VIIa. However, no anti-huTF monoclonal antibodies have been reported in the literature. Furthermore, two monoclonal antibodies raised against bovine TF [Carson et al., Blood, 662-156 (1985)] do not immunoreact with huTF (Guha et al., supra).

BRIEF SUMMARY OF THE INVENTION

In one embodiment, the present invention contemplates a DNA segment comprising no more than about 12,000 nucleotide base pairs including a sequence defining a structural gene coding for a human tissue factor heavy chain (huTFh) protein. Preferably the structural gene codes for a protein having an amino acid residue sequence represented by FIG. 1 from about residue 1 to about residue 263. More preferably, the structural gene has a nucleotide base sequence represented by FIG. 2 from about base 130 to about base 918.

In preferred embodiments, the DNA segment also includes a second sequence contiguous with the 5' terminus of the first sequence and coding for an amino acid residue leader sequence attached to the amino-terminus of the huTFh protein. The first and second DNA sequences together define a composite structural gene coding for a human tissue factor heavy chain precursor (pre-huTFh) protein. Preferably the composite structural gene codes for a protein having an amino acid residue sequence represented by FIG. 1 from about residue −32 to about residue 263. More preferably the composite structural gene has a nucleotide base sequence represented by FIG. 2 from about base 34 to about base 918.

In another embodiment, the present invention contemplates recombinant DNA molecule comprising a vector operatively linked to a first DNA segment that defines a structural gene coding for a human tissue factor heavy chain protein. Preferably, the recombinant DNA molecule further includes a second DNA segment contiguous with the 5' terminus of first segment and coding for an amino acid residue leader sequence attached to said protein; said first and second DNA segments together defining a composite structural gene that codes for a precursor form of said protein.

In another embodiment, the present invention contemplates human tissue factor binding site polypeptide analog comprising no more than about 50 amino acid residues and including an amino acid residue sequence that corresponds to a sequence represented by the formula:

-VNQVYT-.

More preferably, the present invention contemplates human tissue factor binding site polypeptide analog comprising no more than about 50 amino acid residues and including an amino acid residue sequence that corresponds to a sequence represented by a formula selected from the group consisting of:

-VNQVYTVQIST-, and

-LYYWKSSSSGKKT-.

A further embodiment of the present invention is an antibody composition comprising antibody molecules that:
a) immunoreact with human tissue factor heavy chain protein;
b) immunoreact with a polypeptide represented by a formula selected from the group consisting of:

H-EWEPKPVNQVYT-OH,

H-EPKPVNQVYTVQISTKSGDWKSKC-OH,

H-VFGKDLIYTLYYWKSSSSGKKT-OH,

H-RDVFGKDLIYTLYYWK-OH

H-IYTLYYWKSSSSGKKTAK-OH,

H-SSSGKKTAKTNTNEFLIDVD-KGENYCFSV-OH,

H-SGTTNTVAAYNLTWKSTNFK-TILEWEPKPV-OH,

H-TKSGDWKSKCFYTTDTECDLT-DEIVKDVKQTY-OH,

H-KSGDWKSKC-OH,

H-ECDLTDEIVKDVKQTY-OH,

H-LARVFSYPAGNVESTGSAGEPLYEN-SPEFTPYLC-OH,

H-YENSPEFTPYLETNLGQPTIQS-FEQVGTKV-OH, and

H-QAVIPSRTVNRKSTDSPVEC-OH; and c) do not substantially immunoreact with a polypeptide represented by the formula shown in FIG. 1 from position 204 to position 226.

Also contemplated by the present invention are the hybridomas TF8-5G9, TF9-10H10, TF9-5B7 and TF9-6B4, as well as monoclonal antibody compositions comprising antibody molecules produced by those hybridomas.

The present invention also contemplates a method of assaying for the presence of human tissue factor heavy chain protein in a body fluid sample comprising the steps of:
a) admixing a body sample with antibodies that immunoreact with human tissue factor heavy chain protein to form an immunoreaction admixture;
b) maintaining the admixture for a time period sufficient for the antibodies to immunoreact with any human tissue factor present in the sample and form an immunoreaction product; and
c) detecting the presence of any immunoreaction product formed in step b.

Also contemplated is a method of detecting a thrombus in vivo comprising the steps of:
a) intravenously administering to a human subject a monoclonal antibody composition comprising a physiologically tolerable diluent and an amount of antibody molecules produced by hybridoma TF9-10H10 linked to an in vivo indicating means effective to immunoreact with human tissue factor present in a thrombus;
b) maintaining the administered subject for a predetermined time period sufficient for the antibody molecules to immunoreact with tissue factor present in vivo as part of a thrombus and form an immunoreaction product; and
c) assaying for the presence of any immunoreaction product formed in step (b).

Further contemplated is a method of neutralizing the ability of human tissue factor to bind coagulation factor VII/VIIa in vivo comprising intravenously administering to a human subject a monoclonal antibody composition comprising a physiologically tolerable diluent containing an amount of antibody molecules produced by a hybridoma selected from the group consisting of: TF8-5G9 and TF9-6B4 effective to bind to human tissue factor present.

The present invention also contemplates a method of inhibiting the binding of human tissue factor to coagulation factor VII/VIIa in vivo comprising intravenously administering to a human subject a polypeptide composition comprising a physiologically tolerable diluent containing a polypeptide selected from the group consisting of:

H-EWEPKPVNQVYT-OH,

H-EPKPVNQVYTVQISTKSGDWKSKC-OH,

H-VFGKDLIYTLYYWKSSSSGKKT-OH,

H-RDVFGKDLIYTLYYWK-OH

H-IYTLYYWKSSSSGKKTAK-OH, and

H-SSSGKKTAKTNTNEFLIDVD-
KGENYCFSV-OH;

said polypeptide present in said composition in an amount effective to react with factor VII/VIIa.

In another embodiment the present invention contemplates a diagnostic system in kit form for assaying for the presence of human tissue factor heavy chain protein in sample comprising a package containing an antibody composition of this invention. Preferably, the antibody composition comprises monoclonal antibody molecules produced by a hybridoma selected from the group of hybridomas consisting of:
 a) TF8-5G9,
 b) TF9-6B4,
 c) TF9-10H10 and
 d) TF9-5B7.

A method of isolating blood coagulation factor VII/VIIa from a sample is also contemplated. The method comprises the steps of:
 a) admixing the sample with a solid support comprising a polypeptide of the invention affixed to a solid matrix, said admixing forming a binding reaction admixture;
 b) maintaining said binding reaction admixture for a time period sufficient for said coagulation factor to bind to said polypeptide and form a solid phase complex and a supernatant;
 c) separating said supernatant from said complex; and
 d) recovering said coagulation factor from the separated complex of step c.

Further contemplated is a composition comprising an aqueous solution of biologically active human tissue factor heavy chain protein substantially free of human tissue factor light chain protein. Preferably the biologically active human tissue factor heavy chain protein is dispersed in a phospholipid or a non-ionic detergent.

A diagnostic system in kit form for assaying for coagulation competence in a vascular system fluid sample is also contemplated. It includes a package containing a composition an aqueous solution of biologically active human tissue factor heavy chain protein substantially free of human tissue factor light chains protein wherein said heavy chain protein is present in an amount sufficient to perform at least one assay. Preferably, the heavy chain protein is dispersed in a phospholipid.

In another embodiment a method of preparing mature human tissue factor heavy chain protein and the protein expression product of that method are contemplated. The method includes the steps of:
 a) initiating a culture, in a nutrient medium, of mammalian cells transformed with a recombinant DNA molecule comprising an expression vector compatible with said cells operatively linked to a first DNA segment that defines a structural gene coding for a human tissue factor heavy chain protein and a second DNA segment contiguous with said first segment and coding for an amino acid residue leader sequence attached to said protein; said first and second DNA segments together defining a composite structural gene that codes for a precursor form of said protein;
 b) maintaining said culture for a time period sufficient for said cells to express protein from said recombinant DNA molecule and form said mature protein; and
 c) recovering said mature protein from said culture.

In another embodiment, the invention provides a method of inhibiting coagulation in extracorporeal circulation in a subject, comprising administering to the subject an effective amount of a monoclonal antibody which inhibits the ability of tissue factor to bind factor VII/VIIa.

BRIEF SUMMARY OF THE DRAWINGS

In the drawings forming a portion of this disclosure:

FIG. 1 illustrates the complete amino acid residue sequence of the mature and precursor forms of human tissue factor heavy chain proteins (huTFh and pre-huTFh, respectively), shown from left to right and in the direction from amino-terminus to carboxy-terminus using the single letter amino acid residue code. The amino acid residue sequence of the predominant naturally occurring mature protein form is numbered 1 to 263. The sequence of the lesser found mature form begins at amino acid residue number 3 and ends at residue 263.

The amino acid residue sequence corresponding to the leader sequence (precursor portion) of the pre-huTFh protein that is removed during the maturation process is designated by negative numbers. The extracellular domain and transmembrane anchor region correspond to residue positions 1 to 219 and 220 to 242, respectively.

FIG. 2 is a two-page illustration of the nucleotide sequence of a cDNA that codes for the pre-huTFh and huTFh proteins, shown from left to right and in the direction of 5' terminus to 3' terminus using the single letter nucleotide base code.

FIG. 2-1 illustrates the sequence of nucleotides 1-540.

FIG. 2-2 illustrates the sequence of nucleotides 541-1125.

The structural gene for huTFh begins at base 130 in FIG. 2-1 and ends at base 918 in FIG. 2-2.

The reading frame is indicated by placement of the deduced amino acid residue sequence above the nucleotide sequence such that the single letter that represents each amino acid residue is located above the middle base in the corresponding codon.

Figure 3:
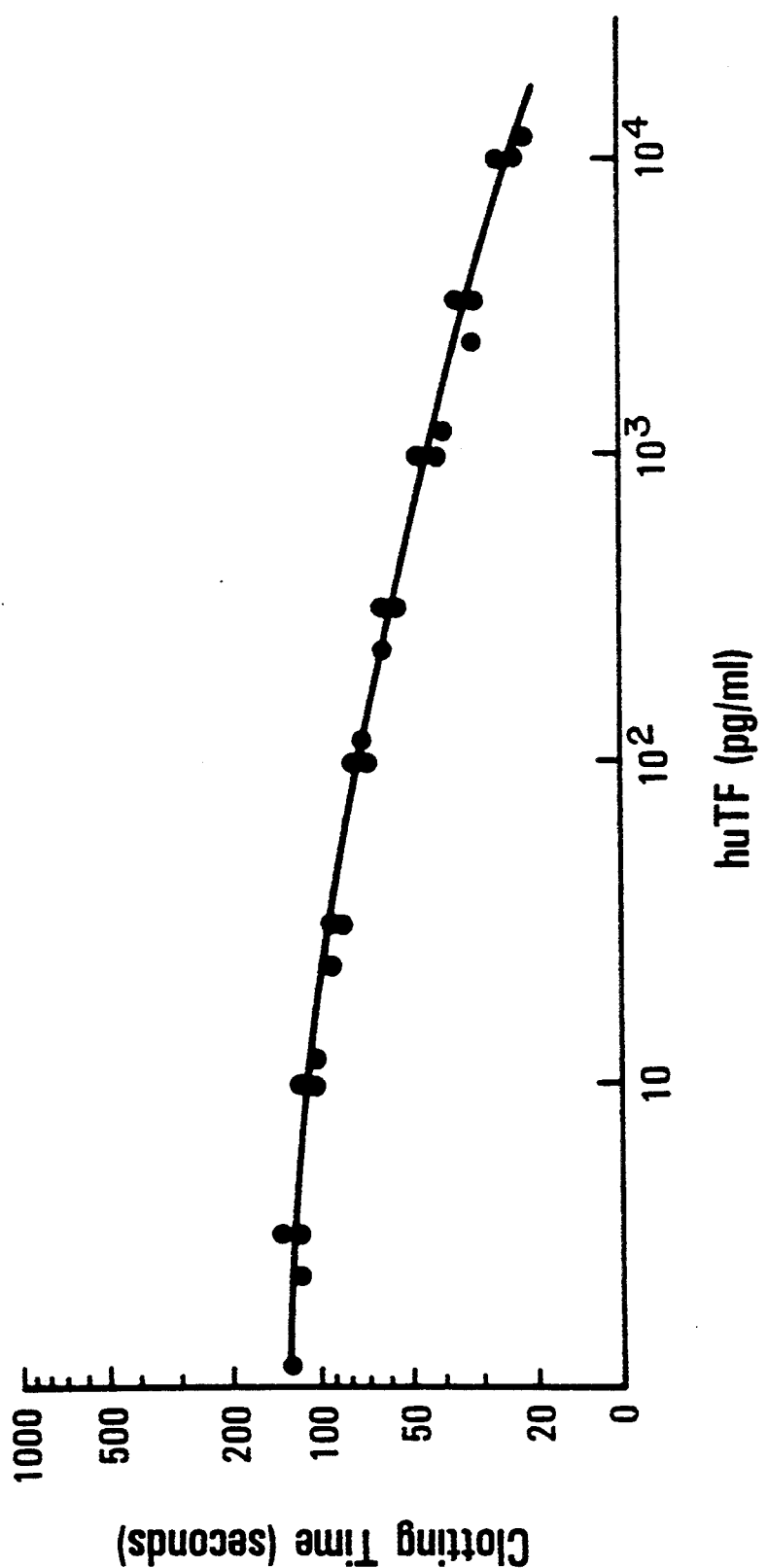

FIG. 3 is a graph illustrating the coagulation assay used to measure huTF procoagulant activity as described in Example 2. A log-log plot is shown of human citrated plasma coagulation (clotting) time in seconds versus the human tissue factor (huTF) concentration in picograms per milliliter (pg/ml).

Figure 4:
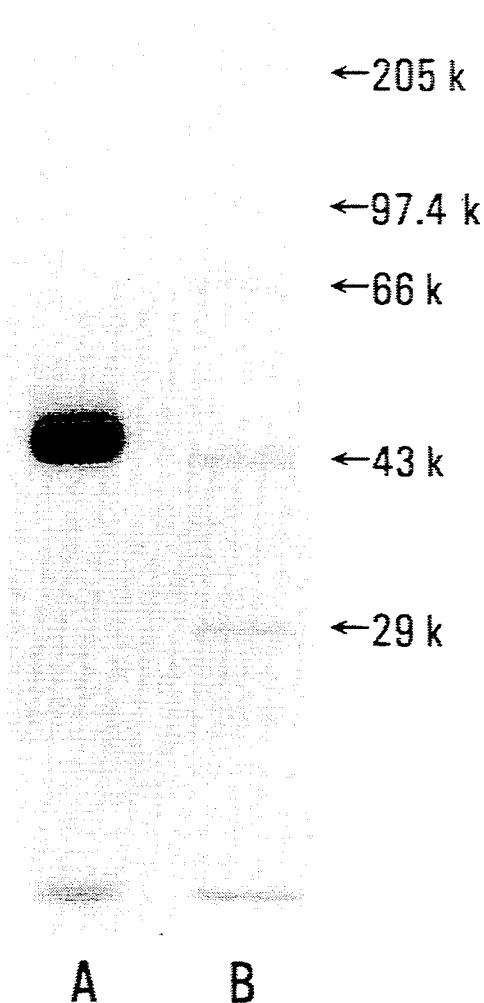

FIG. 4 illustrates an autofluorogram of factor VII/VIIa affinity-isolated huTF electrophoresed in a 10% polyacrylamide gel. Lane A shows $^{125}$I-labeled huTF that was isolated and reduced with dithiothreitol (DTT) prior to electrophoresis as described in Example 4. Lane B shows molecular-weight standards with apparent molecular weights indicated in kilodaltons (k).

Figure 5:
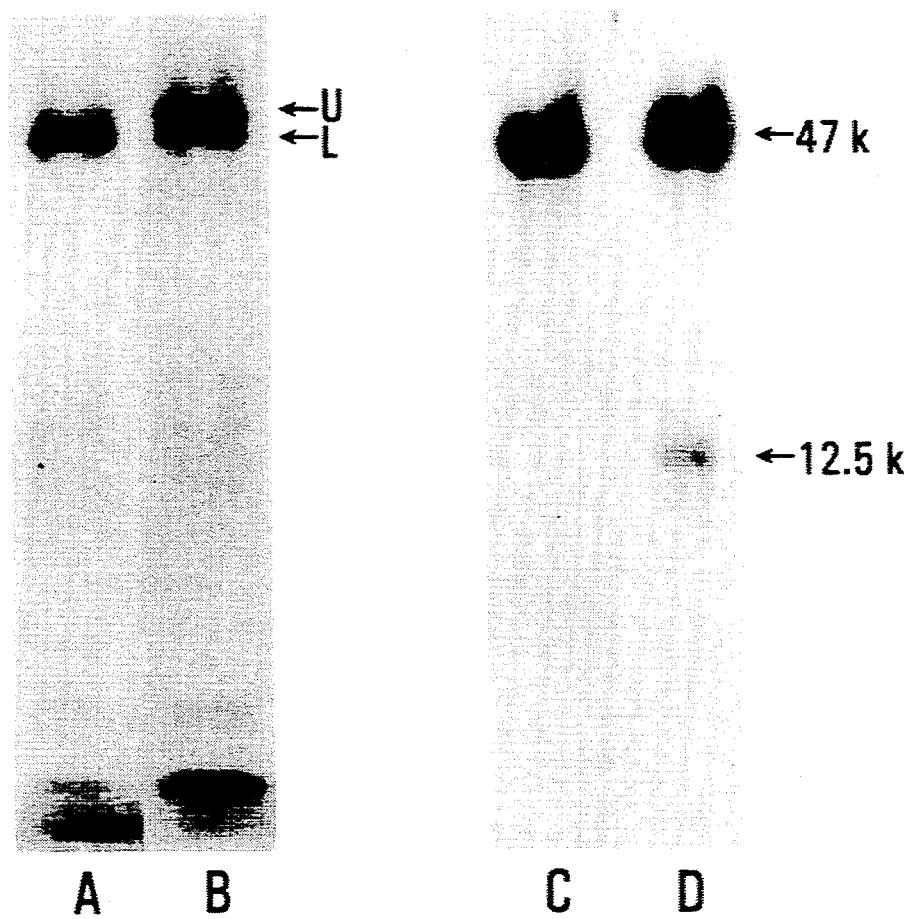

FIG. 5 illustrates an autofluorogram of factor VII/VIIa affinity-isolated huTF electrophoresed in 15% polyacrylamide gels. Isolation, labeling with $^{125}$I and electrophoresis of huTF were done as described in Example 4. Lane A shows the isolated huTF after reduction with DTT. Lane B shows the same sample electrophoresed without reduction with DTT. The upper and lower bands (labeled U and L) correspond to the approximately 58 and 47 k size forms of huTF. After autofluorography, the upper and lower bands were excised, rehydrated in SDS sample buffer containing DTT, inserted into the sample well of a second 15% polyacrylamide gel and subjected to electrophoresis. Lane C shows the re-electrophoresis of the lower band obtained from Lane B. Lane D shows the re-electrophoresis of the upper band obtained from Lane B. The 12.5 and 47 kilodalton (k) apparent molecular weight proteins are indicated by the arrows.

FIG. 6A illustrates an autofluorogram of factor VII/-VIIa affinity-isolated $^{125}$I-labeled huTF that was first immunoprecipitated with the huTF-specific monoclonal antibody TF8-5G9 and then electrophoresed with reduction by DTT in an 8 to 17% polyacrylamide gradient gel as described in Example 4.

FIG. 6B illustrates an autofluorogram of factor VII/-VIIa affinity-isolated $^{125}$I-labeled huTF that was first immunoprecipitated with the huTF-specific monoclonal antibody TF8-5G9 and then electrophoresed without reduction in an 8 to 17% polyacrylamide gradient gel as described in Example 4.

Figure 7:
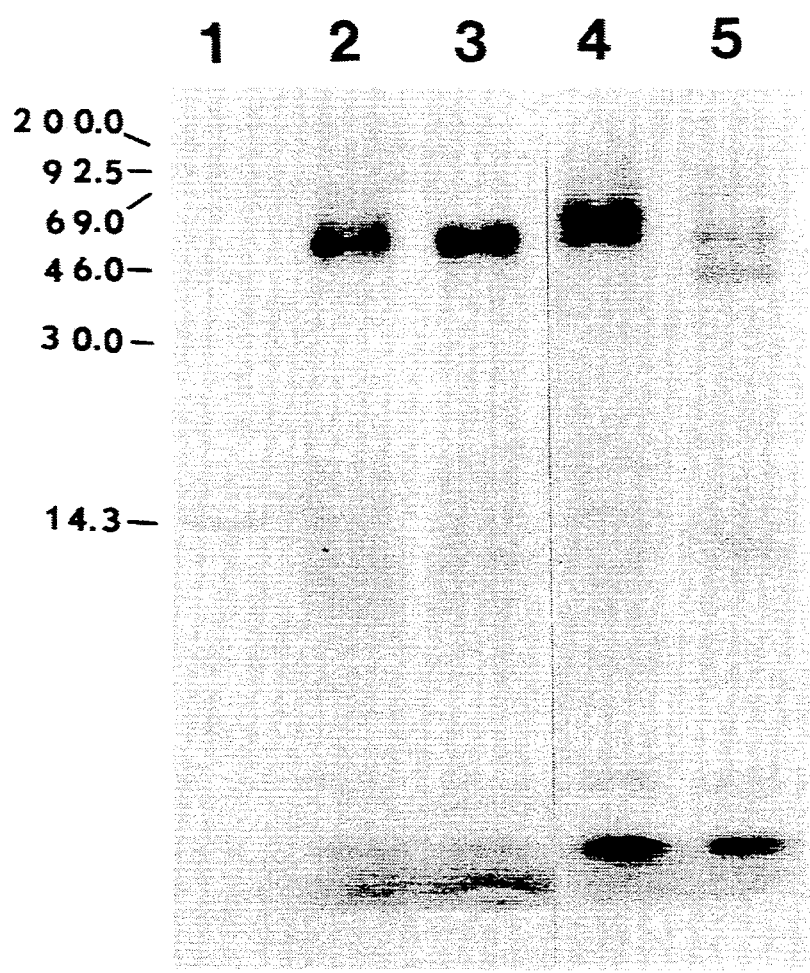

FIG. 7 illustrates an autofluorogram of factor VII/-VIIa affinity-isolated huTF electrophoresed in 15% polyacrylamide gels. Isolation, labeling with $^{125}$I, reduction and deglycosylation were conducted as described in Example 4. Lane 1 contains the following protein standards electrophoresed as markers with apparent molecular weights (Mr) indicated in kilodaltons; lysozyme, 14.3; carbonic anhydrase, 30.0; ovalbumin, 46.0; bovine serum albumin, 69.0; phosphorylase b, 92.5; and myosin, 200.0, all obtained from Amersham, Arlington Heights, Ill. $^{125}$I-huTF-containing samples were electrophoresed either with DTT (Lanes 2 and 3) or without DTT (Lanes 4 and 5). Some of these $^{125}$I-huTF-containing samples were deglycosylated (Lanes 3 and 5) while others were not deglycosylated (Lanes 2 and 4) before electrophoresis.

The $^{125}$I-huTF-containing samples run in Lanes 3 and 5 were deglycosylated prior to electrophoresis while those in Lanes 2 and 4 were not.

Figure 8:
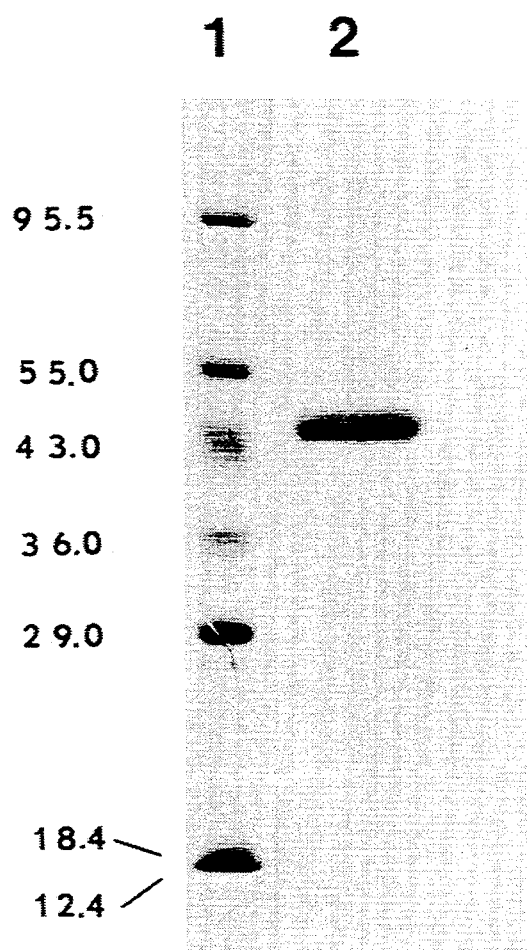

FIG. 8 illustrates an autofluorogram of immunoaffinity-isolated huTF electrophoresed in 10% polyacrylamide gels as described in Example 9. Lane 1 contains the following protein standards electrophoresed as markers with apparent molecular weights (Mr) indicated in kilodaltons; cytochrome c, 12.4; lactoglobulin, 18.4; carbonic anhydrase, 29.0; lactate dehydrogenase, 36.0; ovalbumin, 43.0; glutamate dehydrogenase, 55.0; and phosphorylase b, 95.5, all obtained from Diversified Biotech (Newton Centre, Mass.).

Lane 2 contains about 20 ug of protein, determined using the BCA protein assay method of Smith et al., *Anal. Bioch.*, 150:76–85 (1985), and reduced using DTT. huTF heavy chain (huTFh) is clearly visible at approximately 47 Mr and huTF light chain is faintly visible at approximately 12.5 Mr. Protein was visualized by Coomassie blue staining as described by Laemmli, *Nature*, 227:680–685 (1970).

Figure 9:
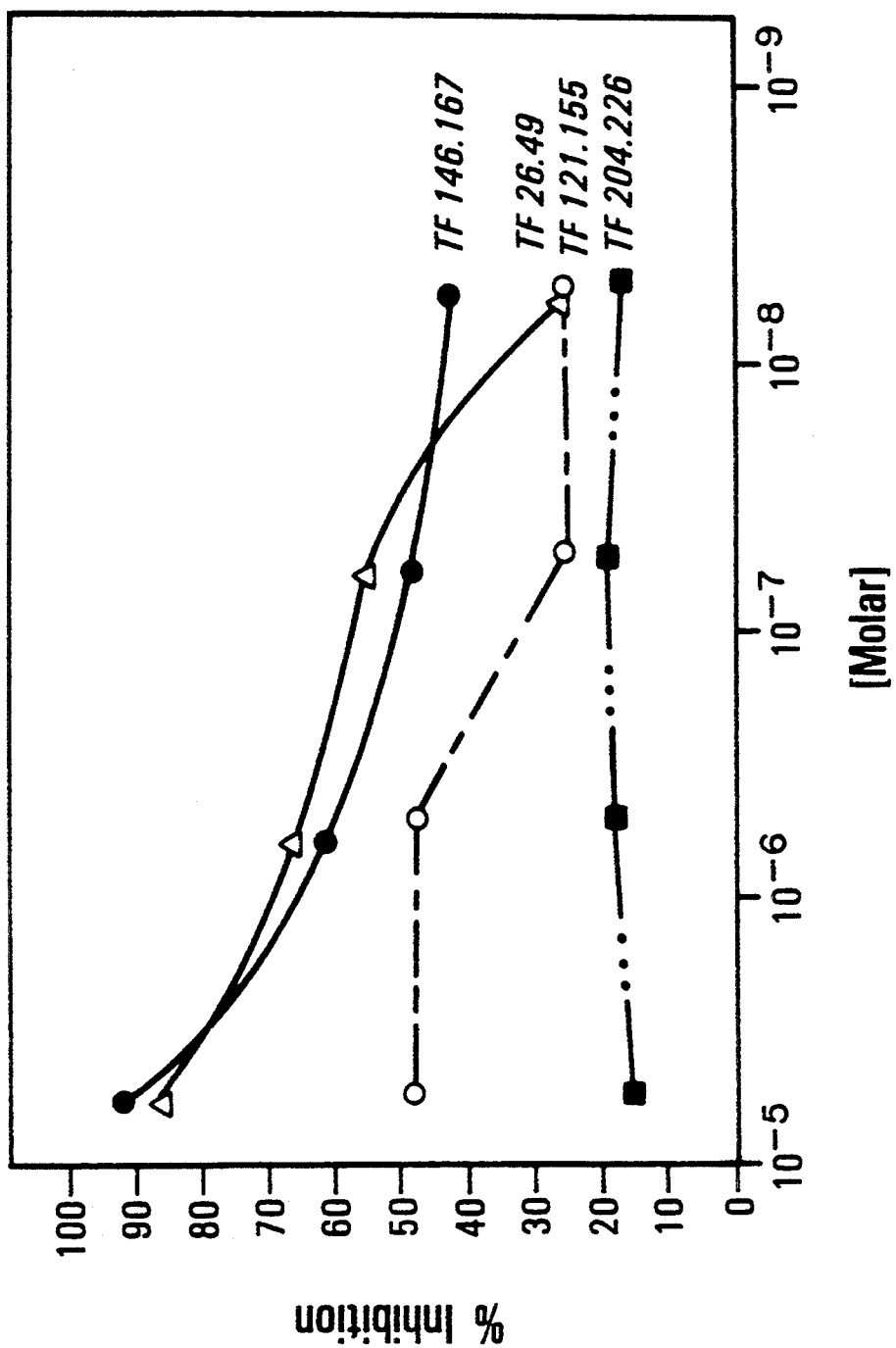

FIG. 9 is a graph illustrating the dose-response curve of inhibition of huTF-initiated coagulation by non-phospholipidated (non-lipidated) polypeptide analogs of huTFh. Percent inhibition of coagulation by various concentrations of non-lipidated polypeptides was measured as described in Example 12. Polypeptides tested include p26-49 (Δ,TF26.49), p121-155 (◯, TF121.155), p146-167 (■, TF146.167) and p204-226 (●,TF204.226).

Figure 10:
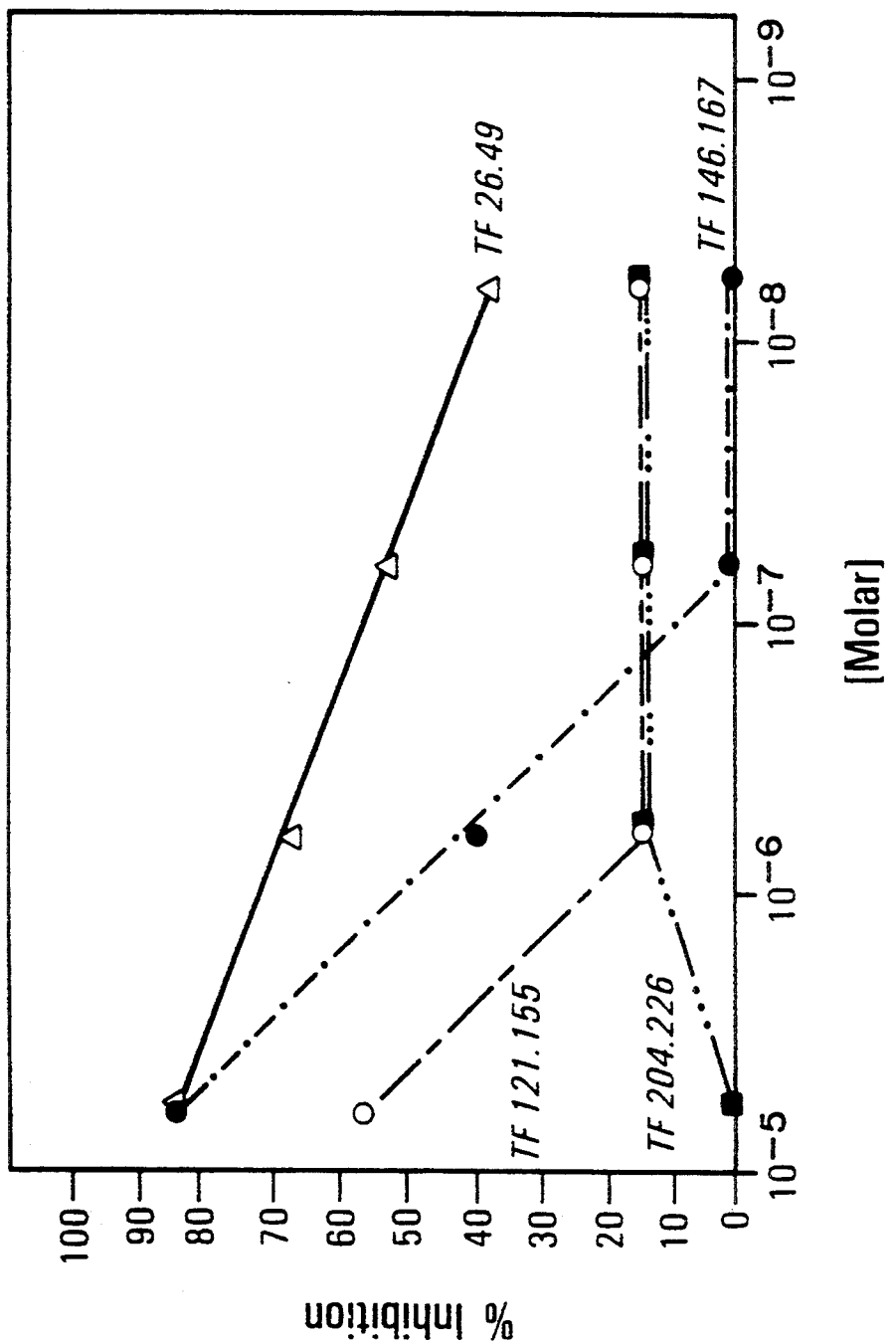

FIG. 10 is a graph illustrating the dose-response curve of inhibition of huTF-initiated coagulation by phospholipidated (lipidated) polypeptide analogs of huTFh. Percent inhibitions were measured by the same methods and for the same analogs as described in FIG. 9.

Figure 11:
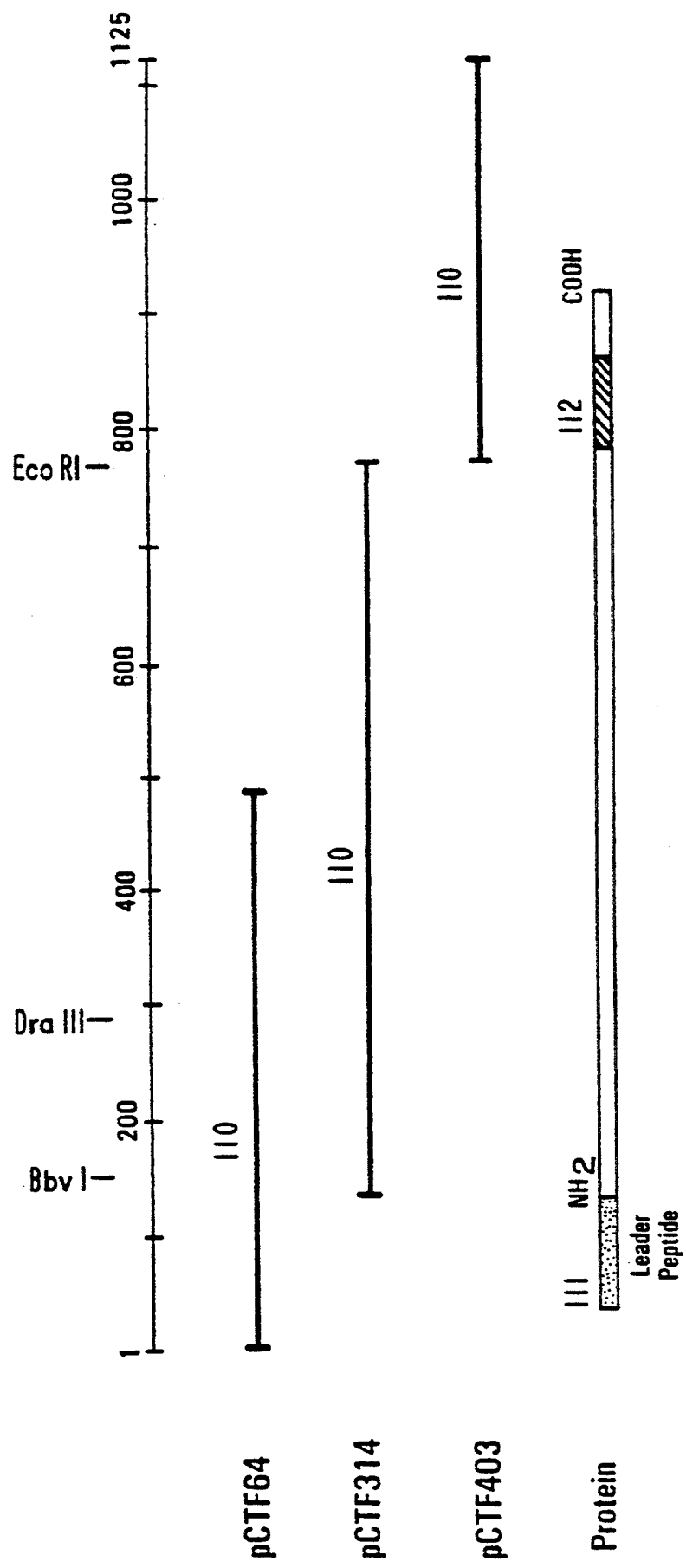

FIG. 11 illustrates the restriction maps of the EcoRI segment inserts within the recombinant DNA plasmids pCTF64, pCTF314 and pCTF403. The inserts (110) represent overlapping portions of nucleotide sequences that together correspond to the complete nucleotide sequence of the pre-huTFh gene. Individually, the inserts include nucleotide residues that correspond from left to right and in the direction of 5' to 3' to the nucleotide sequence shown in FIG. 2 from base residues 1–486 (contained in pCTF64), residues 135–775 (contained in pCTF314) and residues 776–1125 (contained in pCTF403). Also shown is the approximate location of restriction endonuclease cleavage sites within the inserts that were used in constructing the various recombinant DNA molecules described in Example 16. Further indicated is the approximate location of the corresponding pre-huTFh protein with its leader peptide (111) and transmembrane anchor domain (112) shown intact.

Figure 12:
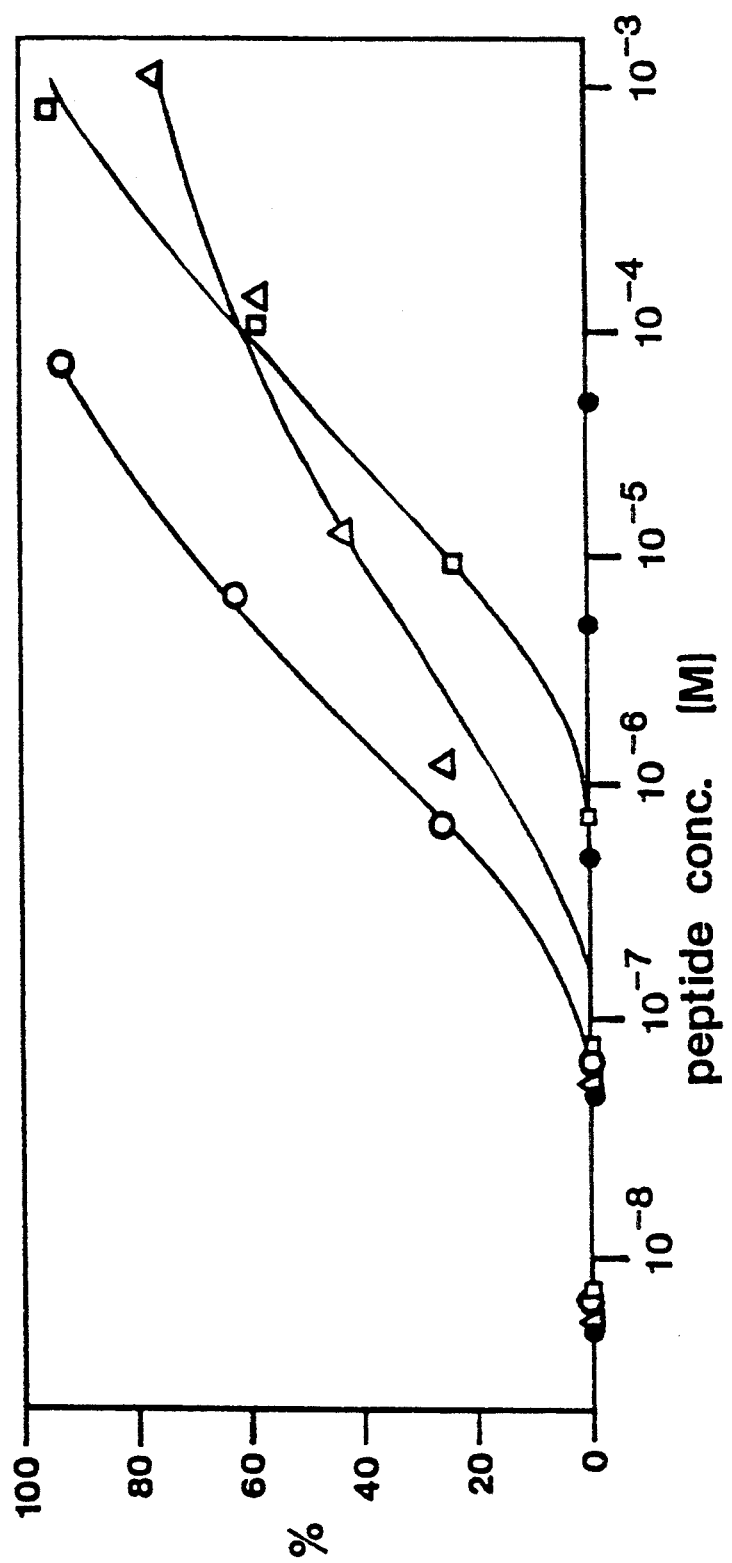

FIG. 12 is a graph illustrating the dose-response curve of inhibition of huTF-initiated coagulation by non-phospholipidated (non-lipidated) polypeptide analogs of huTFh. Percent inhibition (%) of coagulation by various concentrations expressed in molarity (M) of non-lipidated polypeptides was measured as described in Example 17. Polypeptides examined include p24-35 (Δ), p26-49 (◯), p152-169 (☐) and the peptides, p40-71, p72-104, p94-123 and p161-189 which all produced no substantial inhibition and are collectively indicated by the closed circles (◯).

Figure 13:
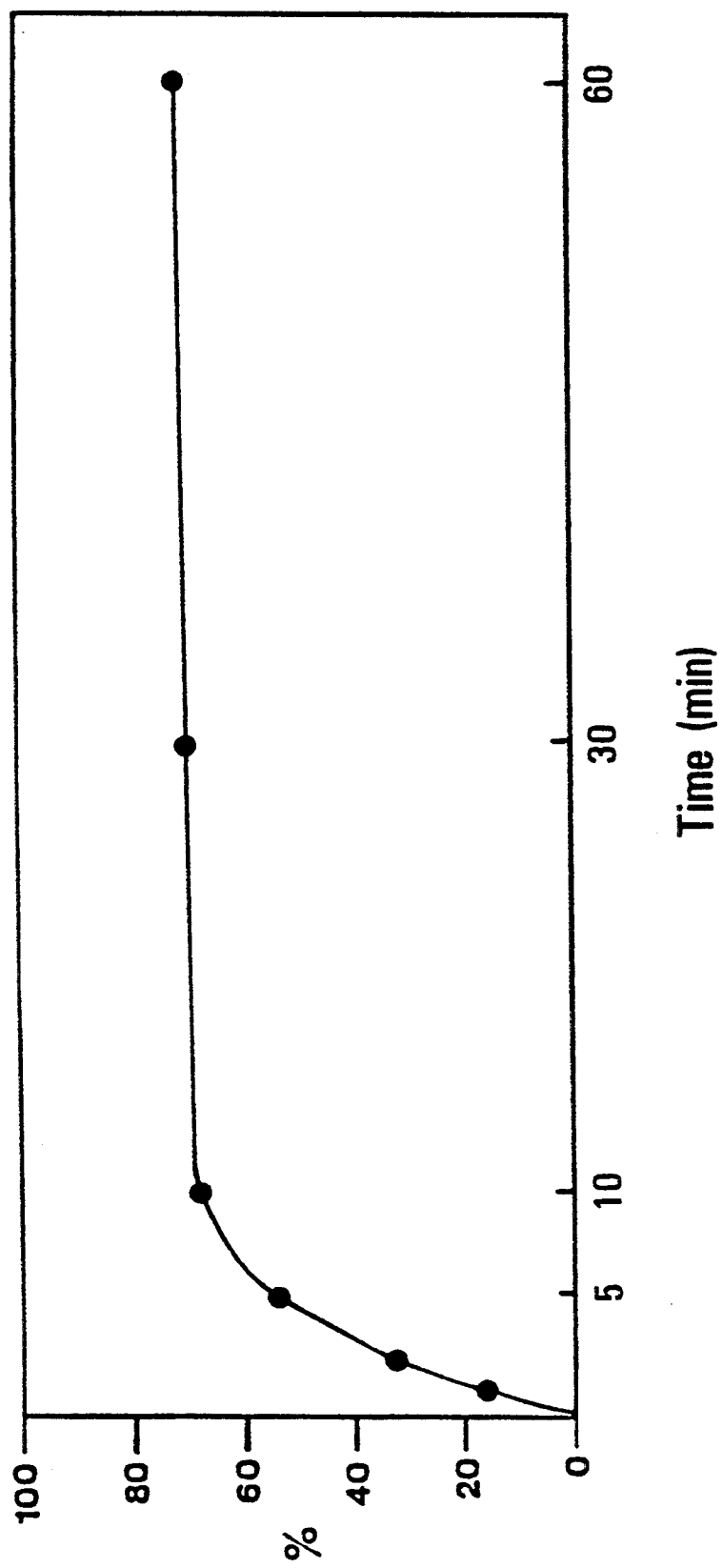

FIG. 13 is a graph illustrating the kinetics of inhibition of coagulation by a TF8-5G9 antibody composition. Percent inhibition (%) of coagulation is plotted over various antibody immunoreaction times measured as described in Example 18.

Figure 14:
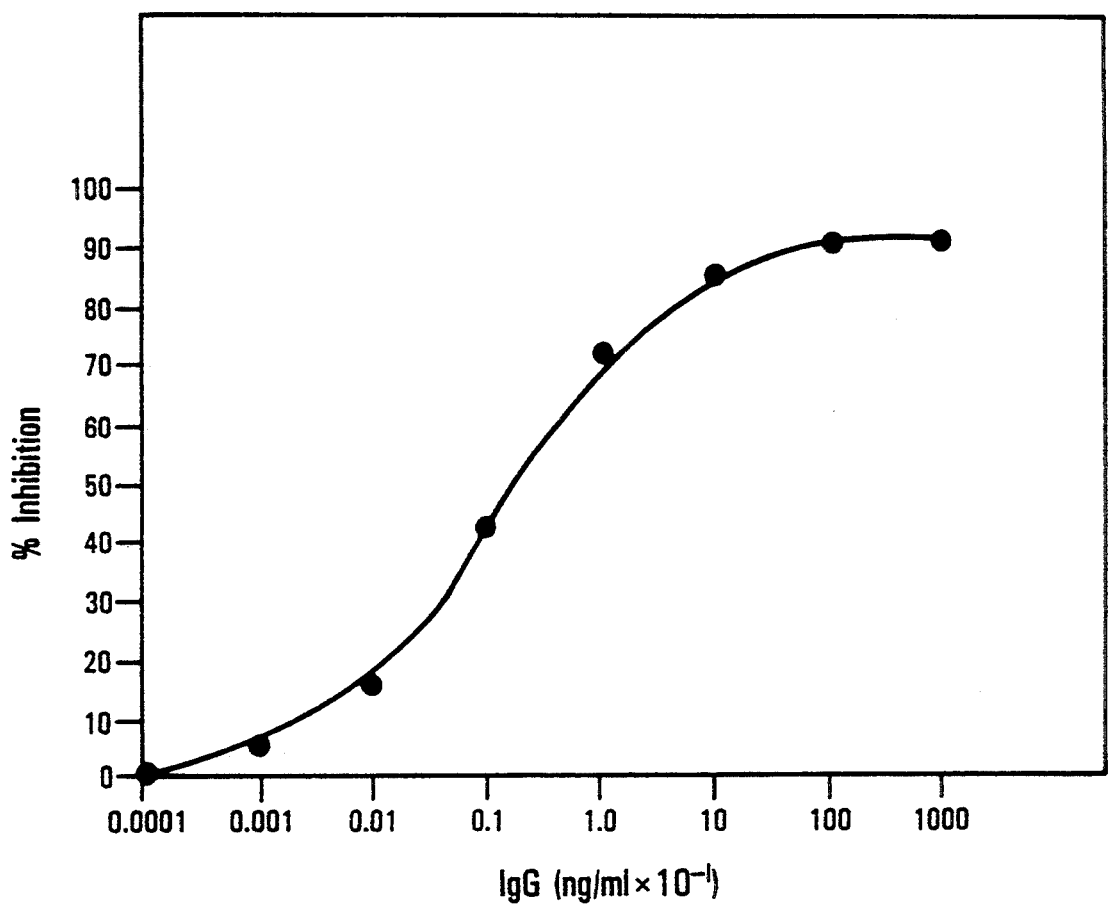

FIG. 14 is a graph illustrating the dose response of inhibition of huTF-initiated coagulation by anti-huTF antibodies. Percent (%) inhibition of coagulation by various concentrations of the anti-huTF monoclonal antibody TF8-5G9 was measured as described in Example 19.

Figure 15:
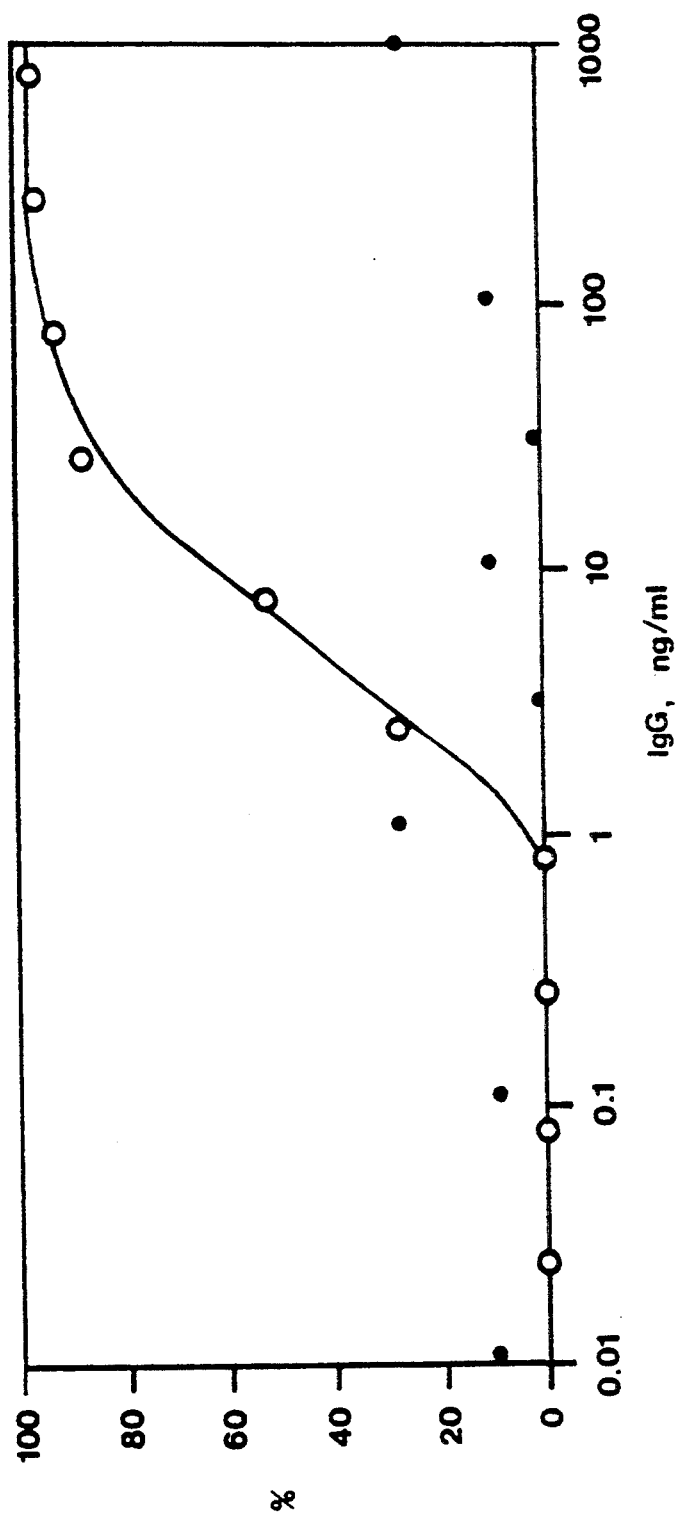

FIG. 15 is a graph illustrating the dose-response of inhibition of huTF-initiated coagulation by anti-huTF antibodies where the source of huTF is a human cell lysate of the fibroblast cell line GM1381. Percent inhibition (%) of coagulation by various concentrations of the anti-huTF monoclonal antibody TF8-5G9 was measured as described in Example 19. Open circles (0) designate TF8-5G9 antibody and closed circles (0) designate an irrelevant antibody.

Figure 16:
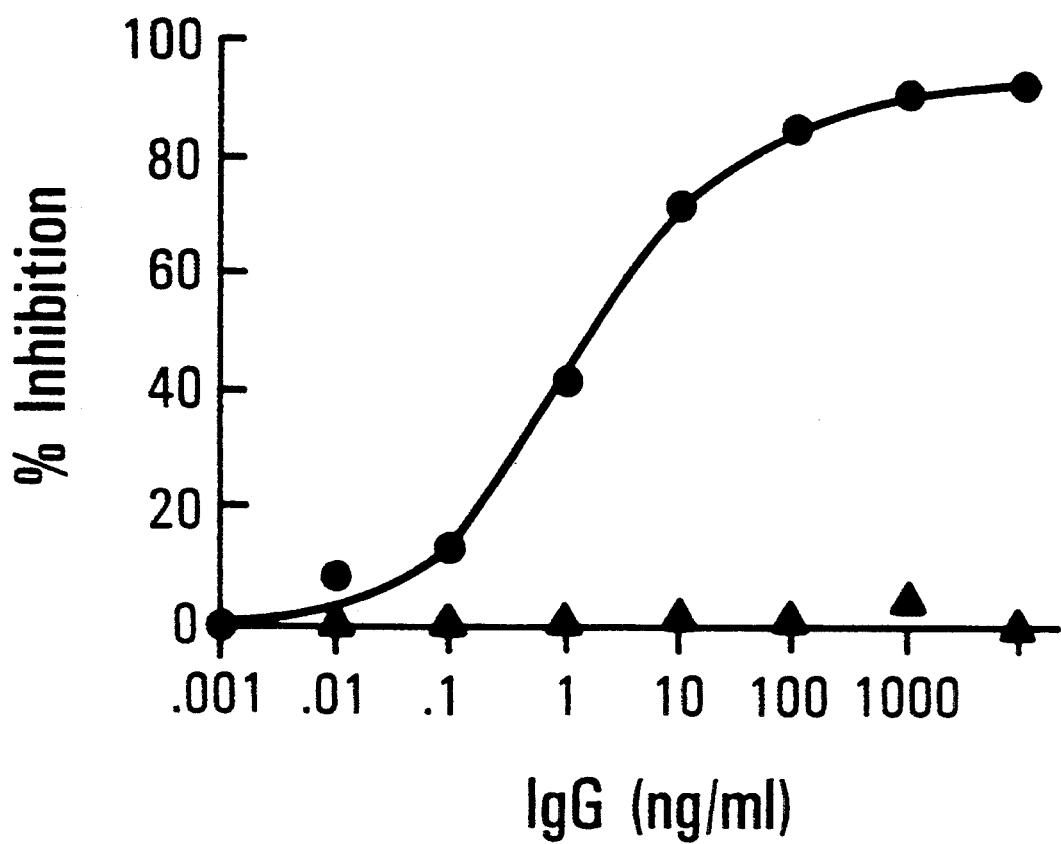

FIG. 16 illustrates inhibition of the procoagulant activity of purified human brain TF by anti-TF monoclonal antibody TF8-5G9. The clotting activity of purified human brain TF reconstituted into phospholipid vesicles was determined after preincubation for 30 minutes at 37° C. with varying concentrations of purified IgG. Circles are for the anti-TF antibody TF8-5G9; triangles are for the irrelevant control antibody PAb100. Data are expressed as percent inhibition relative to the activity observed in the absence of added antibody.

Figure 17A:
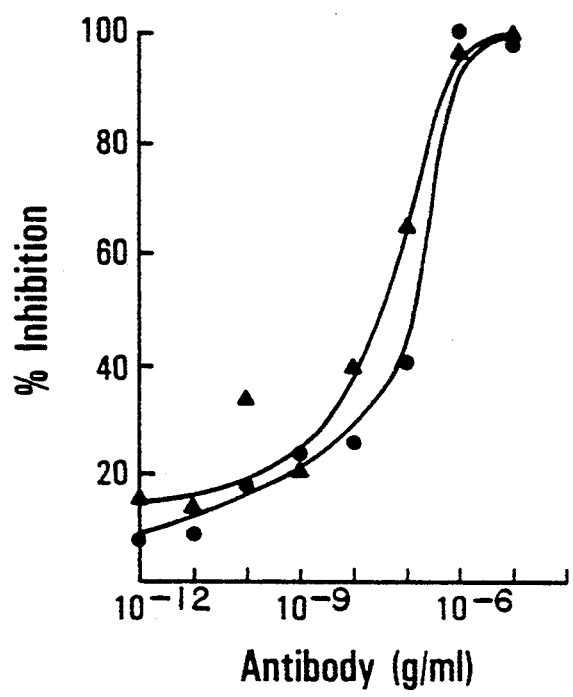
Figure 17B:
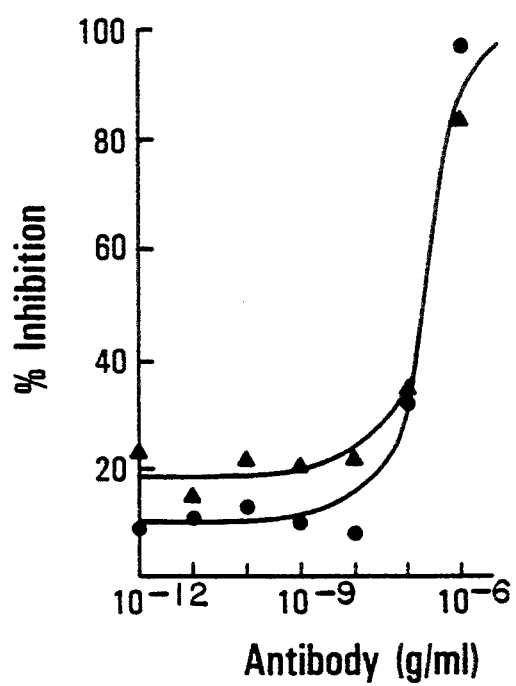

FIG. 17 illustrates inhibition factor VII binding to, and factor Xa formation by, cultured J82 bladder carcinoma cells treated with purified anti-TF monoclonal antibodies. Values for the inhibition of the rate of factor Xa formation are represented by triangles; values for the inhibition of factor VII binding are represented by circles. Data are expressed as percent inhibition relative to the values obtained for cells incubated without added antibody. Panel A, effect of antibody TF9-2C4; panel B, effect of antibody TF9-5B7.

Figure 18A:
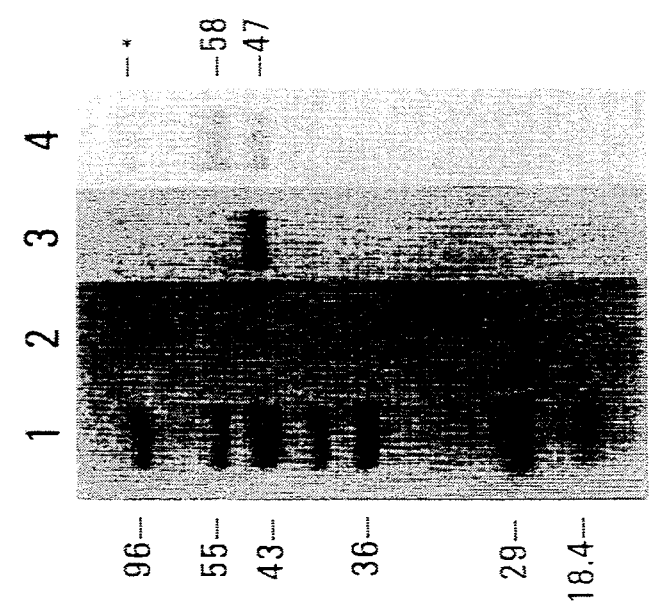
Figure 18B:
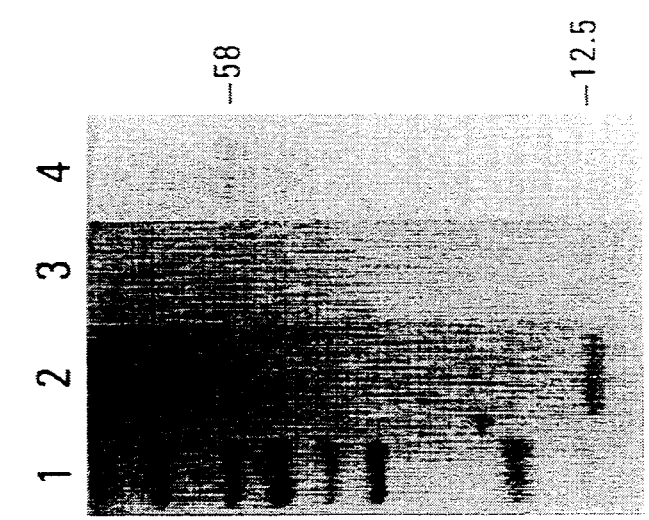
Figure 18C:
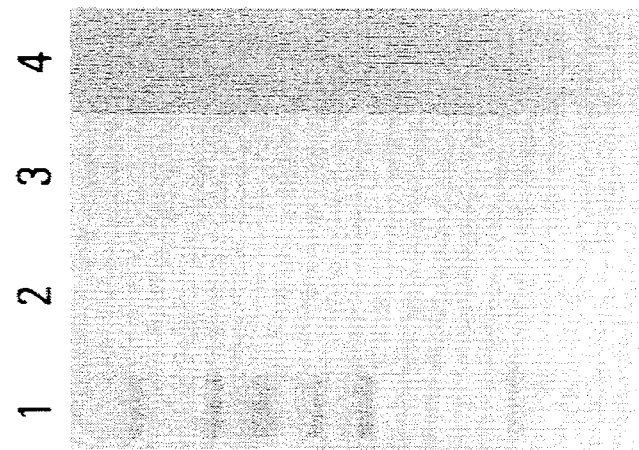

FIG. 18 illustrates a Western blot analysis of immunoaffinity isolated huTF as described in Example 25. Fifteen percent polyacrylamide gels were loaded as follows: lane 1 contains molecular weight standards with apparent molecular weights indicated to the left of panel A in kilodaltons (k); lane 2 contains 1 ug purified human hemoglobin reduced prior to electrophoresis; lane 3 contains 0.5 ug isolated huTF reduced prior to electrophoresis; and lane 4 contains 0.5 ug non-reduced and isolated huTF. After SDS-PAGE the resulting protein bands were electrophoretically transferred to nitrocellulose. The Western blots thus formed were immunoreacted with 0.2 ug/ml affinity-purified, rabbit anti-huTF IgG (Panel A), 1 ug/ml rabbit anti-hemoglobin IgG (Panel B), or 1 ug/ml nonimmune rabbit IgG (Panel C). Apparent molecular weights of immunostained bands are indicated in kDa on the right.

Figure 19:
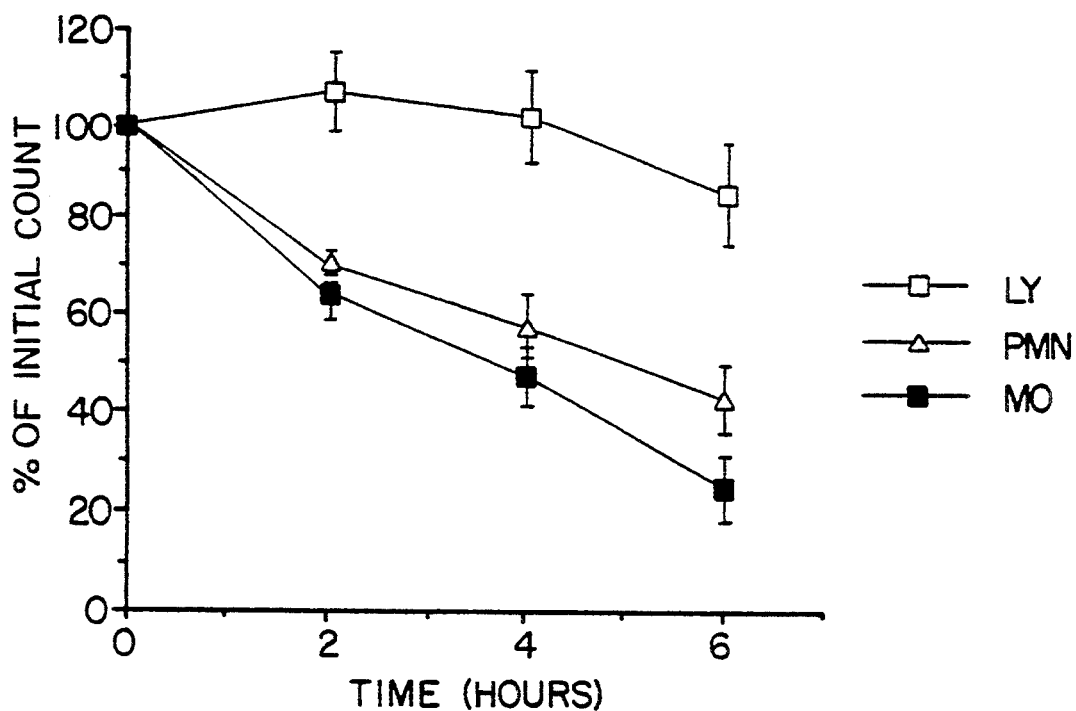

FIG. 19 illustrates differential leukocyte count during SECC. The total leukocyte count was multiplied by the percent on a differential count to obtain the absolute lymphocyte (LY), neutrophil (PMN) and monocyte (MO). Values are expressed as percentage of initital count for each cell type. The decrease in total leukocytes is primarily due to the attachment of neutrophils and monocytes to the surface. Lymphocyte count was minimally affected by recirculation.

Figure 20:
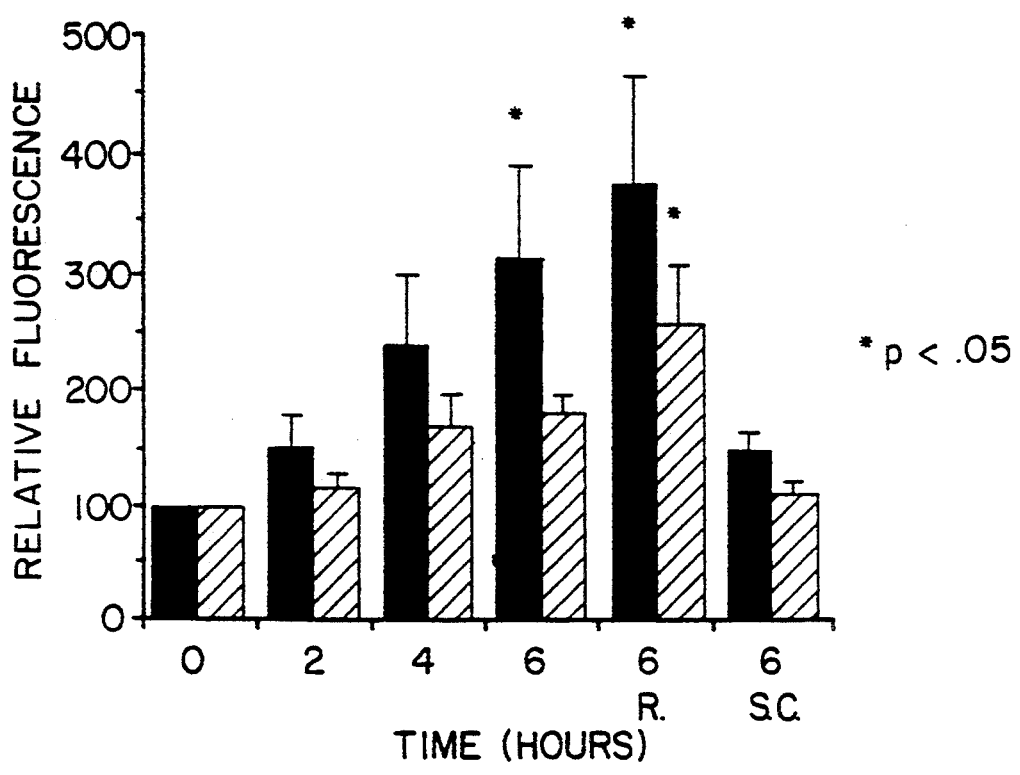

FIG. 20 illustrates flow cytometry analysis of relative TF display on monocytes. Mononuclear cells were reacted with a cocktail of TF MAbs which include those recognizing epitopes expressed on the TF in complex with factor VII/VIIa (black bars). Free TF, unoccupied by factor VII/VIIa, is differentially reported by MAb 9C3 (hatched bars). Baseline fluorescence was arbitrarily taken as 100. The comparisons show a statistically significant increase in TF by six hours compared to baseline, with the highest amount present on the cells recovered from the surfaces of the oxygenator. On this and subsequent figures and tables, R=recovered cells, SC=standing control.

FIG. 21 illustrates typical flow cytometric pattern for TF of lymphocytes and monocytes.

Figure 21A:
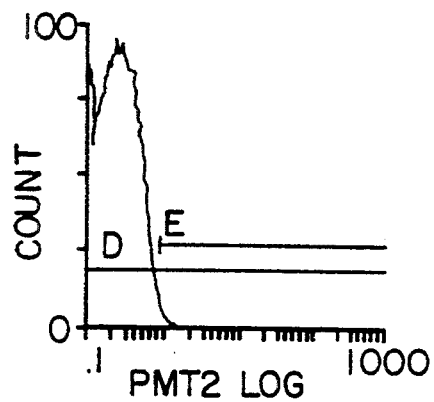

FIG. 21A illustrates the output flow cytometric pattern for TF of lymphocytes and monocytes prior to circulation.

Figure 21B:
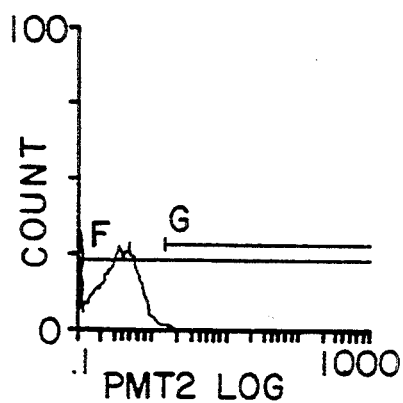

FIG. 21B illustrates the percentage of TF positive cells prior to circulation, which were identified by setting the regions G and E on 0 hour samples to include 1% of the cells.

Figure 21C:
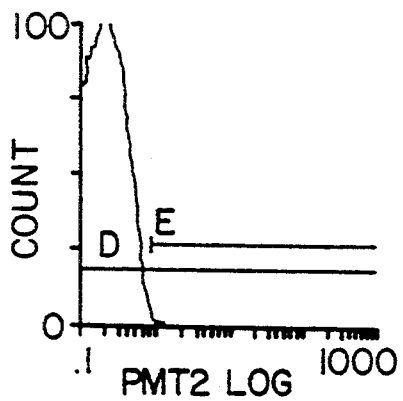

FIG. 21C illustrates the output flow cytometric pattern for TF of lymphocytes and monocytes after circulation.

Figure 21D:
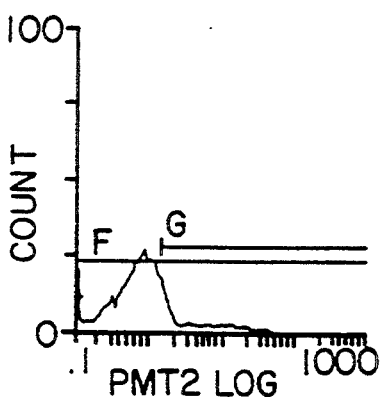

FIG. 21D illustrates the percentage of TF positive cells after circulation, which were identified by setting the regions G and E on 0 hour samples to include 1% of the cells.

Figure 22:
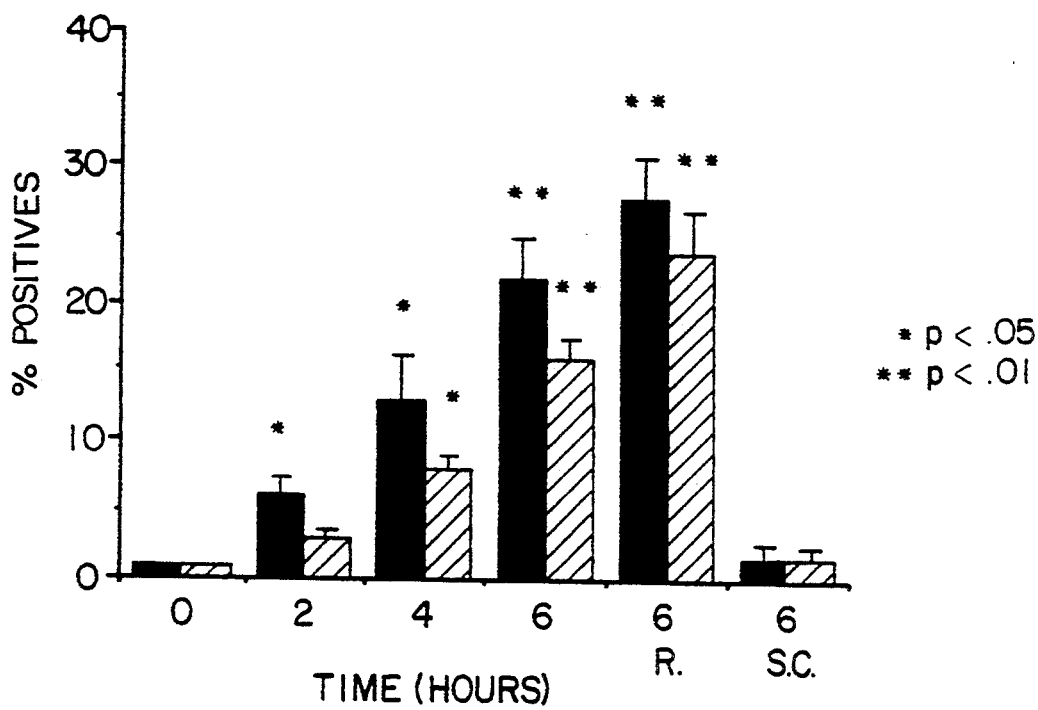

FIG. 22 illustrates percent monocytes positive for TF during SECC. TF reported by a TF MAb cocktail (black bars) or free TF dependent MAb 9C3 alone (hatched bars) demonstrate a continuous increase of TF positive cells which becomes significant by 2 h for the mixture of MAbs and by 4 h for MAb 9C3.

Figure 23:
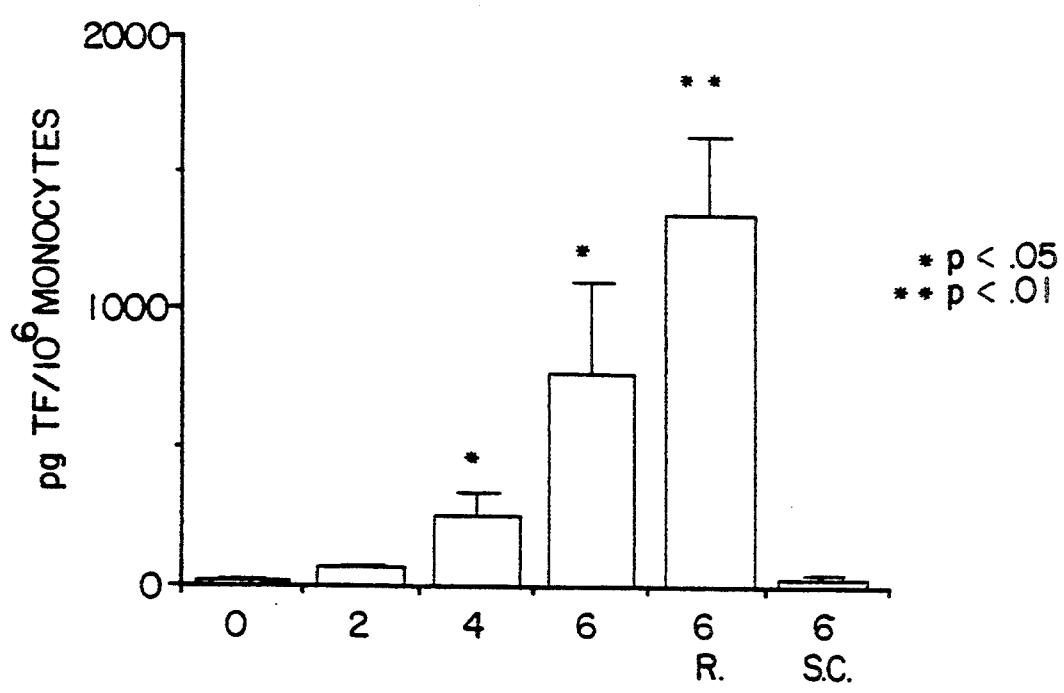

FIG. 23 illustrates procoagulant activity (PCA) of mononuclear cells during SECC. The PCA expressed as pg TF/$10^6$ monocytes was significantly increased over 0 times by 4 hours, and increased further at 6 hours in both the circulatory and adherent cells.

Figure 24:
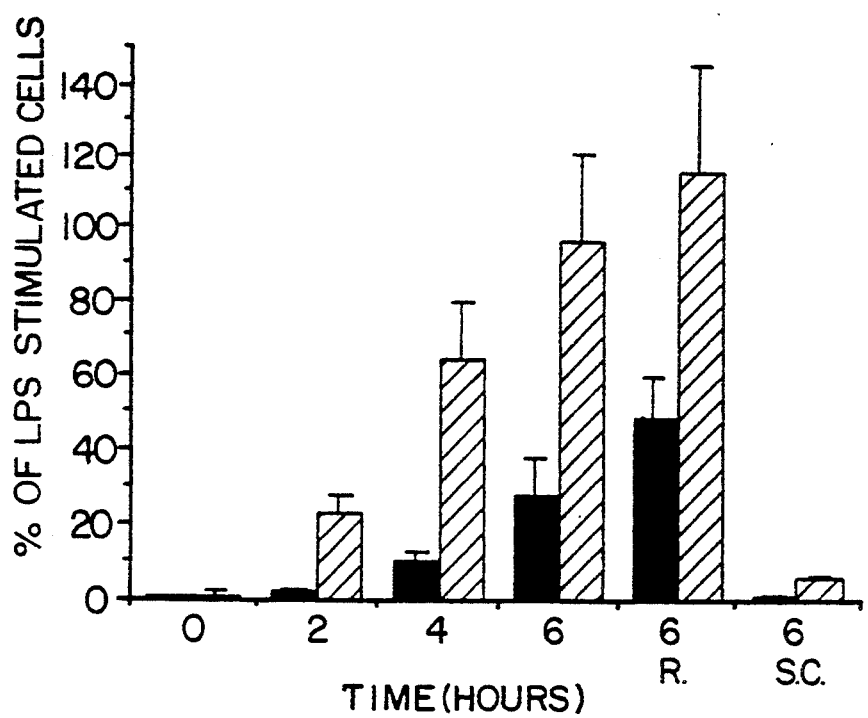

FIG. 24 illustrates monocyte TF compared to LPS stimulated samples. The TF was expressed as percentage of the maximal stimulus both for monocyte associated fluorescence (hatched bars) and for monocyte PCA (black bars).

Figure 25:
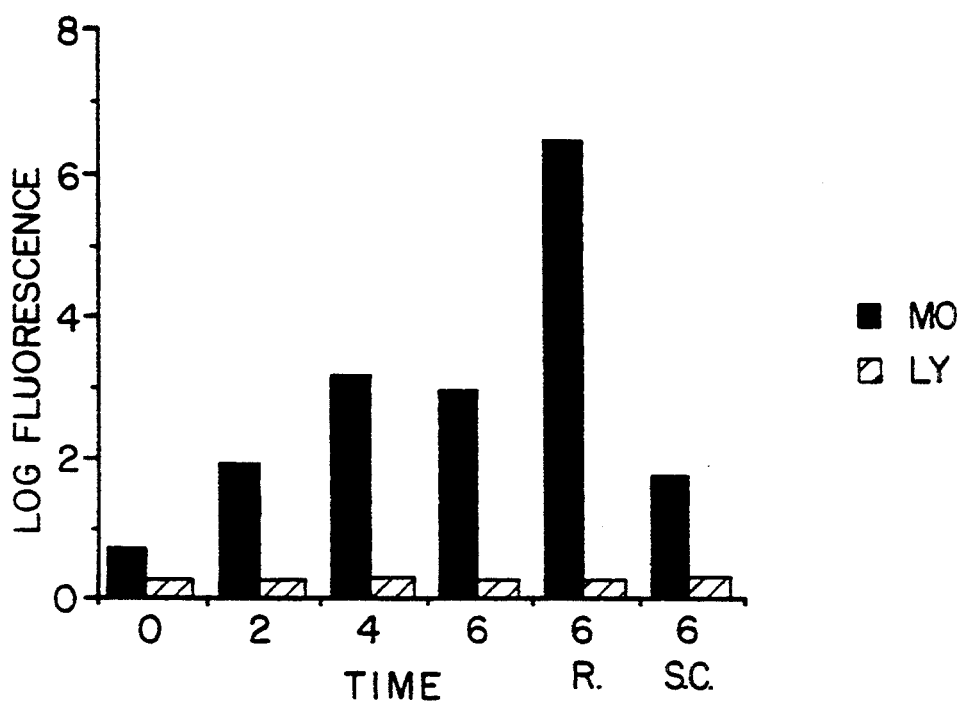

FIG. 25 illustrates monocyte surface Mac-1 fluorescence during SECC. The expression MO Mac-1 was measured by reactivity with MAb LM2 to the alpha chain of the leukocyte integrin Mac-1. Lymphocytes (LY) were negative. The data is representative of two similar experiments. (Note that the ordinate is logarithmic.)

DETAILED DESCRIPTION OF THE INVENTION

A. Definitions

Amino Acid: All amino acid residues identified herein are in the natural L-configuration. In keeping with standard polypeptide nomenclature, *J. Biol. Chem.*, 243:3557–59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues up to a total of about fifty residues in the polypeptide chain.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Base Pair (bp): A partnership of adenine (A) with thymine (T), or of cytosine (C) with guanine (G) in a double stranded DNA molecule.

B. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

The DNA segments of the present invention are characterized as including a DNA sequence that encodes a human tissue factor heavy chain protein (huTFh). In preferred embodiments the DNA segment includes a DNA sequence that encodes a human tissue factor heavy chain precursor protein (pre-huTFh). That is, the DNA segments of the present invention are characterized by the presence of a huTFh or, more preferably, a pre-huTFh, structural gene. Further preferred are DNA segments that include a DNA sequence forming a structural gene encoding a soluble huTFh or soluble pre-huTFh protein. Preferably the gene is present as an uninterrupted linear series of codons where each codon codes for an amino acid residue found in the huTFh or pre-huTFh protein, i.e., a gene free of introns.

Thus, a DNA segment consisting essentially of the sequence shown in FIG. 2 from about position 130 at its 5' terminus to about position 918 at its 3' terminus, and capable of expressing huTFh constitutes one embodiment of the present invention. A DNA segment consisting essentially of the sequence shown in FIG. 2 from about position 34 to about position 918 and capable of expressing pre-huTFh constitutes another embodiment of the invention.

A preferred soluble huTFh molecule lacks the amino acid residues encoded by the last about one hundred-fifty bases at the 5' terminus of the DNA that codes for huTFh. Thus, a DNA segment consisting essentially of the sequence shown in FIG. 2 from about position 130 at its 5' terminus to about position 756 through about position 801 at its 3' terminus, and capable of expressing soluble huTFh constitutes a further preferred embodiment of this invention. Exemplary preferred DNA segments forming soluble huTFh structural genes are those having a nucleotide base sequence represented by FIG. 2 from about base 130 to about base 756, from about base 130 to about base 771, from about base 130 to about base 786, and from about base 130 to about base 801.

Preferred DNA segments encoding a soluble pre-huTFh are similar to those encoding soluble huTFh except that they encode proteins containing an amino terminal leader sequence such as amino acid residues −32 to 0 as shown in FIG. 1. Thus, a preferred DNA segment forming a structural gene encoding soluble pre-huTFh consists essentially of the sequence shown in FIG. 2 from about position 34 at its 5' terminus to about position 756 through about position 801 at its 3' terminus. Exemplary preferred soluble pre-huTFh-encoding DNA segments are those having a nucleotide base sequence represented by FIG. 2 from about base 34 to about base 756, from about base 34 to about base 771, from about base 34 to about base 786, and from about base 34 to about base 801.

Homologous DNA and RNA sequences that encode the above huTFh and pre-huTFh proteins, including their soluble forms, are also contemplated, as discussed before.

DNA segments that encode huTFh and pre-huTFh proteins can easily be synthesized by chemical techniques, for example, the phosphotriester method of Matteucci et al., *J. Am. Chem. Soc.*, 103:3185 (1981). (The disclosures of the art cited herein are incorporated herein by reference.) Of course, by chemically synthesizing the coding sequence, any desired modifications can be made simply by substituting the appropriate bases for those encoding the native amino acid residue sequence. However, DNA molecules including sequences exactly homologous to those shown in FIG. 2 are preferred.

Furthermore, DNA segments consisting essentially of structural genes encoding the huTFh and pre-huTFh proteins can be obtained from recombinant DNA molecules containing those genes. For instance, the plasmid type recombinant DNA molecules pCTF64, pCTF314 and pCTF403 each contain DNA sequences encoding different portions of the huTFh and pre-huTFh proteins and together possess the entire sequence of DNA necessary for expression of either protein. Cultures of *Escherichia coli* (*E. coli*) transformed with either pCTF64, pCTF314 or pCTF403 have been deposited pursuant to Budapest Treaty requirements with the American Type Culture Collection, (ATCC) 12301 Parklawn Drive, Rockville, Md. 20852 on Mar. 27, 1987 and were assigned the following respective accession numbers 67370, 67368 and 67369.

A DNA segment that includes a DNA sequence encoding huTFh or pre-huTFh can be prepared by operatively linking (ligating) appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA segments.

C. Recombinant DNA Molecules

The recombinant DNA molecules of the present invention can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. Vectors capable of directing the expression of huTFh and pre-huTFh genes are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the huTFh or pre-huTFh structural genes included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the huTFh or pre-huTFh genes in a bacterial host cell, such as E. coli, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327-341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cell. Biol.*, 4:1730-37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3' single-stranded termini with their 3'-5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

D. Transformed Cells and Cultures

The present invention also relates to a host cell transformed with a recombinant DNA molecule of the present invention preferably an rDNA capable of expressing a soluble form of huTFh or pre-huTFh. The host cell can be either procaryotic or eucaryotic. Bacterial cells are preferred procaryotic host cells and typically are a strain of E. coli such as, for example the E. coli strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730-37 (1984); Graham et al., *Virol.*, 52:456 (1973); and Wigler et al., *Proc. Natl. Acad. Sci. USA*, 76:1373-76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of huTFh or pre-huTFh. For example, cells successfully transformed with an expression vector produce proteins displaying huTFh or pre-huTFh antigenicity. Samples of cells suspected of being transformed are harvested and assayed for huTFh or pre-huTFh using antibodies specific for those antigens, such as those produced by a hybridoma of the present invention.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying huTFh or pre-huTFh antigenicity, and more preferably, biologically active huTFh.

Nutrient media useful for culturing transformed host cells are well known in the art and can be obtained from several commercial sources. In embodiments wherein the host cell is mammalian, a "serum-free" medium is preferably used.

E. Methods for Producing huTFh and pre-huTFh Proteins

Another aspect of the present invention pertains to a method for producing proteins displaying huTFh antigenicity. Proteins that display huTFh antigenicity are proteins that immunoreact with antibodies induced by native tissue factor. Proteins displaying huTFh antigenicity are useful as antigens and for raising antibodies, each of which can be used in the diagnostic systems and methods of the present invention.

The present method entails initiating a culture comprising a nutrient medium containing host cells, preferably human cells, transformed with a recombinant DNA molecule of the present invention that is capable of expressing a huTFh or pre-huTFh protein, preferably a soluble huTFh or soluble pre-huTFh protein. The culture is maintained for a time period sufficient for the transformed cells to express a huTFh or pre-huTFh protein. The expressed protein is then recovered from the culture. In preferred embodiments, the huTFh proteins produced by the methods of the present invention additionally display huTFh biological activity i.e., the ability to bind factor VII/VIIa. Those methods include culturing mammalian host cells transformed with a recombinant DNA molecule capable of expressing the pre-huTFh gene in the cells. The culturing results in expression of the pre-huTFh protein and subsequent intracellular post-translational modification of the pre-huTFh to form a biologically active huTFh protein.

Methods for recovering an expressed protein from a culture are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoadsorption and the like can be performed using well known methods.

F. huTFh and pre-huTFh Protein Compositions and Expression Products

Also contemplated by the present invention are the huTFh and pre-huTFh protein expression products of the rDNAs of the present invention. In preferred embodiments the huTFh and pre-huTFh expression products have an amino acid residue sequence corresponding to residues 1 to 263 and −32 to 263, respectively, as shown in FIG. 1. Preferably, the expressed protein is at least 90 percent, more preferably at least 95 percent, of the length of the pre-huTFh and huTFh amino acid residue sequence length shown in FIG. 1.

In another embodiment, soluble forms of huTFh and pre-huTFh and compositions containing soluble huTFh and/or soluble pre-huTFh are contemplated. The term "soluble" as used herein refers to huTFh and pre-huTFh molecules characterized as consisting essentially of the extracellular domain of the native huTFh and pre-huTFh molecules, i.e., that portion of the huTFh and pre-huTFh molecules that is amino-terminal to residue 220 as shown in FIG. 1. Soluble huTFh and soluble pre-huTFh therefore do not contain any substantial portion of the transmembrane anchor region formed in the native molecules (residues 220 through 242 as shown in FIG. 1). It should be noted that the terms "huTFh" and "pre-huTFH" as used herein contemplate and include, unless otherwise specifically set forth, the soluble forms of those proteins.

Because soluble huTFh and soluble pre-huTFh do not contain a hydrophobic transmembrane anchor region they do not aggregate substantially in physiologically tolerable aqueous solutions. Therefore, soluble huTFh and soluble pre-huTFh are further characterized by their ability to form an aqueous solution using a physiologically tolerable diluent, at protein concentration of about 0.1 pg/ml to about 100 ng/ml, wherein at least about 70, preferably about 80, and more preferably about 90 weight percent of the huTFh or pre-huTFh protein present is in non-aggregated (monomeric) form. Methods for determining the amount of aggregation present in a protein solution are well known in the art and include size fractionation by exclusion column chromatography.

A preferred soluble huTFh protein has an amino acid residue sequence represented by FIG. 1 from about residue 1 at its amino terminus to about residue 209 through about residue 224 at its carboxy terminus. Thus, preferred soluble huTFh proteins are those having an amino acid residue sequence represent by FIG. 1 from about residue 1 to about residue 209, from about residue 1 to about residue 214, from about residue 1 to about residue 219, and from about residue 1 to about residue 224.

A preferred soluble pre-huTFh protein has an amino acid residue sequence represented by FIG. 1 from about residue 32 at its amino terminus to about residue 209 through about residue 224 at its carboxy terminus. Thus, preferred soluble pre-huTFh proteins are those having an amino acid residue sequence represented by FIG. 1 from about residue −32 to about residue 209, from about residue −32 to about residue 214, from about residue −32 to about residue 219, and from about residue −32 to about residue 224.

In one embodiment, the huTFh and pre-huTFh expression products are not glycosylated, i.e., they are produced in a procaryotic cell transformed with a rDNA of the present invention. A Non-glycosylated form of huTFh and pre-huTFh is useful as an immunogen and as an antigen in an inoculum and diagnostic system of the present invention.

Eucaryotically produced huTFh and pre-huTFh are typically glycosylated and biologically active, in addition to being antigenic and immunogenic. As used herein, the phrase "biologically active" refers to a huTFh or pre-huTFh protein or polypeptide having the capacity to induce factor VII/VIIa-dependent coagulation.

Thus, the present invention contemplates a composition comprising an aqueous solution containing biologically active huTFh substantially free of human tissue factor light chain protein. Preferably, the composition is also substantially free of entities such as ionic detergents, e.g., sodium dodecyl sulfate (SDS), polyacrylamide and tissue-derived proteins having an apparent molecular weight of less than about 15,000 daltons as determined by SDS-polyacrylamide gel electrophoresis (SDS-PAGE).

The aqueous huTFh-containing solutions contain biologically active huTFh in an amount sufficient to assay the coagulation competence of a vascular system fluid sample such as blood or blood derived products such as citrated plasma. The phrase "coagulation competence" refers to the ability of the vascular fluid sample to clot in the presence of biologically active huTFh. Typical huTFh protein concentrations sufficient to assay for coagulation competence are about 0.1 pg/ml to about 100 ng/ml, preferably about 1 pg/ml to about 10 ug/ml, and more preferably about 10 pg/ml to about 1 ng/ml, using sample to huTFh volume ratios similar to those in Example 2. Of course, solutions containing huTFh at concentrations higher than those required to assay coagulation competence but that can be diluted to a preferred concentration are also contemplated.

In preferred embodiments, the huTFh-containing aqueous solutions include huTFh dispersed in a phospholipid or non-ionic detergent. Typical phospholipid: huTFh-protein weight ratios range from about 5:1 to 12,000:1 preferably about 50:1 to about 5,000:1 and more preferably about 100:1 to 2,500:1.

G. Polypeptides

The polypeptides of the present invention each contain no more than about 50, more usually fewer than about 35 and preferably fewer than about 25 amino acid residues, and contains at least about 10 residues. In addition, the polypeptides of the present invention are characterized by their amino acid residue sequence and novel functional properties.

Thus, one embodiment of a polypeptide of the present invention is a huTFh binding site polypeptide analog characterized in part by its ability to competitively inhibit the binding of huTF to blood coagulation factor VII/VIIa. Preferably, a binding site analog of the present invention binds factor VII/VIIa without producing an activated complex, i.e., without initiating coagulation.

The word "complex" as used herein refers to the product of a specific binding reaction such as an antibody-antigen or receptor-ligand reaction. Exemplary complexes are immunoreaction products and tissue factor-factor VII/VIIa binding reaction products, designated herein as TF:VII/VIIa.

In preferred embodiments, a huTF binding site analog includes at least the following amino acid residue sequence:

-VNQVYT-, representing amino acid residues 30-35 as shown in FIG. 1.

More preferably, a huTFh binding site analog includes at least one of the following amino acid residue sequences:

-VNQVYTVQIST-, and

-LYYWKSSSSGKKT-.

Those sequences represent huTFh amino acid residues 30-40 and 155-167, respectively, as shown in FIG. 1.

Still more preferably, a huTFh binding site analog includes an amino acid residue sequence chosen from the group consisting of:

-EPKPVNQVYTVQISTKSGDWKSKC-, and

-VFGKDLIYTLYYWKSSSSGKKT-, representing amino acid residues 26-49 and 146-167, respectively, as shown in FIG. 1.

Preferred huTFh binding site polypeptide analogs include those whose amino acid residue sequences are shown in Table 1.

TABLE 1

| Designation[a] | Amino Acid Residue Sequence |
| --- | --- |
| p24-35 | H—EWEPKPVNQVYT—OH |
| p26-49 | H—EPKPVNQVYTVQISTKSGDWKSKC—OH |
| p144-159 | H—RDVFGKDLIYTLYYWK—OH |
| p146-167 | H—VFGKDLIYTLYYWKSSSSGKKT—OH |
| p159-169 | H—IYTLYYWK—SSSSGKKTAK—OH |
| P157-169 | H—YWKSSSSGKKTAK—OH |

TABLE 1-continued

| Designation[a] | Amino Acid Residue Sequence |
|---|---|
| p161-189 | H—SSSGKKTAKTNTNEFLIDVDKGENYCFSV—OH |

[a] The laboratory designation of each polypeptide represent the included amino acid residue sequence as shown in FIG. 1

Polypeptides p26-49, p146-167 and p161-189 are also characterized by their ability to neutralize (competitively inhibit) the binding of anti-huTFh antibody molecules to huTFh. Other polypeptides of the present invention having the ability to neutralize the binding of anti-huTFh antibodies to huTFh include those in Table 2.

TABLE 2

| Designation | Amino Acid Residue Sequences |
|---|---|
| p1-30 | H—SGTTNTVAAYNLTWKSTNFKTILEWEPKPV—OH |
| p40-71 | H—TKSGDWKSKCFYTTDTECDLTDEIVKDVKQTY—OH |
| p41-49 | H—KSGDWKSKC—OH |
| p56-71 | H—ECDLTDEIVKDVKQTY—OH |
| p72-104C[a] | H—LARVFSYPAGNVESTGSAGEPLYENSPEFTPYLC—OH |
| p94-123 | H—YENSPEFTPYLETNLGQPTIQSFEQVGTKV—OH |
| p190-209 | H—QAVIPSRTVNRKSTDSPVEC—OH |

[a] The "C" added to the laboratory designation indicates a cysteine residue was added to the indicated sequence as a linker for protein conjugation.

It should be understood that a polypeptide of the present invention need not be identical to the amino acid residue sequence of huTFh, so long as the subject polypeptides are able to compete with native tissue factor for binding to factor VII/VIIa and/or are able to competitively inhibit the binding of anti-huTFh antibody molecules to huTFh. Therefore, a present polypeptide can be subject to various changes, such as insertions, deletions and substitutions, either conservative or non-conservative, where such changes provide for certain advantages in their use.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

When a polypeptide of the present invention has a sequence that is not identical to the sequence of native huTFh because one or more conservative or non-conservative substitutions have been made, usually no more than about 20 number percent and more usually no more than 10 number percent of the amino acid residues are substituted, except where additional residues have been added at either terminus for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal—NH$_2$ acylation, e.g., acetylation, or thioglycolic acid amidation, terminal-carboxylamidation, e.g., ammonia, methylamine, etc.

When coupled to a carrier via a linker to form what is known in the art as a carrier-hapten conjugate, a polypeptide of the present invention is capable of inducing antibodies that immunoreact with huTFh. In view of the well established principle of immunologic cross-reactivity, the present invention therefore contemplates antigenically related variants of the polypeptides shown in Tables 1 and 2. An "antigenically related variant" is a polypeptide that includes at least a six amino acid residue sequence portion of a polypeptide from Table 1 or Table 2 and which is capable of inducing antibody molecules that immunoreact with a polypeptide from Table 1 or 2 and huTFh.

Also contemplated by the present invention is a composition comprising an aqueous solution of a huTFh binding site polypeptide analog wherein the polypeptide is dispersed in a phospholipid or non-ionic detergent. Typical phospholipid: polypeptide analog weight ratios range from about 5:1 to 200:1, preferably from about 30:1 to 80:1 and more preferably about 45:1 to 55:1. Preferred huTFh binding site polypeptide analogs suitable for use dispersed in a phospholipid are those listed in Table 4, section II.

A polypeptide of the present invention can be synthesized by any techniques that are known to those skilled in the polypeptide art. An excellent summary of the many techniques available may be found in J. M. Stewart and J. D. Young, "Solid Phase Peptide Synthesis" W. H. Freeman Co., San Francisco, 1969, and J. Meienhofer, "Hormonal Proteins and Peptides" Vol., 2, p. 46, Academic Press (New York), 1983 for solid phase peptide synthesis, and E. Schroder and K. Kubke, "The Peptides", Vol. 1, Academic Press (New York), 1965 for classical solution synthesis.

H. Inocula

In another embodiment, a polypeptide of this invention or an antigenically related variant thereof is used in a pharmaceutically acceptable aqueous diluent composition to form an inoculum that, when administered in an effective amount, is capable of inducing antibodies that immunoreact with huTFh. The word "inoculum" in its various grammatical forms is used herein to describe a composition containing a polypeptide of this invention as an active ingredient used for the preparation of antibodies against huTFh. When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies as already noted.

As already noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, Vol. 8, Supp-1. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the Polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

I. Antibodies and Antibody Compositions

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab' F(ab' and F(v).

An antibody composition of the present invention is an anti-peptide antibody characterized as containing antibody molecules that immunoreact with huTFh and at least one specific polypeptide of this invention.

For instance, an antibody composition of the present invention containing antibody molecules that immunoreact with huTFh and a polypeptide analog of the tissue factor binding site, but do not substantially immunoreact with p204-226, is capable of neutralizing the ability of tissue factor to bind factor VII/VIIa. Thus, preferred antibody compositions are those containing antibody molecules that immunoreact with huTFh and p26-49 or p146-167, and are substantially free from immunoreaction with p204-226.

It should be noted that polyclonal antisera raised to huTFh contain antibodies that immunoreact with p204-226. Thus, the substantial absence of anti-p204-226 immunoreactivity is a feature that distinguishes the present antibody compositions from those described in the art.

An antibody composition of the present invention is typically produced by immunizing a mammal with an inoculum of the present invention and thereby induce in the mammal antibody molecules having the appropriate polypeptide immunospecificity. The antibody molecules are then collected from the mammal and isolated to the extent desired by well known techniques such as, for example, by immunoaffinity chromatography. The antibody composition so produced can be used in, inter alia, the diagnostic methods and systems of the present invention to detect huTFh in a body sample.

Monoclonal antibody compositions are also contemplated by the present invention. A monoclonal antibody composition contains, within detectable limits, only one species of antibody combining site capable of effectively binding huTFh. Thus, a monoclonal antibody composition of the present invention typically displays a single binding affinity for huTFh even though it may contain antibodies capable of binding proteins other than huTFh. In one embodiment, a monoclonal antibody composition contains antibody molecules that immunoreact with huTFh and a polypeptide analog of the tissue factor binding site, preferably p26-49 or p146-167.

In another embodiment, the present invention contemplates an anticoagulant (neutralizing) MoAb containing antibody molecules that immunoreact with huTFh and inhibit huTFh-initiated coagulation. A preferred MoAb that inhibits coagulation is further characterized as immunoreacting with a polypeptide of the present invention, preferably a huTFh binding site polypeptide analog, and more preferably a polypeptide as shown in Table 1.

In another embodiment, an anticoagulant MoAb contains antibody molecules that immunoreact with huTFh and a huTFh:factor VII/VIIa complex, and inhibit (neutralize) huTFh-initiated coagulation. A preferred anticoagulant MoAb is further characterized as immunoreacting with huTFh polypeptides p1-30 or p26-49, and preferably does not immunoreact with huTFh polypeptide p56-71.

Methodologies involving extracorporeal circulation, such as cardiopulmonary bypass (CPB), often require continuous high dose anticoagulation to prevent thromboembolic complications. For example, during CPB, complement activation with anaphylatoxin generation occurs and requires large amounts of heparin in order to prevent thrombotic events. Simulated extracorporeal circulation (SECC) is associated with increased neutrophil superoxide generation and slight shortening of leukocyte-generated clotting times by two hours. (Stahl, et al., *J. Thorac. Cardiovasc. Surg.*, 101:230, 1991). In addition, use of extracorporeal membrane oxygenation (ECMO) has been associated with an increased incidence of thromboembolic complications. Erythrocytes and leukocytes are entrapped within the fibrin meshwork in the oxygenator bypass segment, and it has been proposed that the membrane oxygenator may be a source of thrombogeneis (Fink, et al., *J. Pediat.*, 115:621, 1989). By studying SECC, it was unexpectedly found that tissue factor antigen is expressed by monocytes during prolonged SECC and contributes significantly to the increased risk of thrombotic events. This finding stands in sharp contrast to the existing dogma which had previously taught that coagulation associated with extracorporeal circulation shunts arose through the contact activation system, independent of tissue factor.

Therefore, in another embodiment, the invention provides a method of inhibiting coagulation in extracorporeal circulation in a subject, comprising administering to the subject a therapeutically effective amount of a monoclonal antibody which inhibits the ability of tissue factor to bind factor VII/VIIa.

The preferred form of extracorporeal circulation of the invention is exemplified by cardiopulmonary bypass (CPB) and other shunt procedures. The subject may be any mammal and preferably a human. The term "therapeutically effective amount" refers to that amount of monoclonal antibody which inhibits coagulation by preventing complex formation between tissue factor and factor VII/VIIa. The monoclonal antibody utilized should bind to tissue factor with the same specificity as the monoclonal antibodies of the invention. Preferably, the monoclonal antibody is the TF8-5G9, TF9-5B7 or TF9-6B4 antibodies of the invention.

The antibody can be administered to the subject parenterally by injection or by gradual perfusion over time. Preferably, administration is intravenous. Preparations for administration include sterile aqueous or non-aqueous solutions, suspensions, and emulsions. Intravenous vehicles include fluid and nutrient replenishers, electrolyte replenishers (such as those based on Ringer's dextrose) and the like. Preservatives and other additives may also be present such as, for example, antimicrobials, antioxidants, chelating agents, and inert gases and the like.

The present invention also contemplates a non-neutralizing monoclonal antibody composition containing antibody molecules that do not neutralize the ability of tissue factor to initiate coagulation. Preferably, such a composition contains antibody molecules that immunoreact with huTFh and the polypeptide p1-30 and is produced (secreted) by hybridoma TF9-10H10.

A monoclonal antibody composition of the present invention can be produced by initiating a monoclonal hybridoma culture comprising a nutrient medium containing a hybridoma that secretes antibody molecules of the appropriate polypeptide specificity.

The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c. The monoclonal antibody compositions produced by the above method can be used, for example, in diagnostic and therapeutic modalities wherein formation of an huTFh-containing immunoreaction product is desired.

J. Hybridomas

The hybridomas of the present invention are characterized as producing antibody molecules that immunoreact with huTFh. A preferred hybridoma is further characterized as producing antibody molecules that inhibit huTFh-initiated coagulation, and preferably immunoreact with a polypeptide of the present invention, preferably a huTFh binding site polypeptide analog, and more preferably a polypeptide as shown in Table 1. In further preferred embodiments, an anticoagulant MoAb immunoreacts with non-human primate TF.

In another preferred embodiment, a hybridoma of this invention produces antibody molecules that immunoreact with huTFh and a huTFh:factor VII/VIIa complex, and neutralize huTFh-initiated coagulation. Preferably, a hybridoma producing antibodies that immunoreact with a huTFh:factor VII/VIIa complex are further characterized by the ability of said antibody molecules to immunoreact with huTFh polypeptides p1-30 or p26-49, preferably both, and more preferably wherein said antibody molecules do not immunoreact with huTFh polypeptide p56-71.

Methods for producing hybridomas producing (secreting) antibody molecules having a desired immunospecificity, i.e., having the ability to immunoreact with a particular protein and/or polypeptide, are well known in the art. Particularly applicable is the hybridoma technology described by Niman et al., *Proc. Natl. Acad. Sci. USA*, 80:4949–4953 (1983). Preferred hybridomas are those shown in Table 5 in Example 13.

Hybridoma cultures TF8-5G9, TF9-6B4 and TF9-10H10 have been deposited pursuant to Budapest Treaty requirements with the American Type Culture Collection (ATCC) at 12301 Parklawn Drive, Rockville, Md. 10852, USA, on Mar. 27, 1987, and were assigned the following respective accession numbers HB9382, HB9381 and HB9383.

K. Therapeutic Methods and Compositions

The huTFh factor VII/VIIa binding site polypeptide analogs, antibody compositions monoclonal antibody compositions and anticoagulant MoAbs of the present invention each can be used to modulate the binding of factor VII/VIIa by tissue factor in vivo.

For instance, a huTFh factor VII/VIIa binding site polypeptide analog can be used in a pharmaceutically acceptable composition that, when administered to a human subject in an effective amount, is capable of competitively inhibiting the binding of factor VII/VIIa to tissue factor. That inhibition is believed to result in a decreased rate of tissue factor-factor VII/VIIa complex formation. Thus, in vivo administration of an huTFh factor VII/VIIa binding site polypeptide analog can be used to modulate any physiological response initiated by tissue factor binding to factor VII/VIIa, such as coagulation and some inflammatory responses. In preferred embodiments, the polypeptide is administered when dispersed in a phospholipid as previously described.

Another approach to modulating the binding of factor VII/VIIa by tissue factor in vivo is to intravenously administer an effective amount of an antibody composition (anti-peptide antibody) or an anticoagulant MoAb of the present invention. Preferably the antibody molecules are those that contain the paratopic region and are free from the Fc region, such as immunoglobulin fragments F(ab')$_2$, Fab and the like. Therapeutically effective amounts of an anticoagulant MoAb are in the range of 15 ug/kg body weight to 5 mg/kg body weight, preferably in the range of about 100 ug/kg body weight to about 1 mg/kg body weight and more preferably in the range of about 150 ug/kg body weight to about 500 ug/kg body weight.

In another embodiment, the antibody molecules of a MoAb, anticoagulant MoAb or non-neutralizing MoAb of the present invention are linked to an anti-tumor agent to form an anti-tumor therapeutic composition. An effective amount of anti-tumor therapeutic composition thus formed can be administered to a human subject having tumor cells that expresses tissue factor on their surface. Exemplary of such tumor cells are carcinomas of the breast and lung.

Typical of the anti-tumor agents contemplated herein are radionuclides such as $^{131}$I, $^{188}$Re, $^{212}$Bi and the like. Methods for producing radionuclide-conjugated monoclonal antibody therapeutic compositions and their use are described in Kozak et al., *Trends In Biotech.*, 4:259–264 (1986).

The polypeptide- or antibody molecule-containing compositions administered take the form of solutions or suspensions, however, polypeptides can also take the form of tablets, pills, capsules, sustained release formulations or powders. In any case, the compositions contain 0.10%–95% of active ingredient, preferably 25–70%.

The preparation of therapeutic compositions which contain polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody molecule composition can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody molecule-containing compositions are conventionally administered topically or intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's blood coagulation system to utilize the active ingredient, and degree of inhibition or neutralization of tissue factor binding capacity desired. Precise amounts of active ingredient required to be administered depend on the judgment of the practitioner and are peculiar to each individual. However, suitable polypeptide dosage ranges are of the order of one to several milligrams of active ingredient per individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

L. Diagnostic Systems

A diagnostic system in kit form of the present invention includes, in an amount sufficient for at least one assay, an expressed protein, polypeptide, antibody composition or monoclonal antibody composition of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a reagent species.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or antibody molecule of the present invention. Exemplary specific binding agents are antibody molecules, complement proteins or fragments thereof, protein A, blood coagulation factor VII/VIIa, bovine tissue factor and the like. Preferably the specific binding agent can bind the reagent species when the species is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of huTFh in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; No. 3,850,752; and No. 4,016,043, which are all incorporated herein by reference.

Thus, in preferred embodiments, the expressed protein, polypeptide, or antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

M. Assay Methods

The present invention contemplates any method that results in detecting huTFh by producing a complex containing an expressed protein, polypeptide or antibody molecule contained in an antibody or monoclonal antibody composition of the present invention. Those skilled in the art will understand that there are numerous well known clinical diagnostic chemistry procedures that can be utilized to form those complexes. Thus, while exemplary assay methods are described herein, the invention is not so limited.

1. Thrombus Detection

A method for detecting the presence of a thrombus in a human subject is contemplated. An effective amount of a monoclonal antibody composition of the present invention containing antibody molecules linked to an in vivo indicating means is intravenously administered into the subject. In preferred embodiments the labeled antibody molecules are those that immunoreact with huTFh and a polypeptide from Tables 1 and 2 but not p204-226, more preferably those produced by hybridoma TF8-5G9, TF9-6B4 or TF9-10H10.

The subject is then maintained for a predetermined time period sufficient for the labeled antibody molecules to react with huTFh present as part of a thrombus and form a complex and preferably for an additional time period sufficient for a substantial amount of any non-reacted antibody molecules to clear the body. The subject is then assayed for the presence and preferably location of any complex that formed.

2. Detection of huTFh in a Body Sample

Various heterogeneous and homogeneous assay protocols can be employed, either competitive or non-competitive for detecting the presence and preferably amount of huTFh in a body sample preferably a body fluid sample. For example, a liquid body fluid sample and labeled p26-49 are admixed with a solid support comprising antibody molecules produced by hybridoma TF8-5G9 or TF9-10H10 affixed to the inner wall of a microtiter plate well to form a solid-liquid phase immunoreaction admixture. The admixture is maintained under biological assay conditions for a time period sufficient for any huTFh present in the sample and labeled p26-49 to compete for binding to the antibody molecules present as solid support and form a solid phase immunoreaction product. The unbound labeled p26-49 is then separated from the immunoreaction products. The amount of labeled p26-49 bound as immunoreaction product is then determined, and thereby provides, by difference, a measure of the presence of huTFh.

EXAMPLES

The following examples are intended to illustrate, but not limit, the present invention.

1. Preparation of Tissue Factor-Containing Human Brain-Extract

Normal human brains obtained at autopsy were either processed within 12 hours or stored frozen at minus 80 degrees Centigrade (C). The meninges and cerebellum were removed and the remaining brain portions were homogenized in an equal volume of cold (0 degrees C.) acetone using a Polytron homogenizer (Brinkman Instruments, Co., Westbury, N.Y.). The resulting homogenate was admixed with an additional 3 volumes of cold acetone, and the tissue-solids fraction was recovered by filtration using a sintered glass funnel. Acetone soluble material was extracted from the retained solids seven additional times, each by admixing with two volumes of cold acetone and subsequent filtration. After the final filtration, residual acetone was allowed to evaporate at atmospheric pressure from the retained solids overnight at about 20 degrees C.

The retained brain tissue-solids were then subjected to 5 extractions, each performed by admixing the solids with a 2:1 heptane:butanol solution at a ratio of 1 gram tissue-solids per 25 milliliter (ml) heptane:butanol, followed by filtration to recover the solids. After the final filtration the retained brain tissue-solids were again dried overnight at about 20 degrees C. under atmospheric pressure to form a delipidated brain tissue powder that was stored at minus 80 degrees C. until needed.

Twenty-five grams of the brain tissue power were subsequently admixed with 500 ml of TS/EDTA buffer [100 millimolar (mM) NaCl, 50 mM Tris-HCl (pH 7.5), 0.02% sodium azide, 5 mM ethylenediaminetetraacetic acid (EDTA), 0.1% (v/v) Triton X-100 (polyarylethylene 9 octyl phenyl ether)] and stirred overnight at 4 degrees C. The admixture was then centrifuged at 15,300×g for 1 hour. The resulting pellet was resuspended in 500 ml of Buffer A [100 mM NaCl, 50 mM Tris-HCl (pH 7 5), 0 02% sodium azide, 2% Triton X-100] to form a slurry. After stirring for 1 hour at room temperature, the slurry was centrifuged as described above. The resulting supernatant was recovered, lyophilized and subsequently solubilized in 100 ml of Buffer A to form a huTF-containing brain-extract solution.

2. Coagulation Assay to Measure huTF Procoagulant Activity huTF procoagulant activity was measured in a one stage coagulation assay performed with all reagents and admixtures maintained at 37 degrees C. A pool of normal human plasma was citrated by admixing 1 volume of plasma with 1 volume of a solution containing 20 mM sodium citrate dihydrate and 140 mM NaCl, pH 7.4. One hundred microliters of a sample containing huTF diluted in TBS/BSA solution (150 mM NaCl, 50 mM Tris-HCl, pH 7.5, 0.1% bovine serum albumin) was admixed with 100 ul of the citrated plasma. One hundred ul of a 25 mM $CaCl_2$ solution were then admixed to form a coagulation reaction admixture that was rocked gently until coagulation occurred. The time between the addition of $CaCl_2$ and clot formation was measured. A standard curve of huTF activity was then constructed by plotting dilution versus coagulation time in seconds. An exemplary standard curve is shown in FIG. 3.

3. Preparation of a Factor VII-Containing Solid Support for Affinity Isolation of huTF Human factor VII/VIIa was isolated as described by Fair, *Blood*, 62:784–91 (1983), which is hereby incorporated by reference. This isolated factor VII/VIIa was activated for coupling to an agarose solid matrix by dialyzing 5 milligrams (mg) against 0.1M 2-(N-Morpholino)ethanesulfonic acid (MES) (pH 6.5), overnight at 4 degrees C. Calcium chloride was added to a final concentration of 1 mM. factor VII/VIIa was then admixed with 4 mls of AffiGel-15 activated agarose beads (Biorad Laboratories, Richmond, Calif.) and the resulting coupling-reaction mixture was processed by rotation for 4 hours at 4 degrees C. according to the manufacturer's recommendations (Biorad).

Excess protein binding sites on the solid support were blocked by gently agitating the solid support in 0.1M glycine ethyl ester for one hour at room temperature. Thereafter, the solid support was washed sequentially on a sintered glass funnel with about 20 ml each of (1) Buffer A, (2) Buffer A containing 1M NaCl, (3) Buffer A containing 5 mM EDTA, and (4) Buffer A containing 1 mM $CaCl_2$. Excess liquid was then removed by vacuum to form a semi-dry particulate mass (cake).

4. Factor VII/VIIa-Affinity Isolation of huTF

Twenty ml of a solution containing 0.1M glycine ethyl ester and 0.1M MES, pH 6.5 was admixed with 22.5 ml of Affigel-15 agarose beads (Biorad) to form a coupling reaction admixture. The coupling reaction admixture was maintained at room temperature for 1 hour. The resulting conjugate was washed on a sintered glass funnel 4 times with 10 volumes of Buffer 1 filtered under vacuum to form a glycine ethyl ester-agarose cake.

Thirty mls of brain-extract solution prepared in Example 1 were dialyzed overnight at 4 degrees C. against 6 liters of Buffer A containing 1 mM calcium chloride. Dialyzed brain extract was admixed with the glycine ethyl ester-agarose cake to form a solid-liquid phase reaction admixture. After being maintained for 2 hours at room temperature with rotation, the solid and liquid phases were separated by filtration using a sintered glass funnel. The liquid phase was recovered and admixed with Trasylol (aprotinin; Sigma Chemical Co. St. Louis, Mo.) to a final concentration of 10 units per ml. The recovered liquid phase was admixed with the factor VII/VIIa/agarose cake prepared in Example 3 to form a second solid/liquid phase admixture.

This admixture was maintained overnight at 4 degrees C. with rotation to allow formation of a huTF-factor VII/VIIa-containing solid phase product. The solid and liquid phases were then separated by filtration as previously described. The solid phase retained on the sintered glass funnel was washed with 25 mls of Buffer A containing 1 mM calcium chloride. The solid phase was then transferred to a sintered glass chromatography column (0.5×15 cm; Biorad) and washed with 6 mls of the same wash buffer. Any huTF bound to the solid support after the above washes was then released (eluted) by washing the solid support while retained upon the sintered glass column Buffer A containing 5 mM EDTA. Eluted material was collected in 1 ml fractions and each fraction was assayed for the presence of huTF as described in Example 2. huTF-containing fractions were pooled and dialyzed overnight against 6 liters of TBS (150 mM NaCl, 50 mM Tris-HCl, pH 7.5) containing 1% Triton X-100 (TBS/Triton) at 4 degrees C.

The dialysate thus formed was subsequently admixed with four volumes of cold acetone to precipitate the huTF protein. The precipitate was the collected by centrifugation at 5,000 times g for 30 minutes at approximately minus 10 degrees C. The resulting pellet was dried under nitrogen. Typical yields were 2 ug of huTF per gram (dry weight) of delipidated brain tissue powder.

A sample of the isolated huTF thus formed was suspended in TBS/Triton and then labeled with $Na^{125}I$ (16 micro Curies per microgram, Amersham, 125 Arlington Heights, Ill.) using Iodogen according to the manufacturer's directions (Pierce Chemical Co., Rockford, Ill.). After labeling, excess unreacted $^{125}I$ was separated from the labeled huTF by desalting chromatography on Sephadex G25 (Pharmacia, Inc., Piscataway, N.J.) using TBS/Triton.

$^{125}I$-labeled huTF-containing samples were evaluated by sodium dodecyl sulfate-polyacrylamide gel electrophoresis (SDS-PAGE) according to Laemmli, *Nature*, 227:680–685 (1970). Dithiothreitol (DTT, Sigma) was included in the sample buffer at 100 mM for those samples evaluated under reducing conditions. Immunoprecipitations were performed by incubating overnight at 4 degrees C. $^{125}I$-huTF in 1% Triton X100, 50 mM Tris-HCl (pH 7.4), 150 mM NaCl with 1/10 volume of TF8-5G9 or PAb 100 (ATCC TIB 115; a hybridoma producing a SV40 large T antigen specific antibody used here as a negative control) hybridoma culture supernatant. Goat anti-mouse IgG immobilized on agarose beads (Sigma Chemical Co., St. Louis, Mo.) was then used to adsorb the primary immunoreaction products. The beads were washed extensively with the same buffer and the bound $^{125}I$-huTF was eluted by boiling for 5 minutes in sample buffer with or without DTT. Protein bands were visualized after SDS-PAGE by autofluorography.

When isolated huTF was radioiodinated, reduced with DTT, and analyzed by SDS-PAGE on 10% acrylamide gels, a single major band with an apparent molecular mass of 47 kDa was observed (FIG. 4). However, when unreduced huTF was similarly analyzed, two bands of approximately 58 and 47 kDa were observed in relatively equal abundance (FIG. 5, lane B), suggesting at least two different size forms.

Possible explanations for the two bands observed in the absence of reduction were that the larger, i.e. slower migrating band, could be more highly glycosylated, may possess additional unprocessed protein, or might be associated with additional, disulfide-bond linked polypeptides. The presence of a single band following reduction was inconsistent with the first two suggestions. The latter possibility appeared most likely, but because of the small size difference, additional polypeptide chains would probably be small enough to migrate at or near the dye front and not be resolved by 10% acrylamide gels following reduction. Electrophoresis of reduced and non-reduced huTF on 15% polyacrylamide gels failed to show a single discrete light chain, although several minor, rapidly migrating bands were observed (FIG. 5, lanes A and B). These small, minor polypeptides could represent contaminants which have previously been noted [Broze et al., *J. Biol. Chem.*, 260:10917–20 (1985) and Guha et al., *Proc. Natl. Acad. Sci. USA* 83:299–302 (1986)]. To clearly resolve the possibilities, the 47 kDa and 58 kDa bands were excised from the non-reduced gel, and each was reduced with dithiothreitol and individually subjected to SDS-PAGE on a 15% acrylamide gel (FIG. 5, lanes C and D). The 58 kDa protein was resolved as a 12.5 kDa light chain and a 47 kDa heavy chain. When the 47 kDa protein was examined, only a heavy chain of the same molecular weight was observed. Thus both forms possessed heavy chains of similar behavior on SDS-PAGE.

Figure 6:
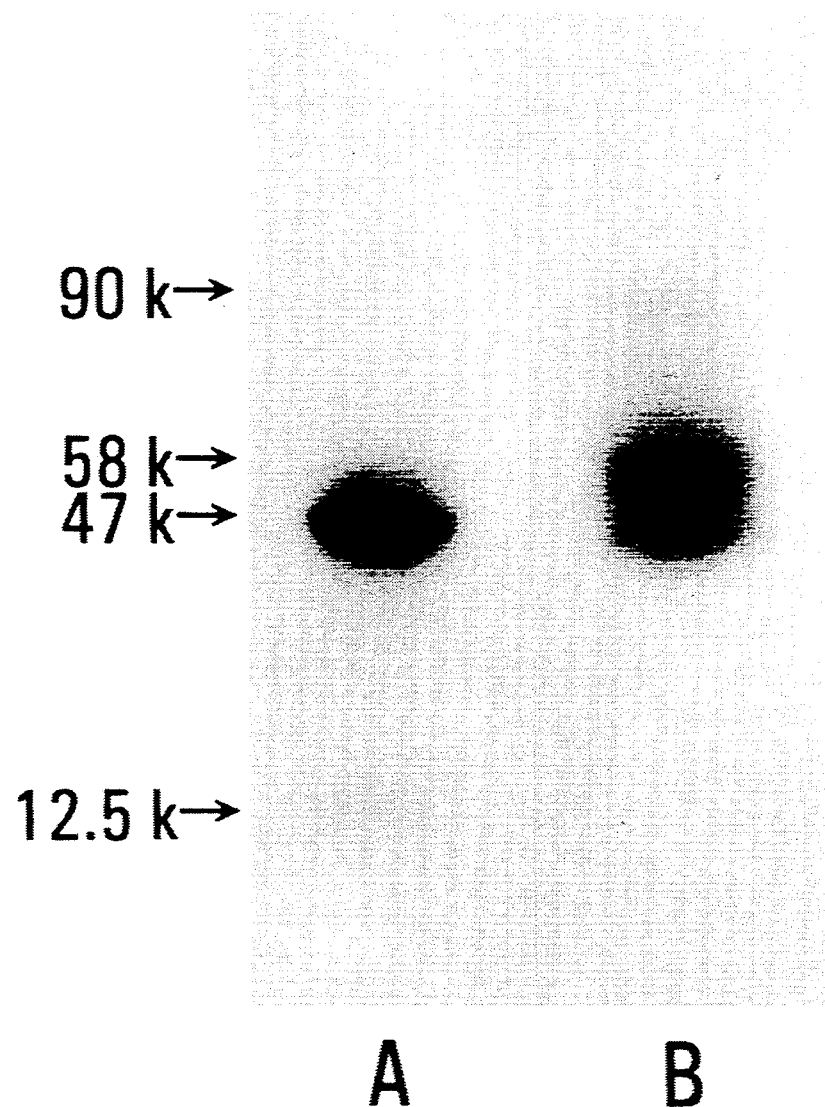

In order to demonstrate the presence of the light chain directly, $^{125}I$-huTF was immunoprecipitated with the huTF-specific monoclonal antibody TF8-5G9 and subjected to electrophoresis in the presence of reducing agent. The major 47 kDa band was observed along with a discrete band of approximately 12.5 kDa (FIG. 6, lane A). Electrophoresis of the sample without prior reduction yielded bands of approximately 47 kDa and 58 kDa, but no low molecular weight polypeptide (FIG. 6, lane B). Electrophoresis of non-reduced huTF also yielded minor quantities of 90 kDa protein, consistent with a dimer of the huTF heavy chain which has been suggested by Broze et al., *J. Biol. Chem.*, 260:10917–20 (1985).

To investigate the possibility that the huTF light chain might be derived proteolytically from the heavy chain the SDS-PAGE isolated light and heavy chains were subjected to N-terminal amino acid-sequence analysis.

Heavy and light chains were resolved on SDS-PAGE and electroblotted onto activated, aminoderivatized fiberglass filters using the high pH method of Abersold et al., *J. Biol. Chem.*, 261:4229–4238 (1986). The protein bands were visualized on the blots by fluorescent staining Abersold et al., supra, excised, and sequenced, still bound to the fiberglass, in an Applied Biosystems 470A protein sequencer with on-line HPLC analysis of PTH derivatives. Alternatively, the protein bands were visualized on the gel by staining with Coomassie blue and electroeluted for sequencing. Both methods gave equivalent results.

Microsequencing of the huTF heavy chain consistently resulting in two simultaneous amino acid sequences in roughly equimolar amounts. In almost all cases, each amino acid residue appeared twice, two cycles apart. This is clear evidence for staggered N-termini of two variants of huTF heavy chain, which differ in length at the N-terminus by two residues. The N-terminus of the larger variant was deduced to be Ser-Gly-X-X-Asn-Thr-Val-Ala-Ala-Tyr-X-Leu-Thr-Trp-Lys-Ser, wherein X represents an unspecified amino acid residue.

Several attempts to sequence the light chain yielded no sequence information, consistent with a blocked N-terminus. However, the heavy and light chain of huTF are antigenically distinct, since two rabbit anti-huTF antisera and twenty-eight murine monoclonal antibodies raised against isolated huTFh were all found to bind to the heavy chain alone. Therefore, the light chain is unlikely to be a proteolytic fragment of the heavy chain. In addition, the light chain did not react with antisera to beta-2 microglobulin.

The significance of the 12.5 kDa huTF light chain is presently unknown. It is unlikely to be derived artifactually during isolation by random disulfide exchange, since it is a single, discrete molecular species. When affinity isolated huTF was subjected to SDS-PAGE without reduction, huTF activity was eluted from gels corresponding to both the 58 kDa and 47 kDa molecular weight forms. huTF activity corresponding to those two molecular weight forms was also detected when crude brain or partially isolated placental extracts were subjected to electrophoresis on SDS gels (data not shown). In all cases the activity was factor VII-dependent, thus indicating huTF specific activity. These findings indicate that huTFh alone can activate factor VII and that the light chain is not required for this function.

It is of interest that the light chain is disulfide-bonded to only about half of the huTF heavy chains. Either it is absent in vivo from a significant proportion of huTF or is present, but associated via non-covalent interactions that are disruptible by detergents. The light chain of huTF may have gone unnoticed in earlier studies because its small size would result in migration at the dye front in SDS-PAGE, and because published analyses of huTF have been performed following reduction. The limited quantities which can be isolated using current affinity methods makes it difficult to detect an associated small polypeptide chain by protein staining.

Although monomeric huTF will initiate coagulation in vitro, physiologic initiation of coagulation by huTF occurs on cell surfaces. One may speculate that the light chain may play more subtle roles in huTF function or organization than can be detected in a straightforward coagulation assay. For example, the light chain may be involved in the assembly of the two-subunit receptor for factor VII which has been hypothesized to explain the apparent positive cooperactivity of binding of factor VII/VIIa to tissue factor. Alternatively, organization of huTF in structural domains on the cell surface and regulation of huTF activity on cell surfaces may be mediated by the huTF light chain molecule.

The role of N-linked oligosaccharides was examined by deglycosylating a sample of the $^{125}$I-huTF. About 12.74 nanograms (ng) of labeled huTF containing approximately $3.6 \times 10^5$ counts per minute (cpm) were admixed with 20 ul of a solution containing 0.4 units Glycopeptidase F (Boehringer-Mannheim Biochemicals, Indianapolis, Ind.), 20 mM Tris-HCl (pH 7.5), 10 mM EDTA, and 1% Triton X-100 and subsequently maintained for 16 hours at 37 degrees C. The deglycosylated products were then analyzed by SDS-PAGE as previously described.

The results of the deglycosylation studies, shown in FIG. 7, lanes 4 and 5, indicate that the 58 kDa form of huTF exhibits a higher relative molecular than the 47 kDa form because of the presence of addition protein moieties, i.e., the light chain.

The huTF thus isolated was relipidated to reconstitute its procoagulant activity. The tissue factor:lipid ratio necessary to provide a relipidated tissue factor product having maximal activity was empirically determined by dissolving the isolated huTF obtained above at various concentrations in HBS buffer solution (20 mM Hepes, pH 6.0, 140 mM NaCl, 0.01% sodium azide) containing 0.1% BSA. The various huTF dilutions were then relipidated as described below,and that ratio producing the highest recovered activity as determined in the coagulation assay described in Example 2 was then prepared for later use.

Lipids for relipidation of huTF were prepared by extracting them from rabbit brain acetone powder obtained from Sigma Chemical Co., St. Louis, Mo. The powder was admixed with heptane:butanol (2:1, v/v) at a ratio of 25 ml heptane-butanol per gram of powder, and the solids contained therein were recovered by filtration using a sintered glass funnel. This extraction process was repeated 6 times on the retained solids. The retained solids were then dried by roto-evaporation, dissolved in chloroform and stored at minus 80 degrees C. As needed, portions of the chloroform-dissolved solids were dried under nitrogen and dissolved to a concentration of 4 mg/ml in a solution of freshly prepared 0.25% sodium deoxycholate to form a rabbit brain phospholipids solution (RBPL).

For relipidation, 100 ul of each huTF dilution was admixed with 100 ul of RBPL solution, 0.76 ml of HBS solution containing 0.1% bovine serum albumin (HBS/BSA) and 40 ul of a 100 mM cadmium chloride solution. This admixture was maintained at 37 degrees C. for 2 hours and the activity of huTF contained therein was determined in the coagulation assay described in Example 2.

5. Production of Hybridomas and Monoclonal Antibodies

All hybridomas were produced using spleen cells from female Balb/c mice obtained from the Scripps Clinic and Research Institute vivarium ranging in age from 6 to 8 weeks, a. Mouse TF8 Immunization Five micrograms (ug) of affinity-isolated huTF prepared in Example 4 was dissolved in normal saline at 100 ug/ml, combined and subsequently emulsified at a 1:1 ratio (V/V) with R-700 adjuvant obtained from Ribi Immunochem Research, Inc., Hamilton, Mo. The emulsion was then injected subcutaneously (s.c.) into mouse TF8.

Mouse TF8 was similarly inoculated about two weeks later, using an emulsion containing denatured huTF and R-700 adjuvant. Denatured huTF was prepared by boiling for 5 minutes TBS [150 mM CaCl, 50 mM Tris-HCl (pH 7.5)] containing 0.09% Triton X-100 0.93% SDS, 0.2M 2-mercaptoethanol and huTF at 270 ug/ml. Thereafter the denatured huTF was admixed with an equal volume of normal saline containing 0.6 mg/ml mouse serum albumin. Subsequently, 4 volumes of acetone were admixed to the denatured huTF solution and the resulting admixture was maintained overnight at minus 20 degrees C. The resulting precipitate was collected by centrifugation at about 13,000 times g for 10 minutes, washed once with a 4:1 (V:V) acetone:H₂O solution and then suspended in 200 ul normal saline at a concentration of 0.1 mg/ml.

About four weeks after the initial injection, 33 ug of affinity isolated (non-denatured) huTF in 0.1 ml normal saline was admixed with 0.1 mls of Complete Freund's Adjuvant (CFA) to form an emulsion. This emulsion was then injected intraperitoneally (i.p.) into mouse TF8.

About eight weeks after the initial inoculation, 15 ug of affinity isolated huTF in phosphate buffered saline (PBS) was injected intravenously (i.v.) and an identical huTF/PBS inoculum was given i.v. twenty-four hours later. Mouse TF8's splenocytes were harvested for fusion three days later.

b. Mouse TF9 Immunization

Mouse TF9 was subjected to the same inoculation schedule as mouse TF8 except that both Ribi adjuvant injections utilized huTF that had been denatured prior to emulsification. In addition, the first PBS inoculum was administered i.p. and 4½ months after the CFA-containing inoculum.

c. Hybridoma Formation

The same fusion protocol was used for both TF8 and TF9 derived splenocytes. About $1 \times 10^8$ splenocytes from each mouse were admixed with $2 \times 10^7$ P3X63 Ag8.653.1 myeloma cells in 200 ul of a fusion medium comprising 30% w/v polyethylene glycol (PEG 4000, ATCC 25322-68-3). After cell fusion, the resulting hybridomas were seeded into 96 well plates, cultured in HAT medium (hypoxanthine, aminopterin and thymidine), and subsequently screened for the ability to produce antibody molecule that reacts with huTF.

Both mouse TF8 and TF9 spleen cell-derived fusions resulted in HAT medium resistant hybridoma cell clones. The TF8 fusion yielded 907 HAT resistant hybridomas whereas the TF9 fusion yielded 348 HAT resistant hybridomas.

6. Screening Hybridomas for Production of Anti-huTF Antibody Molecules a. Solid-Phase RIA

One hundred ul of goat anti-mouse IgG (Boehringer-Mannheim Biochemicals, Indianapolis, Ind.) diluted to 20 ug/ml in TBS were admixed into the wells of Immulon 96-well flexible vinyl microtiter plates (Dynatech Laboratories, Alexandria, Va.). The plates were then maintained for 1 hour at 37 degrees C. to allow the IgG to adsorb onto the walls of the wells. After washing three times with TBS, 100 ul of TBS/Triton containing 3% ovalbumin was admixed into each well to block excess protein binding sites.

The wells were maintained for 1 hour at about 20 degrees C. and then the blocking solution was removed by aspiration. Fifty ul of hybridoma culture supernate was admixed into each well. The resulting solid-liquid phase immunoreaction admixture was maintained at 37 degrees C. for 1 hour. The wells were then rinsed three times with TBS and excess liquid was removed by aspiration.

Fifty ul of $^{125}$I-labeled huTF prepared in Example 4 and containing approximately 1 ng of huTF and approximately $5 \times 10^5$ cpm in TBS/Triton was admixed into each well to form a second solid-liquid phase immunoreaction admixture. The wells were maintained for 2 hours at 37 degrees C. and then rinsed three times with TBS/Triton to isolate the solid-phase bound $^{125}$I-huTF-containing immunoreaction products. Excess liquid was removed by aspiration and the wells were allowed to dry. Individual wells were cut apart and the $^{125}$I contained in each well was determined with a gamma counter.

Background radioactivity (no reaction of huTF with antibody) averaged about 200-300 cpm per well, while positive reactions of huTF with antibody yielded 10000 cpm per well. Hybridomas assayed as positive for the production of anti-huTF antibodies were selected and constitute hybridomas of the present invention. Subsequently, those hybridomas were screened in the dot blot assay described below.

b. Dot Blot ELISA

Acetone precipitated huTF prepared in Example 4 was extracted twice with a 4:1 (V/V)-acetone:H₂O solution. The precipitate that remained was resuspended at 20 ug/ml in TBS. Twenty ng (1 ul) of this huTF solution was spotted onto BA83 nitrocellulose paper (Schleicher and Schuell, Keene, N.H.) next to a number written on the paper in indelible ink. The spotted huTF was air dried and individual spots were then cut out into paper circles using a punch. Individual paper circles were immersed into individual wells of a multi-well tray containing BLOTTO, [5% w/v nonfat dry milk, 0.01% Antifoam A (Sigma) and 0.0001% merthiolate in PBS; Johnson et al., *Gene. Anal. Tech.*, 1:3 (1984)], and were maintained at 37 degrees C. for about 1 hour.

The BLOTTO was removed from the wells by aspiration and 200 ul of hybridoma culture supernate was added to each well. The wells were then maintained at 37 degrees C. for 2 hours. The paper circles were rinsed twice with TBS, removed from the wells and combined into a single larger container for an additional rinse in TBS. Excess liquid was then removed from the container.

Alkaline phosphatase-conjugated anti-mouse IgG in the protoblot reagent kit (Promega Biotech, Ann Arbor, Mich.) was diluted 1:5700 in BLOTTO and contacted with the paper circles. The Protoblot solution was maintained in contact at 37 degrees C. for 30 minutes. The paper circles were then rinsed three times in TBS. Bound alkaline phosphatase was detected on the paper circles using the chromogenic substrates supplied in the Protoblot kit according to the manufacturer's instructions.

c. Western Blot Assay

For Western blot assays, about 10 ug of huTF isolated as described in Example 4 was dissolved in sample buffer (2% SDS, 50 mM dithiothreitol, 10% glycerol, 125 mM Tris-HCl ph 6.8) and boiled for 5 minutes. It was then subjected to SDS-polyacrylamide gel electrophoresis on a preparative-style slab gel as described by Laemmli, *Nature*, 226:680 (1970), which methods are hereby incorporated by reference, in a wide lane flanked on either side by small lanes containing pre-stained molecular weight standards (Diversified Biotech, Newton Centre, Mass.). After electrophoresis and electroblotting onto nitrocellulose, as described by Towbin et al., *Proc. Natl. Acad. Sci. USA*, 76:4350 (1979) which methods are hereby incorporated by reference, the blot was blocked with a solution of 5% powdered nonfat milk in TBS and clamped into a manifold (Miniblotter; Immunetics, Cambridge, Mass.). Pools of eight hybridoma cell culture supernatants were loaded into each manifold slot and incubated for 1 hour at 37° C., after which the blot was removed and rinsed with TBA (TBS containing 0.02% sodium azide). Lanes which had bound antibody were visualized using an alkaline phosphatase-conjugated second antibody developed with a chromogenic substrate (Protoblot; Promega Biotech, Madison, Wis.) according to the manufacturer's suggested methods. Culture supernatants from positive pools were retested singly at ⅛ dilution in 5% powdered nonfat milk TBA to identify individual hybridoma clones that produce anti-TF antibodies.

Hybridomas determined to be positive for the production of anti-huTF antibodies were selected for further characterization. For example, hybridomas derived from the above TF8 fusion were characterized as anti-huTF antibody producing hybridoma cultures if the hybridoma culture supernatants demonstrated immunoreaction with huTF in the dot blot assay described in Example 6b and the solid phase RIA described in Example 6a. These characterization yielded 4 TF8 hybridoma cell lines as shown in Table 5 in Example 13.

Hybridomas derived from the TF9 fusion were characterized as anti-huTF antibody producing hybridoma cultures if the hybridoma culture supernatants demonstrated immunoreaction with huTF in the solid phase RIA described in Example 6a and in the Western blot assay described in Example 6c. These characterizations yielded 24 TF9 hybridoma cell lines, most of which are shown in Table 5 in Example 13.

Antibody molecules produced by a particular hybridoma selected by the foregoing screening methods are referred herein by characters that indicate 1) the immunized mouse (i.e., TF8 or TF9) that donated spleen cells to a particular fusion, and 2) the 96 well culture plate, row and well number from which the particular HAT medium resistant hybridoma cell was isolated (i.e., 5B7, 11D12, etc.). The specific referring character can be listed herein as one word, as a hyphenated words or as two words. For example, the following characters refer to the same monoclonal antibody molecule composition: TF8-5G9, TF85G9, and TF8 5G9.

7. Isolation of Immunoglobulin IgG

Immunoglobulin IgG was isolated from the ascites fluid of a mouse containing the mouse hybridoma cell line TF8-5G9 (ATCC number HB9382) using a Biorad Laboratories MAPS II system according to the manufacturer's instructions. The protein concentration of the isolated IgG was determined using the BCA Protein Assay Reagent (Pierce Chemical Co.) according to manufacturer's specifications.

8. Preparation of an Anti-huTF-Containing Solid Support for Immunoaffinity Isolation of huTF Anti-huTF antibodies were activated for coupling to an agarose solid matrix by dialyzing 10 mg of MAPS-isolated TF8-5G9 monoclonal antibody, prepared as described in Example 7, against 500 ml of a dialysis buffer consisting of 0.1M MES, pH 6.5, for 16 hours at 4 degrees C. with at least one change of the dialysis buffer. The activated TF8-5G9 antibodies were then admixed with 2 ml of AffiGel-10 agarose beads (Biorad) and the resulting coupling-reaction admixture was processed according to the manufacturer's instructions to form a TF8-5G9/agarose solid support.

Excess protein binding sites on the solid support were then blocked, washed and vacuum filtered as described in Example 3 to form TF8-5G9/agarose cake.

9. Immunoaffinity Isolation of huTF

Brain-extract solution equivalent to about one-half of a human brain, i.e., about 100 mls, and prepared in Example 1 was dialyzed over three days with two changes against a total of 6 liters of Buffer A at 4 degrees C. The dialyzed brain-extract was then centrifuged at 10,000×g for 1.5 hours. The resulting supernatant was admixed with the glycine ethyl ester-agarose cake prepared in Example 4 to form a solid-liquid phase reaction admixture. After being maintained for 2 hours at room temperature with rotation, the solid and liquid phases were separated by filtration using a sintered glass funnel. The huTF-containing liquid phase was recovered and admixed with the TF8-5G9/agarose cake prepared in Example 8 to form a solid/liquid phase immunoreaction admixture.

The immunoreaction admixture was maintained overnight at 4 degrees C. with rotation to allow formation of a tissue factor-containing solid phase immunoreaction product. The solid and liquid phases were then separated by filtration as previously described. The solid phase was retained and then washed with 10 volumes of Buffer A. The solid phase was then transferred to a glass chromatography column and washed sequentially with (1) 2 volumes of 1M NaCl containing 1% Triton X-100, and (2) 2 volumes of 0.1M glycine pH 4.0 containing 1% Triton X-100.

Any huTF immunologically bound to the solid support after the above washes was then released (eluted) by washing the solid support while retained upon a sintered glass funnel with 20 mls of 0.1M glycine, pH 2.5, and 1% Triton X-100. Eluted material was then collected, assayed for huTF, pooled and dialyzed, all as described in Example 4.

The dialysate was subsequently admixed with four volumes of cold acetone to precipitate the huTF protein. The precipitate was then collected by centrifugation at 5,000 times g for 30 minutes at approximately −10 degrees C. The resulting pellet was dried under nitrogen and a portion of the pellet was analyzed by SDS-polyacrylamide gel electrophoresis (SDS-PAGE) under denaturing conditions.

The results of that analysis, shown in FIG. 8, indicate that huTFh can be immunoaffinity isolated with a yield of 33 mg of huTFh per gram of delipidated brain powder.

10. Inhibition of Coagulation by Anti-huTF Antibodies

Ten microliters of a hybridoma culture supernatant were admixed with 90 ul of HBS/BSA containing about 2 ng of the relipidated huTF prepared in Example 4. The immunoreaction admixtures thus formed were maintained at 37 degrees C. for 30 minutes to allow the anti-huTF antibody molecules to immunologically bind the huTF and form an immunoreaction product. The immunoreaction admixtures were subsequently assayed for huTF procoagulant activity as described in Example 2. An irrelevant IgG preparation was used in place of anti-huTF antibody as a negative control.

An effective huTF concentration was extrapolated from the standard curve produced as in Example 2 using the clotting time measured in the presence of inhibitor. Inhibition was expressed as a percent ratio of the effective huTF concentration over the actual huTF concentration used. Monoclonal antibody molecule preparations producing at least 50 percent inhibition were selected as neutralizing antibody molecule compositions of the present invention.

Numerous culture supernatants from hybridomas raised against isolated huTF as described in Example 5 were measured by the above procedure for their ability to inhibit initiation of coagulation. Those hybridomas found to significantly inhibit initiation of coagulation are identified in Table 5.

Inhibition of coagulation by anti-huTF antibodies has also been accomplished using preformed huTF-factor VII complexes. Ten ul containing about 1 ng of relipidated huTF prepared in Example 4 were admixed with 70 ul of HBS/BSA, 10 ul 20 mM calcium chloride and, where indicated, 10 ul containing about 25 ng of factor VII prepared as described in Example 3. This admixture was maintained at 37 degrees C. for 15 minutes to allow huTF to form a complex with any factor VII available in the admixture. Thereafter 10 ul of solution was further admixed containing about 10 ng of MAPS-isolated monoclonal antibody prepared as described in Example 7, and this second admixture was maintained at 37 degrees C. for 30 minutes. Inhibition of coagulation was then measured in the resulting admixture by adding first 100 ul of 20 mM calcium chloride followed by 100 ul of either human citrated plasma or factor VII depleted plasma prepared as described in Example 12 and observing the clotting time in seconds. Percent inhibition was expressed as described in Example 10, and the results of these inhibitions with preformed huTF-factor VII complex is shown in Table 2A.

TABLE 2A

Inhibition of huTF-Factor VII-Initiated Coagulation by Anti-huTF Antibodies

| Antibody | Factor VII[d] | Percent Inhibition |
|---|---|---|
| I. Coagulation with Citrated Human Plasma | | |
| Blank[a] | + | 0 |
| TF85G9[b] | + | 58% |
| Control[c] | + | 0 |
| TF85G9 | − | 83% |
| Control | − | 0 |
| II. Coagulation with Factor VII Depleted Human Plasma | | |
| Blank | + | 0 |
| TF85G9 | + | 58% |
| Control | + | 0 |

[a]"Blank" indicates that no monoclonal antibody was used in the assay.
[b]"TF85G9" indicates that the monoclonal antibody isolated from hybridoma TF8-5G9 was the antibody used in the assay.
[c]"Control" indicates that an irrelevant monoclonal antibody was the antibody used in the assay.
[d]"+" indicates that factor VII was added and allowed to form a complex with purified huTF before antibody was added to the mixture.

Additional studies of inhibition of coagulation by anti-huTF antibodies has been carried out under conditions that compare inhibition before and after TF has associated with factor VII/VIIa to form a TF:factor VII/VIIa complex.

In these studies inhibition of coagulation by anti-huTFh antibodies using preformed TF:VII/VIIa complexes was accomplished essentially as described above in Example 10 except that the 10 ul monoclonal antibody-containing solution utilized was hybridoma culture supernatant instead of a MAPS-isolated monoclonal antibody-containing solution. In comparison, inhibition of coagulation by anti-huTF antibodies was assessed by forming immunocomplexes between those antibodies and relipidated huTF before admixture with citrated plasma containing factor VII/VIIa as described above in Example 10.

Although all the antibodies presently described were examined in this comparative inhibition assay, only those that exhibited greater than about sixty percent (60%) inhibition were considered significant for an ability to inhibit coagulation initiated by a huTF:VII/VIIa complex. Those MoAbs are TF9-1B8, TF9-5B7, TF8-5C4, TF8-11D12, and TF8-21F2.

11. Polypeptide Synthesis

The polypeptides corresponding to the various huTFh regions utilized herein were chemically synthesized on an Applied Biosystems Model 430A Peptide Synthesizer using the symmetrical anhydride method of Hagenmaier, et al., *Hoppe-Seyler's Z. Physiol. Chem.*, 353:1973 (1982). In addition to the polypeptides listed in Tables 1 and 2, the polypeptides listed in Table 3 below were also synthesized and comprise polypeptides of the present invention useful for the production of anti-polypeptide antibodies capable of reacting with huTFh.

TABLE 3

Antigenic Polypeptides

| | |
|---|---|
| p121-155 | H—TKVNVTVEDERTLVRRNNTFLSLRDVFGKDLIYTL—OH |
| p204-226 | H—DSPVECMGQEKGEFREIFYIIGA—OH |
| p225-244 | H—GAVVFVVIILVIILAISLHK—OH |
| p245-263 | H—CRKAGVGQSWKENSPLNVS—OH |

12. Inhibition of Coagulation by Polypeptides

The ability of the polypeptides of the present invention to inhibit huTF-initiated coagulation were assayed by first incubating the polypeptides in the presence of factor VII/VIIa and calcium ions, and then adding this mixture to factor VII/VIIa-deficient plasma and evaluating clotting times.

Human factor VII/VIIa was isolated as described in Example 3. Ten microliters of a solution of 200 ng of this isolated factor VII/VIIa per ml of HBS/BSA was added to a solution comprising 100 ul of HBS, 20 ul of 25 mM $CaCl_2$, and with 100 ul of TBS/Triton containing synthetic polypeptide. Numerous admixtures were so prepared which contained varying concentrations of the polypeptide and were then maintained at 37 degrees C. for 15 minutes. Relipidated tissue factor prepared as described in Example 4 was diluted in HBS/BSA such that 10 ul would yield a coagulation time of approximately 45 seconds when tested in the coagulation assay described in Example 2. The above maintained admixture was further admixed with this 10 ul dilution of relipidated huTF, with 100 ul of 25 mM $CaCl_2$, and with 100 ul of factor VII/VIIa-deficient plasma (George King Bio-Medical, Inc., Overland Park, Kans.) diluted 1 part plasma to 1.5 parts HBS. The clotting time was then determined and plotted as described in Example 2. A prolongation of clotting time was taken to indicate inhibition of coagulation by the synthetic polypeptide. Percent inhibition was calculated as described in Example 10. Polypeptides producing at least a 30% inhibition of coagulation were considered huTFh binding site polypeptide analogs, i.e., polypeptides p26-49, p146-167 and p161-189 as shown in section I of Table 4.

Alternatively, factor VII/VIIa-deficient plasma has been used in the above inhibition assay prepared from plasma that was depleted of factor VII/VIIa by immunoaffinity adsorption with monoclonal antibodies. A monoclonal antibody to human factor VII/VIIa was prepared essentially as described in Example 5, except that factor VII/VIIa isolated as described in Example 3 was used as immunogen in place of huTF. The resulting hybridomas were evaluated by ELISA to identify a hybridoma that does not react with the human blood proteins Protein S, factor IX, factor X and factor II, available from Enzyme Research Laboratories, Inc., South Bend, Ind. Such a hybridoma FV11.F1.2H3-3.2, is available from Dr. T. S. Edgington (Scripps Clinic and Research Foundation, La Jolla, Calif.). Immunoglobulin IgG was isolated from ascites of a mouse containing hybridoma FV11 F1.2H3-3.2 and the isolated IgG was conjugated to a solid support as described in Example 8. The resulting anti-factor VII/VIIa monoclonal antibody-containing solid support was used to deplete factor VII/VIIa from pooled, normal citrated plasma using the immunoaffinity procedure described in Example 9 except that the liquid-phase containing plasma was collected and retained.

The ability of some of the polypeptides to competitively inhibit coagulation when used in lipidated form was assessed in the above assay by substituting 100 ul of lipidated synthetic polypeptide in place of the 100 ul solution of synthetic polypeptide.

Lipidated synthetic peptides were prepared in the manner described in Example 4 for relipidation of isolated huTF except that synthetic polypeptide was substituted for isolated huTF. The ratio 52 to 1 of lipid to polypeptide (w/w) was routinely utilized. Lipidated polypeptides producing at least 30% inhibition of coagulation were considered huTFh binding site polypeptide analogs, when present in lipidated form, i.e., those polypeptides shown in section II of Table 4.

TABLE 4

Inhibition of huTF-Initiated Coagulation by Polypeptide Analogues of huTFh

| Peptide | Inhibition[a] | Concentration |
|---|---|---|
| I. Non-Phospholipidated Peptides | | |
| p1-30 | 25.0 | 10 μM |
| p26-49 | 88.8 | 10 μM |
| p41-71 | 25.0 | 10 μM |
| p40-49 | 25.0 | 10 μM |
| p56-71 | 25.0 | 10 μM |
| p72-104 | 25.0 | 10 μM |
| p94-123 | 20.0 | 10 μM |
| p121-155 | 10.0 | 10 μM |
| p146-167 | 87.5 | 10 μM |
| p161-189 | 32.5 | 10 μM |
| p190-209 | 20.0 | 10 μM |
| p204-226 | 20.0 | 10 μM |
| None | 0 | — |
| II. Phospholipidated Peptides | | |
| p1-30 | 81.0 | 10 μM |
| p26-40 | 83.0 | 10 μM |
| p40-71 | 65.0 | 10 μM |
| p50-71 | 73.3 | 30 μM |
| p94-123 | 93.7 | 10 μM |
| p121-155 | 55.0 | 10 μM |
| p146-167 | 80.0 | 10 μM |
| p161-189 | 94.0 | 10 μM |

[a]Percent Inhibitions determined as described in Example 12.

Exemplary dose-response curves obtained while performing the above polypeptide inhibition studies are shown in FIGS. 9 and 10.

13. Inhibition of Antibody-huTF Immunoreaction by Polypeptides

The wells of Immulon U-bottom 96-well plates made of flexible vinyl (Dynatech) were coated with goat anti-mouse IgG (Boehringer-Mannheim) as described in Example 6 except that blocking of excess protein binding sites was performed for 20 minutes at 37 degrees C.

Fifty ul of hybridoma culture supernatant were placed in each well and maintained for 1 hour at 37 degrees C. The wells were then rinsed three times with TBS and excess liquid was removed by aspiration.

Isolated huTF was prepared on immuno-affinity columns as described in Example 9. The resulting acetone precipitates containing isolated huTF were dissolved in TBS/Triton and the protein concentration was determined using the BCA Protein Assay Reagent (Pierce) according to manufacturer's specifications. Carbohydrate side groups on huTF were biotinylated using biotin-hydrazide (ICN Biomedicals Inc., Plainview, N.Y.) according to the methods described by O'Shannessy et al., *Immunol. Letters*, 8:273–277 (1984) forming a biotinylated huTF solution.

Fifty ul of biotinylated huTF solution prepared to 60 ng/ml of TBS/Triton was then placed in each well together with 5 uM synthetic polypeptide and maintained for 1 hour at 37 degrees C. The wells were then rinsed three times with TBS/Triton.

One hundred ul of streptavidin-conjugated alkaline phosphatase (Detek I-alk, Enzo Biochem Inc., New York, N.Y.) diluted 1/100 in TBS containing 5mM EDTA, 0.5% Triton X-100 and 1% BSA was placed into each well and maintained for 30 minutes at 37 degrees C. The wells were then rinsed four times with a solution containing 10 mM potassium phosphate (pH 6.5), 2% BSA, 0.5% Triton X-100, 0.5M sodium chloride and 1 mM EDTA, followed by a single rinse with detection buffer [0.1M Tris-HCl (pH 8.8), 0.1M NaCl, 5 mM MgCl$_2$].

One hundred ul of a solution containing 2 mM p-nitrophenyl phosphate in detection buffer was then added to each well and maintained for 1 hour at 37 degrees C. The optical absorbance at 405 nanometers (nm) was then measured for each well using a Bio-Tek microplate reader (Bio-Tek Instruments, Winooski, Vt.).

The results of the competitive inhibition study are shown in Table 5.

TABLE 5

Table of Peptide Interactions with Monoclonal Antibodies

| Mab[a] | | | | | | |
|---|---|---|---|---|---|---|
| TF85G9 | + | | | | | |
| TF811D12 | + | | | | | |
| TF85C4 | | | | + | | |
| TF821F2 | | | + | | | |
| TF91D5 | | | + | | + | + |
| TF92C4 | | + | + | | + | + |
| TF92F6 | | | | + | | + |
| TF95C7 | | + | + | | + | + |
| TF96B4 | | | + | | + | |
| TF99C3 | | + | + | | + | + |
| TF910C2 | | | + | | + | |
| TF91F1 | + | | | | | |
| TF91E7 | | | | + | + | + |
| TF91B8 | | + | | | + | + |
| TF91B9 | + | | | | | |

TABLE 5-continued

Table of Peptide Interactions with Monoclonal Antibodies

| Mab[a] | | | | | |
|---|---|---|---|---|---|
| TF94D11 | | + | + | + | |
| TF95G4 | | + | + | | |
| TF95B7 | + | + | | | |
| TF96G4 | | + | | | |
| TF97E10 | | + | | + | |
| TF98E8 | + | + | | + | |
| TF99E1 | + | + | + | | |
| TF99B4 | | + | + | | |
| TF96C8[b] | + | + | + | | |
| TF910H5[b] | | + | | + | |
| TF99D6[b] | | + | | + | |
| TF910 H10[b] | + | + | | + | |

[a] Each monoclonal antibody (Mab) was produced by a hybridoma having the same designation. All monoclonal antibodies were screened using hybridoma culture supernatants as described in Example 13.
[b] These antibodies were considered non-neutralizing according to results from Example 10; all other antibodies were considered neutralizing according to these same results.

Inhibition was considered significant if the measured absorbance value obtained in the presence of polypeptide was more than one standard deviation from the mean value obtained for a given antibody in the absence of polypeptide.

14. Detection of huTF in a Body Sample by Two-Site ELISA huTF can be detected in a body sample such as blood, plasma, saliva, urine, etc. by using two monoclonal antibodies that can concurrently bind the same huTF molecule.

Immulon polystyrene U-bottom 96-well plates (Dynatech) are coated with goat anti-mouse IgG (Boehringer-Mannheim) by first admixing into each well ul of the IgG diluted to 10 ug/ml in TBS and then maintaining the IgG solution in contact with the well overnight at 4 degrees C. The wells are rinsed three times with TBS and 100 ul of TBS/Triton containing 3% BSA is added to each well. The wells are then maintained for 1 hour at 37 degrees, rinsed three times with TBS and excess liquid is removed by aspiration.

One hundred ul of an anti-huTF antibody molecule-containing culture supernatant from a first hybridoma, TF9-6B4, is admixed in each well and maintained for 1 hour at 37 degrees C. The wells are then rinsed three times with TBS and excess liquid is removed by aspiration.

Immunoaffinity isolated and acetone precipitated huTF prepared as in Example 9 is dissolved in TBS/Triton. Dilutions of the huTF solution are prepared ranging from 5 ug/ml to 0.5 ng/ml of TBS/Triton and 100 ul of a dilution is placed in a well of the Immulon plate. The dilutions of huTF are maintained in contact with the first antibody for 1 hour at 37 degrees C. The dilutions are then removed and the wells were rinsed three times with TBS/Triton. Excess liquid is removed by aspiration.

Anti-huTF antibodies are MAPS-isolated from ascites of a second hybridoma, TF9-10H10, by the methods described in Example 7. The antibody solution that results is measured for protein and subsequently labeled by biotinylation as described in Example 13.

The biotinylated anti-huTF antibody is diluted to 60 ng/ml of TBS/Triton and 100 ul of this solution is admixed in each well. The wells are maintained at 37 degrees C. for 1 hour and then rinsed three times in TBS/Triton.

The bound biotinylated anti-huTF antibody is then detected using the Detek I-alk system described in Example 13. The monoclonal antibodies used as a first and second antibody in this assay can be varied, so long as the two have the ability to bind concurrently to huTF. For example, where TF9-6B4 has been utilized as a first antibody, TF9-11D12 may be utilized as a second antibody in place of TF9-10H10. Thus, this invention contemplates any combination of antibodies which can bind concurrently in this assay.

15. Construction of a DNA Segment Containing the Entire pre-huTFh Coding Sequence A DNA segment containing the entire pre-huTFh coding sequence can be constructed in the following manner using recombinant plasmids pCTF64, pCTF403 and pCTF314, whose restriction maps are shown in FIG. 11, and procedures that are well known in the art. See, for example, Maniatis et al., *Molecular Cloning: A Laboratory Manual*, Cold Spring Harbor Laboratories, Cold Spring Harbor, N.Y. (1983).

The insert segments contained within the recombinant DNA plasmids shown in FIG. 11 have the EcoRI linker 5'-GGAATTCC-3' (Collaborative Research, Lexington, Mass.) at each terminus to facilitate the cloning process. These linker sequences are not present in the nucleotide sequence shown in FIG. 2 as they are not a part of the naturally occurring huTFh DNA coding sequence. In order that the following descriptions of construction of recombinant DNA molecules be clear in regard to the huTFh DNA sequences involved, segments generated by digestions that include EcoRI termini and thus may contain these additional linker sequences will be referred to by the nucleotide base number shown in FIG. 2. It is understood that the segments may contain these additional sequences at their termini.

Plasmid pCTF64 is digested with the restriction endonucleases EcoRI and DraIII to produce a DNA segment including a nucleotide sequence corresponding to the sequence shown in FIG. 2 from base residue 1 to residue 296. The 302 nucleotide base pair (bp) segment so produced is isolated by size fractionation using an agarose gel and then dephosphorylated by treatment with alkaline phosphatase.

Plasmid pCTF403 is digested with the restriction endonuclease EcoRI to produce a DNA segment including a nucleotide sequence corresponding to the sequence shown in FIG. 2 from residue 776 to residue 1125. The resulting 352 bp segment is isolated by size fractionation using an agarose gel.

Plasmid pCTF314 is digested with the restriction endonuclease EcoRI and the resulting 647 bp segment is isolated by size fractionation. This segment includes a nucleotide sequence that corresponds to the sequence shown in FIG. 2 from residue 135 to residue 775. The 647 bp segment is isolated by size fractionation and dephosphorylated with alkaline phosphatase.

The 352 bp segment and the dephosphorylated 647 bp segment are then operatively linked (ligated) by reaction with T4 DNA ligase thus forming a 999 bp segment having a nucleotide sequence corresponding to the sequence shown in FIG. 2 from residue 135 to residue 1125. The 999 bp segment is then digested with the restriction endonuclease DraIII cleaving the 999 bp segment at a position between base residues 296 and 297 shown in FIG. 2, thereby generating a 168 bp segment and a 831 bp segment. The dephosphorylated 302 bp segment and the 831 bp segment are then operatively linked using T4 DNA ligase to form an 1125 bp segment including a nucleotide sequence corresponding to the sequence shown in FIG. 2 from residue 1 to residue 1125.

The cloning plasmid vector pUC8 is linearized by digestion with EcoRI. The above prepared 1133 bp segment and the EcoRI digested vector are operatively linked using T4 DNA ligase to form the circular recombinant DNA molecule pUC-pre-huTFh.

*E. coli* strain RR1 (Bethesda Research Laboratories, Gaithersburg, Md.) is transformed with pUC-pre-huTFh and successful transformants are selected on the basis of ampicillin resistance. The selected transformants are then cloned and screened for the presence of a recombinant DNA molecule having the pre-huTFh structural gene.

Screening for the presence of recombinant DNA molecules having the pre-huTFh structural gene is accomplished by digesting the rDNA from each selected transformant with EcoRI. The resulting EcoRI fragments are resolved into a pattern according to size on an agarose gel. Recombinant DNA molecules producing a three band pattern corresponding to DNA segments of 352 bp, 781 bp and 2682 bp contain the pre-huTFh structural gene. *E. coli* RR1 transformants having rDNA producing the above described EcoRI digestion pattern contain a recombinant DNA molecule of the present invention and are selected (recovered).

A DNA segment containing a substantial portion of the pre-huTFh coding sequence including the extracellular anchor region but lacking the transmembrane anchor region at the carboxy terminus and thereby coding for a soluble huTFh protein is constructed in the following manner.

Plasmid pCTF64 is digested with the restriction endonuclease EcoRI to produce a DNA segment including a nucleotide sequence corresponding to the sequence shown in FIG. 2 from residue 1 to residue 486. The 486 nucleotide base pair (bp) segment so produced is isolated by size fractionation using an agarose gel and then dephosphorylated by treatment with alkaline phosphatase. The dephosphorylated 486 bp segment is then digested with the restriction endonuclease DraIII cleaving the 486 bp segment at a position between base residue 296 and 297 shown in FIG. 2, thereby generating a 296 bp segment and a 190 bp segment. The 296 bp segment is isolated by size fractionation using an agarose gel.

Plasmid pCTF314 is digested with the restriction endonuclease EcoRI to produce a DNA segment including a nucleotide sequence corresponding to the sequence shown in FIG. 2 from residue 135 to residue 775. The resulting 641 bp segment is isolated by size fractionation using an agarose gel and then dephosphorylated by treatment with alkaline phosphatase. The dephosphorylated 641 bp segment is then digested with DraIII cleaving the 641 bp segment at a position between base residue 296 and 297 shown in FIG. 2, thereby generating a 162 bp segment and a 479 bp segment. The 479 bp segment is isolated by size fractionation using an agarose gel.

The above prepared segments of 296 bp and 479 bp are then operatively linked (ligated) by reaction with T4 DNA ligase thus forming a 775 bp segment having a nucleotide adapter sequence corresponding to the sequence shown in FIG. 2 from residue 1 to residue 775.

The cloning plasmid vector pUC18 is linearized by digestion with EcoRI. The above prepared 775 bp segment and the EcoRI digested vector are operatively linked using T4 DNA ligase to form the circular recombinant DNA molecule pUC-pre-huTFh-T.

*E. coli* RR1 is transformed with pUC-pre-huTFh-T and ampicillin resistant transformants, i.e., clones containing pUC-pre-huTFh-T, are selected.

Recombinant DNA molecule pUC-pre-huTFh-T is digested with EcoRI and the resulting 775 bp segment is isolated by size fractionation.

Synthetic oligonucleotide adapter segments having the sequences:

5'-AATTTAGAGAATAAGAATTCGGG-3', and

3'-ATCTCTTATTCTTAAGCCC-5' are produced according to the methods of Caruthers et al., *J. Am. Chem. Sock*, 103:3185 (1981), and Gait et al., *Cold Spring Harbor Symp Quant. Biol.*, 47:393 (1983) except that the oligonucleotides so prepared are not phosphorylated with polynucleotide kinase so as to prevent operative linkage (ligation) of these oligonucleotides to one another. The oligonucleotides are annealed to form a double-stranded DNA linker segment containing a cohesive EcoRI terminus and a blunt terminus according to the methods of Rotherstein et al., *Methods in Enzymol.*, 68:98 (1979). This linker segment is then operatively linked to the 775 bp segment obtained from pUC-pre-huTFh-T to form a 817 bp segment containing one annealed segment at each end of the 775 bp segment. The resulting 817 bp segment is then digested with EcoRI to convert each termini of the 817 bp segment from blunt to EcoRI cohesive, forming a 805 bp segment. The resulting 805 bp segment is isolated by size fractionation using an agarose gel.

The cloning plasmid vector pUC18 is linearized by digestion with EcoRI. The above prepared 805 bp segment and the EcoRI digested vector are operatively linked using T4 DNA ligase to form the circular recombinant DNA molecule pUC-pre-huTFh-TR.

*E. coli* RR1 is transformed with pUC-pre-huTFh-TR and ampicillin resistant transformants, i.e., clones containing pUC-pre-huTFh-TR, are selected.

16. Production of huTFh by Expression of Recombinant huTFh Coding Sequences

The expression of recombinant huTFh from recombinant DNA molecules may be accomplished in a variety of expression media including procaryotic bacterial cells, non-vertebrate eucaryotic cells and higher (vertebrate) eucaryotic cells. Exemplary of such expression media are *E. coli*, *S. cerevisiae* and Chinese hamster ovary (CHO) cells, respectively.

a. Expression of pre-huTFh in *E. coli*

A recombinant DNA molecule capable of expressing the pre-huTFh structural gene in *E. coli* cells can be constructed by isolating a pre-huTFh gene-containing DNA segment from the pUC-pre-huTFh recombinant DNA molecule produced in Example 15 and operatively linking that segment to a procaryotic expression vector.

Recombinant DNA molecule pUC-pre-huTFh is digested with EcoRI under conditions such that some but not all of the EcoRI sites present in the plasmid are cleaved. This partial digestion procedure is described in more detail in Maniatis et al., *Molecular Cloning: A Laboratory Manual*, Cold Springs Harbor Laboratories, Cold Spring Harbor, N.Y. (1982). A 1133 bp segment including a nucleotide sequence corresponding to the sequence shown in FIG. 2 from residue 1 to residue 1125 is isolated from the EcoRI partial digestion products by size fractionation.

The prokaryotic expression vector pKK223-3 (Pharmacia Fine Chemicals, Piscataway, N.J.) is linearized by digestion with EcoRI. The digested vector and the 1133 bp pre-huTFh structural gene-containing segment are operatively linked using T4 DNA ligase to form the circular recombinant DNA molecule pKK-pre-huTFh.

*E. coli* RR1 is transformed with pKK-pre-huTFh and ampicillin resistant transformants, i.e., clones containing pKK-pre-huTFh, are selected.

b. Expression of huTFh in *E. coli*

A recombinant DNA molecule capable of expressing the huTF gene in *E. coli* is constructed by manipulating the 1133 bp segment prepared in Example 16a. That segment is first dephosphorylated with alkaline phosphatase and then digested with the restriction endonuclease BbvI. The resulting 964 bp segment includes a nucleotide sequence corresponding to the sequence shown in FIG. 2 from residue 164 to residue 1125 and is isolated by size fractionation.

Synthetic oligonucleotide adaptor segments having the sequences:

5'-AATTGACATGTCAGGCAC-
TACAAATACTGTGGCAGCATATAATT-3',
and

3'-CTGTACAGTCCGTGATGTTTAT-
GACACCGTCGTATATTAAATTG-5', are produced as previously described and annealed to form a double-stranded DNA linker segment containing cohesive EcoRI and BbvI ends according to the methods of Rotherstein et al., *Methods in Enzymol.*, 68:98 (1979). The linker is operatively linked first to the 964 bp segment to form a 1008 bp segment. The 1008 bp segment is then operatively linked to the EcoRI digested vector pKK223-3, using T4 DNA ligase to form the circular recombinant DNA molecule pKK-huTFh.

Recombinant DNA molecule pKK-huTFh differs from pKK-pre-huTFh only in that (1) a segment from residue 1 to residue 129 is omitted, and (2) a new methionine codon is operatively linked before residue 130 such that protein expression (translation) begins at the inserted methionine codon.

The recombinant DNA molecules pKK-pre-huTFh and pKK-huTFh are introduced into a prokaryotic host medium compatible with expression of the huTFh or pre-huTFh protein encoded by the structural gene contained within. Exemplary of host cells containing such medium are *E. coli* strain RR1. The host is transformed with the recombinant DNA molecule, cultured under conditions compatible with cell growth and expression of the recombinant DNA and the expressed protein is harvested by well known techniques.

c. Expression of pre-huTFh in CHO Cells

A recombinant DNA molecule capable of expressing the pre-huTFh gene in vertebrate cells is constructed using the 1133 bp segment prepared in Example 16a.

Synthetic oligonucleotide adapter segments having the sequences:

5'-AATTCCCGGG-3', and

5'-GATCCCCGGG-3', are produced using the methods of Caruthers et al., supra and Gait et al., supra. The oligonucleotide adapter segments are then linked to each terminus of the 1133 bp segment using the methods described by Rotherstein et al., *Methods in Enzymol.*, 68:98 (1979). The EcoRI cohesive termini originally present on the 1133 bp segment are thereby converted to BglII cohesive termini.

The eucaryotic simian virus (SV40) based expression vector, pKSV-10 (Pharmacia Fine Chemicals, Piscataway, N.J.), is linearized by digestion with the restriction endonuclease BglII. The BglII-adapted 1133 bp segment and the BglII-digested vector are operatively linked using T4 DNA ligase to form the circular recombinant DNA molecule pSV-pre-huTFh.

*E. coli* RR1 is transformed with pSV-pre-huTFh and successful transformants are selected on the basis of ampicillin resistance and cloned. The selected transformants are then cloned and screened for the presence of pSV-pre-huTFh by assaying each clone for the presence of expressed pre-huTFh protein using monoclonal antibody TF8-5G9.

d. Expression of huTFh in CHO Cells

Recombinant DNA molecule capable of expressing the huTFh gene in mammalian cells is constructed by digesting pSV-pre-huTFh from Example 16c with the restriction endonuclease BglII. The resulting 1153 bp segment is isolated by size fractionation and subsequently digested with the restriction endonuclease BbvI. The resulting 974 bp segment includes a nucleotide adapter sequence corresponding to the sequence shown in FIG. 2 from residue 164 to residue 1125 and is isolated by size fractionation.

Synthetic oligonucleotide adapter segments having the sequences:

5'-GATCGACATGTCAGGCAC-
TACAAATACTGTGGCAGCATATAATT-3',
and

3'-CTGTACAGTCCGTGATGTTTAT-
GACACCGTCGTATATTAAATTG-5', are produced as previously described and annealed to form a double-stranded DNA linker segment containing cohesive BglII and BbvI cohesive termini. The linker is then operatively linked to the 974 bp segment using T4 DNA ligase to form a 1018 bp segment including a nucleotide sequence corresponding to the sequence shown in FIG. 2 from residue 130 to residue 1125.

The plasmid expression vector pKSV-10 is linearized by digestion with BglII and then operatively linked to the 1018 bp segment using T4 DNA ligase to form the circular recombinant DNA molecule pSV-huTFh.

The recombinant DNA molecules pSV-pre-huTFh and pSV-huTFh are introduced into a eucaryotic host medium compatible with expression of the huTFh or pre-huTFh protein encoded by the structural gene contained within. Exemplary of host cells containing such a medium are CHO cells.

The host is transfected with the recombinant DNA molecule and stable transformants are selected by well known techniques. See for example Graham et al., *Virol.*, 52:456 (1973); and Southern et al., *J. Mol. Appl. Genet.*, 1:327–341 (1982). Transformed host cells are cultured under conditions compatible with cell growth and expression of the recombinant DNA and the expressed protein is harvested by well known techniques.

e. Expression of pre-huTFh in Yeast

A recombinant DNA molecule capable of expressing the pre-huTFh gene in *S. cerevisiae* is constructed by preparing oligonucleotide adapter segments having the sequence:

5'-AATTCCCGGG-3', and

5'-CGCCCGGG-3', and linking them to the termini of the 1133 bp segment of Example 16a as previously described. The adapted segment thus formed has ClaI cohesive termini.

The yeast expression vector, pTDT1 (American Type Tissue Collection #ATCC 31255) is linearized by digestion with the restriction endonuclease ClaI. The above ClaI-adapted 1133 bp segment and the ClaI digested vector are operatively linked using T4 DNA ligase to form the circular recombinant DNA molecule pY-pre-huTFh.

*E. coli* RR1 is transformed with pre-huTFh and transformants expressing the pre-huTFh structural gene are identified and selected as described in Example 16c.

f. Expression of huTFh in Yeast

A recombinant DNA molecule capable of expressing the huTFh structural gene in *S. cerevisiae* is constructed by digesting pY-pre-huTFh with ClaI to produce a 1151 bp segment including a nucleotide sequence corresponding to the sequence shown in FIG. 2 from residue 1 to residue 1125. After isolation by size fractionation, the 1151 bp segment is digested with the BbvI to produce a 978 bp segment including a nucleotide sequence corresponding to the sequence shown in FIG. 2 from residue 164 to residue 1125. The 978 bp segment is then isolated by size fractionation.

Synthetic oligonucleotide adapter segments having the sequences:

5'-CGGACATGTCAGGCAC-
TACAAATACTGTGGCAGCATATAATT-3',
and

3'-CTGTACAGTCCGTGATGTTTAT-
GACACCGTCGTATATTAAATTG-5', are produced and annealed as previously described to form DNA adapter segments having ClaI and BbvI cohesive termini. The adapter segment is first operatively linked to the 978 bp segment to form a 1020 bp segment. The 1020 bp segment is subsequently linked to the ClaI-digested pTDT1 vector, prepared as described in 16e., using T4 DNA ligase to form the circular recombinant DNA molecule pY-huTFh.

The recombinant DNA molecules pY-pre-huTFh and pY-huTFh are introduced into a yeast host medium compatible with expression of the huTFh or pre-huTFh protein encoded by the structural gene contained within. Exemplary of host cells containing such a medium are *S. cerevisiae* cells.

The host is transformed with the recombinant DNA molecule and cultivated in selection medium to isolate successfully transformed cells by well known techniques. See, for example, Hinnen et al., *Proc. Natl. Acad. Sci. USA*, 75:1929 (1978); and Miyajima et al., *Mol. Cell. Biol.*, 4:407 (1984). Transformed cells are cultured under conditions compatible with cell growth and expression of the recombinant DNA, and the expressed protein is harvested by well known techniques.

g. Production of Soluble huTFh by Expression of Recombinant huTFh Coding Sequences The expression of soluble huTFh from recombinant DNA molecules may be accomplished in a variety of expression media in a manner similar to that described in Example 16 for pre-huTFh and huTFh. In that example a 1133 bp pre-huTFh structural gene containing segment having EcoRI cohesive ends is produced in Example 16a and subsequently manipulated in Examples 16b–f resulting in vectors capable of expressing either pre-huTFh or huTFh in three exemplary expression mediums, *E. coli*, *S. cerevisiae*, and CHO cells. Similarly the 805 bp segment containing a soluble pre-huTFh structural gene having EcoRI cohesive ends and prepared in Example 16a is manipulated according to the methods described in Examples 16b–f to produce expression vectors capable of expressing a soluble form of either pre-huTFh or huTFh (i.e., pre-huTFh-TR or huTFh-TR) in those same expression media.

17. Inhibition of Coagulation by Polypeptides p24-35 and p152-169

Polypeptides p24-35 and p152-169, whose amino acid residue sequences are shown in Table 7, were synthesized as described in Example 11.

TABLE 7

| Designation[a] | Amino Acid Residue Sequence |
|---|---|
| p24–35 | H—EWEPKPVNQVYT—OH |
| p152–169 | H—IYTLYYWKSSSSGKKTAK—OH |

[a]The laboratory designation of each polypeptide represents the included amino acid residue sequence as shown in FIG. 1.

Polypeptides p24-35 and p152-169 were then assayed for their ability to competitively inhibit huTF-initiated coagulation as described in Example 12. The results of this study are shown in FIG. 12 and indicate that p24-35 and p152-169 are capable of inhibiting 45% and 25% respectively, of the huTF-initiated coagulation when utilized at 10 uM concentrations. It should be noted that in this study background inhibitions such as for those peptides indicated by a closed circle in FIG. 12 were lower than the study shown in Table 4. As a result, polypeptides producing at least a 20% inhibition of coagulation at a concentration of 10 uM in this study were considered huTF binding site polypeptide analogs.

Thus, polypeptides p24-35 and p152-169 represent huTFh polypeptide binding-site analogs of the present invention. It should also be noted that the results obtained with p24-35, when taken in view of the similar results obtained with polypeptide p25-49, indicate that a huTFh-factor VII/VIIa binding site can be formed by the amino acid residue sequence those two polypeptides have in common, i.e., residues 30–35 as shown in FIG. 1 (-VNQVYT-).

18. Kinetics of Inhibition of Coagulation by Anti-huTF Antibodies

To determine the time in which anti-huTF antibodies were capable of inhibiting huTF-initiated coagulation, the time-course of inhibition was measured using the inhibition assay described in Example 10.

Approximately 1 ng of MAPS-isolated TF8-5G9 monoclonal antibody prepared as described in Example 7 was admixed in 100 ul of HBS/BS with approximately 1 ng of relipidated huTF prepared as described in Example 4. The various admixtures so formed were maintained at 37 degrees C. for varying times from about 1 to about 60 minutes to allow the anti-huTF antibody molecule to immunologically bind the huTF and form an immunoreaction product. At the times specified in FIG. 13 each admixture was subsequently assayed for huTF procoagulant activity as described in Example 2 and the percent inhibition was then expressed as described in Example 10.

FIG. 13 shows the results of such a kinetic measurements which indicates that inhibitions of huTF-initiated coagulation greater than 65 percent occurred in less than 10 minutes at the concentration of antibody and purified huTF utilized in this assay. It is believed that more rapid and complete inhibitions would result from higher concentrations of anti-huTF antibody.

19. Dose-Response of Inhibition of huTF-Initiated Coagulation by Anti-huTF Antibodies The ability of the anti-huTF antibodies of the present invention to inhibit huTF-initiated coagulation over a range of antibody dosages was assayed by the methods described in Example 10 with the following modifications. One ng of relipidated huTF prepared in Example 4 was admixed in 0.1 ml of HBS/BSA with various amounts of TF8-5G9 monoclonal antibody isolated as described in Example 7. The admixtures thus prepared were maintained to form immunoreaction products and were subsequently assayed for huTF procoagulant activity as described in Example 10.

Results of such a dose-response assay are shown in FIG. 14 and indicate that inhibitions are half of maximum at approximately 1 to 5 ng of anti-huTF per ml for the concentration of huTF used in this study.

A similar dose-response was performed using lysed human cells as the source of huTF.

Human fibroblast cell line GM1381 (NIGMS Human Genetic Mutant Cell Repository) was cultured in Dulbecco's Modified Eagle's Medium (DMEM, Gibco Laboratories, Grand Island, N.Y.) supplemented with 2 mM glutamine, 5% fetal calf serum and antibiotics at 37 degrees C. and under 7% (v/v) carbon dioxide in air. GM1381 cells were grown and harvested, and a pellet of $30 \times 10^6$ cells was prepared by centrifugation and frozen at minus 70 degrees C. This frozen pellet was quick thawed by the addition of 9 mls of 15 mM betaoctylglucopyranoside (Sigma) in HN buffer (25 mM Hepes, 140 mM NaCl, pH 7.0) and maintained at 37 degrees C. for 10 minutes to lyse the cells after which time 18 mls of HN was admixed to form a cell lysate.

Monoclonal antibody TF8-5G9 isolated as described in Example 7 was diluted with 0.01% BSA (Sigma, RIA grade) to the various dosages specified in FIG. 15. Twenty-five ul of each antibody dilution was then admixed with 225 ul of the above prepared cell lysate and maintained at 37 degrees C. for 60 minutes to allow the antibody to immunoreact with any huTF present in the cell lysate and form an immunoreaction product. Thereafter 50 ul of a 25 mM $CaCl_2$ solution was admixed with 50 ul of the solution containing the immunoreaction product followed by 50 ul of citrated human plasma to initiate coagulation. The admixtures thus formed were maintained at 37 degrees and the time between the addition of the plasma and the formation of a clot was measured. The effective huTF concentration and percent inhibition was calculated as described in Example 10.

Results from a dose-response inhibition assay using human GM1381 cell lysates as a source of huTF are shown in FIG. 15. Those results indicate that TF8-5G9 anti-huTF antibody produces half maximal inhibition of this cell lysate source of huTF at approximately 8–10 ng antibody per ml.

20. Crossreactivity of MoAbs with Non-Human Tissue Factor

Tissue factor was isolated from either brain tissues (rat, rabbit, bovine, canine, ovine, porcine and baboon) or tissue culture cells [African green monkey kidney (COS) cells]. Tissues or cells were thawed, stripped of membranes, minced, homogenized in 1 ml of cold acetone per g of tissue, and filtered under vacuum through Whatman #1 paper. The solids were resuspended in acetone and filtered five additional times, then air dried overnight and stored at −30° C. The acetone powders, which comprised 16–19% of starting wet weight, were pulverized with a mortar and pestle, resuspend at 5% (w/v) in TBS containing 5 mmol/L EDTA and mixed for 1 hour at ambient temperature. Solids were collected by centrifugation at $10,000 \times g$ for 30 minutes at 20° C., and TF-containing membranes were collected by centrifugation of the supernatant at $100,000 \times g$ for 1 hour. The pellet was resuspended in TBS and stored at −80° C.

Antibody inhibition of animal TF (crude tissue extracts containing TF activity) was determined as follows. Equal volumes of TF (1 mg/ml) and hybridoma supernatant (diluted 1/10 with TBS/BSA) were incubated for 2 hours at 37° C. Remaining TF activity was measured by adding 100 ul of the incubation mixture to 50 ul of human factor VII-deficient plasma and 50 ul of 50 mM $CaCl_2$. After 1 minutes at 37° C., 50 ul of a 1/10 dilution of homologous species serum was added as a source of factor VII, and the time for clot formation was determined in duplicate.

Eighteen of the twenty-four MoAbs inhibited the procoagulant activity of baboon brain TF or African green monkey kidney cell extracts (Table 8). However, none of the MoAbs exhibited cross-reactivity with rat, rabbit, bovine, canine, ovine, or porcine TF, i.e., none inhibited the ability of these TF preparations to accelerate the recalcification time of human factor VII-deficient plasma in the presence of a source of homologous factor VII. None of the antibodies inhibited the procoagulant activity of rabbit TF assayed with normal human plasma.

TABLE 8

| MoAb | Isotype | RIA[1] (cpm) | Dot Blot | Western Blot[2] | | % Inhibition of: | | Inhibition of Animal TF[5] |
|---|---|---|---|---|---|---|---|---|
| | | | | R | NR | Coag.[3] | VII[4] | |
| TF8-5C4 | IgG$_1$,κ | 6242 | + | ± | + | 94 | 57 | — |
| TF8-5C9 | IgG$_1$,κ | 28587 | + | − | + | 99 | 80 | — |
| TF8-11D12 | IgG$_1$,κ | 29453 | + | − | + | 99 | 82 | — |
| TF9-1F1 | IgG$_1$,κ | 25133 | + | + | + | 95 | 83 | M,B |
| TF9-1D5 | IgG$_1$,κ | 3872 | + | + | + | 95 | 76 | M,B |
| TF9-1E7 | IgG$_1$,κ | 28586 | + | + | + | 97 | 90 | M,B |

TABLE 8-continued

| MoAb | Isotype | RIA[1] (cpm) | Dot Blot | Western Blot[2] R | NR | % Inhibition of: Coag.[3] | VII[4] | Inhibition of Animal TF[5] |
|---|---|---|---|---|---|---|---|---|
| TF9-1B8 | IgG$_1$,κ | 28552 | + | + | + | 98 | 83 | M,B |
| TF9-1B9 | IgG$_1$,κ | 28523 | + | + | + | 97 | 84 | M,B |
| TF9-2C4 | IgG$_1$,κ | 24435 | + | + | + | 97 | 78 | M,B |
| TF9-2F6 | IgG$_1$,κ | 27422 | + | + | + | 97 | 79 | M,B |
| TF9-4D11 | IgG$_1$,κ | 25994 | + | + | + | 97 | 81 | M,B |
| TF9-5G4 | IgG$_1$,κ | 24073 | + | + | + | 97 | 83 | M,B |
| TF9-5B7 | IgG$_1$,κ | 26819 | + | + | + | 97 | 74 | M,B |
| TF9-5C7 | IgG$_1$,κ | 24543 | + | + | + | 96 | 72 | M,B |
| TF9-6B4 | IgG$_1$,κ | 17894 | + | + | + | 96 | 98 | M,B |
| TF9-6C4 | IgG$_1$,κ | 74065 | + | + | + | 95 | 78 | M,B |
| TF9-6C9 | IgG$_1$,κ | 8054 | + | + | + | 95 | 47 | — |
| TF9-7E10 | IgG$_1$,κ | 8025 | + | + | + | 97 | 54 | — |
| TF9-8E8 | IgG$_1$,κ | 29152 | + | + | + | 97 | 76 | M,B |
| TF9-9E1 | IgG$_1$,κ | 18169 | + | + | + | 90 | 71 | M,B |
| TF9-9C3 | IgG$_1$,κ | 30222 | + | + | + | 97 | 82 | M,B |
| TF9-9E4 | IgG$_1$,κ | 33728 | + | + | + | 95 | 82 | M,B |
| TF9-10C2 | IgG$_1$,κ | 28692 | + | + | + | 98 | 71 | M,B |
| TF9-10H10 | IgG$_1$,κ | 24585 | + | + | + | 0 | 20 | — |
| FAb100 | IgG$_1$,κ | 1929 | — | — | — | 0 | 0 | — |

[1]Unless otherwise stated, all results were obtained using hybridoma tissue culture supernatants at a 1:10 dilution. Radioimmunoassay results, expressed in counts per minute (CPM), using $^{125}$I-TF labeled using lactoperoxidase.
[2]Western blots performed using either reduced (R) or non-reduced (NR) TF.
[3]Inhibition of coagulation of human plasma induced by purified human brain TF.
[4]Inhibition of Specific $^{125}$I-factor VII/VIIa binding to J82 cells. In some cases (asterisk), culture supernatants at 1:10 dilution did not appreciably inhibit factor VII/VIIa binding, and data are presented for purified IgG at 10 ug/ml.
[5]Inhibition of coagulation of human plasma induced by crude baboon brain extract (B) or lysed COS cells (M). A letter was entered for a species if the MoAb inhibited the procoagulant activity by 60% or more.

The inhibition of procoagulant activity expressed by a variety of human cells and tissues was examined in greater detail using MoAb TF8-5G9. TF8-5G9 neutralized the function of purified, relipidated human TF by greater than 90% at IgG concentrations $\geq 1$ ug/ml (FIG. 16). The ability of this MoAb to inhibit the procoagulant activity of human cell lysates and crude tissue extracts was also demonstrated (Table 9). TF8-5G9 at an IgG concentration of 10 ug/ml quantitatively inhibited $\geq 80\%$ of the procoagulant activity of crude brain and placental acetone powders and of lysed human fibroblasts, bladder carcinoma cells, and endotoxin-stimulated peripheral blood mononuclear cells.

TABLE 9

Inhibition of Procoagulant Activity of Various Cells and Tissues by Monoclonal Antibody TF8-5G9

| Source of TF Activity[2] | TF Activity (* Inhibition)[1] |  |  |
|---|---|---|---|
|  | No antibody | PAb100 | TF8-5G9 |
| Purified human brain TF | 1569 | 1520 (3%) | 245 (84%) |
| Crude brain extract | 2059 | 2059 (0%) | 411 (80%) |
| Crude placental extract | 1287 | 1344 (0%) | 159 (88%) |
| GM1381 fibroblasts (lysed) | 990 | 966 (2%) | 143 (86%) |
| Human monocytes (lysed) | 2893 | 2745 (5%) | 176 (94%) |
| J82 bladder carcinoma cells (lysed) | 882 | 902 (0%) | 93 (89%) |
| Rabbit thromboplastin | 2108 | 2108 (0%) | 2157 (0%) |

[1]Purified human brain TF was reconstituted into lipid vesicles before testing.
[2]The two right-most columns tabulate residual TF activity in milliunits measured after treatment with the purified IgG indicated, and are the mean of two determinations. Samples were incubated with 10 ug/ml IgG for 30 minutes at 37° C. before measuring the remaining TF activity. The values in parentheses are percent inhibition; in each case this is relative to the units of activity for the same sample not treated with antibody.

21. Factor VII Binding Studies

Because binding of factor VII/VIIa to TF is required for assembly of the functional TF:VII/VIIa procoagulant complex, the ability of the MoAbs shown in Table 8 to neutralize TF activity via blocking the binding of factor VII/VIIa to TF was examined.

Human tissue factor-mediated binding of factor VII to the surface of J82 bladder carcinoma cells has been well characterized. Fair et al., *J. Biol. Chem.*, 262:11692 (1987). Accordingly, the effects of the MoAbs on the assembly of the cell-surface huTF:VII/VIIa complex was examined by pre-incubating J82 cells with antibody and then quantitating the specific binding of $^{125}$I-factor VII/VIIa.

J82 cells were cultured to confluence in 12-well culture plates as described by Fair et al., *J. Biol. Chem.*, 262:11692 (1987), washed with buffer A (137 mM NaCl, 4 mM KCl, 11 mmol.L glucose, 5 mM sodium azide, 10 mM HEPES, pH 7.45), and incubated for 2 hr at 37° with 0.7 ml of buffer A containing purified MoAb IgG or a 1/10 dilution of hybridoma culture supernatant. Calcium chloride and $^{125}$I-factor VII/VIIa were added to final concentrations of 5 mM and 1 nM respectively, and incubated with cells for an additional 2 hours at 37° C. Cell monolayers were then washed 5× with cold buffer B (140 mM NaCl, 0.5% BSA, 5 mM Tris-HCl, pH 7.45), lysed in 1 ml of 0.2M NaOH, 1% SDS, 10 mM EDTA, and the lysate counted in a gamma counter. Specific binding was determined by subtracting non-specifically bound radioactivity ($^{125}$I-factor VII/VIIa associated with cells in the presence of a 100-fold molar excess of unlabeled factor VII/VIIa). Percent inhibition of specific binding was determined for J82 cells treated with MoAbs relative to control cells treated with 9 parts buffer A and 1 part culture medium.

When factor VII/VIIa is bound to TF it is not normally internalized, but to eliminate the possibility of TF internalization induced by antibody binding, J82 cells were metabolically poisoned with 5 mM sodium azide. Similar results were obtained whether or not the cells were treated with azide.

The results of this study are presented in Table 8 above. All twenty-three MoAbs that inhibited TF activity also blocked factor VII/VIIa binding. As expected, the MoAb that did not inhibit TF activity, TF9-10H10, did not block factor VII binding.

22. Inhibition of Factor Xa Formation by J82 Cells

Rates of factor Xa formation by the huTF:VII/VIIa complex on J82 cells were quantitated in duplicate using the multiwell culture plate assay described by Fair et al., *J. Biol. Chem.*, 262:11692 (1987) with the following modifications. Cells were cultured in 12-well plates and were preincubated for 2 hours at 37° C. with varying concentrations of purified IgG fraction of MoAbs prior to beginning the assay, as described above for factor VII/VIIa binding to J82 cells. A single concentration of factor VII/VIIa (1 mM) was employed in the assay. At intervals of 5, 10 and 15 minutes after addition of factor X to a final concentration of 50 ug/ml, 50 ul of supernatant was withdrawn and added to 550 ul of 50 mM Tris-HCl, 225 mM NaCl, 50 mM EDTA (pH 8.2). Following addition of chromogenic factor Xa substrate (50 ul of 3.4 mM S-2222 Helena Labs, Beaumont, Tex.), factor Xa activity was quantitated by measuring the rate of increase in absorbance at 405 nm in a Beckman DU-30 spectrophotometer with kinetic analysis module. Background hydrolysis of S-2222 by the supernatant of J82 cells incubated in the absence of factor VII/VIIa was subtracted from each determination. Percent inhibition by antibody treatment was calculated relative to cells which had not been preincubated with antibody.

Inhibition curves for treatment of J82 cells with MoAbs TF9-2C4 and TF9-5B7 indicated that the rate of factor Xa formation was inhibited by antibody concentrations similar to those which inhibited factor VII binding (FIG. 17). The non-inhibitory (non-neutralizing) MoAb TF9-10H10 had little or no effect on procoagulant activity, factor VII/VIIa binding, or the rate of factor Xa generation at IgG concentrations up to 10 ug/ml, nor did the control MoAb PAb100 (not shown).

23. Inhibition of Factor X Activation on J82 Cells by Competitive Binding of huTFh Polypeptides to Factor VII/VIIa As is well known in the art, cellular activation of the coagulation protease cascades is associated with a heterogeneous group of disorders variably referred to as the consumptive thrombohemorrhagic disorders. The coagulation protease cascade is initiated most commonly on cell surfaces by high affinity finding of factor VII/VIIa to its membrane receptor and essential cofactor, tissue factor (TF). The bimolecular procoagulant complex of TF and factor VII/VIIa [TF:VII/VIIa], activates factors X and IX by limited proteolysis which leads ultimately to thrombin formation and fibrin deposition. In addition the role of TF in hemostasis, initiation of the coagulation protease cascade by TF has been implicated in disseminated intravascular coagulation and in thrombogenesis. Niemetz et al., *Blood*, 42:47 (1973) and Bevilacqua et al., *J. Exp. Med.*, 160:618 (1984). TF is an important effector molecule expressed on the surface of monocytes and endothelial cells in response to inflammatory mediators and in cellular immune responses.

The ability of the huTFh polypeptides of the present invention to bind to factor VII/VIIa and thereby inhibit the formation of a TF:VII/VIIa complex capable of activating factor X was studied.

Fifty microliters (ul) of a solution containing a huTF polypeptide analog at 100 uM solution containing a huTF polypeptide analog to 100 uM in TBS was added to each well of a 96-well of a 96-well flat bottom polystyrene assay plate. Then to each well was admixed 25 ul of a solution containing factor VII/VIIa isolated as described in Example 3 at a concentration of 1 nm in TBS, further admixed with 25 ul of 20 mM calcium chloride in TBS and the resulting admixture is maintained at room temperature for 30 minutes.

Human bladder cell carcinoma J82 cells were obtained from the American Type Culture Collection (ATCC HTB 1; Rockville, Md.) and cultured as described by Fair et al., *J. Biol. Chem.*, 262:11692–11698 (1987) which methods are incorporated herein by reference.

$5 \times 10^4$ J82 cells are suspended into 50 ul of TBS and admixed to each well of the polystyrene assay plate after the above maintenance period. Immediately thereafter 25 ul of factor X, isolated as described by Fair et al., *J. Biol. Chem.*, 262:11692–11698 (1987), at a concentration of 100 nM in TBS and 50 ul of Xa chromogenic substrate S-2222 (1 mg/ml in TBS) were admixed, and the resulting admixture was maintained for two minutes at room temperature to form a chromogenic reaction product containing solution.

The amount of chromogenic product formed was quantitated by measuring the amount of optical density (O.D.) at 405 nanometers (nm) using a V-max 96 well spectrophotometer (Molecular Devices, Mountain View, Calif.). Controls with PBS in place of polypeptide or with no factor VII added were also run to establish the maximum and minimum possible O.D. values. Results of these measured inhibitions are shown in Table 10.

TABLE 10

| Inhibition of X Activation on J82 Cells Using huTF Polypeptides | |
|---|---|
| huTFh Polypeptide | Optical Density[1] |
| PBS | 0.960 ± 0.083 |
| No factor VII/VIIA | 0.005 ± 0.001 |
| p1–18 | 1.007 ± 0.087 |
| p1–30 | 1.098 ± 0.028 |
| p11–28 | 0.687 ± 0.071 |
| p24–35 | 0.477 ± 0.017 |
| p26–49 | 0.437 ± 0.020 |
| p40–71 | 0.814 ± 0.053 |
| p72–104 | 0.781 ± 0.047 |
| p94–123 | 0.818 ± 0.055 |
| p121–155 | 0.889 ± 0.067 |
| p144–159 | 0.507 ± 0.053 |
| p146–167 | 0.004 ± 0.001 |
| p157–169 | 0.389 ± 0.035 |
| p161–190 | 0.600 ± 0.023 |
| p190–209 | 0.625 ± 0.031 |
| p204–226 | 0.715 ± 0.042 |
| p244–263 | 0.619 ± 0.047 |

[1]Inhibition of factor X activation (Xa formation) was considered significant if the optical density (O.D.) was about 0.500 or less.

The results of this study indicate that huTFh polypeptides p24-35, p26-49, p144-159, p146-167 and p157-169 bind to factor VII/VIIa and inhibit its ability to form a TF:VII/VIIa complex that can activate factor X. These results indicate that a huTFh binding site polypeptide analog of the present invention can be used to inhibit coagulation.

24. In Vivo Inhibition of Coagulation by Anti-huTFh MoAbs

Sepsis due to gram-negative bacteria often involves a shock state that can ultimately lead to death. Disturbances of the hemostatic system are closely linked to the development of the shock state. Taylor et al., *J. Clin. Invest.*, 79:918–825 (1987) have shown that exogenously added activated protein C, a naturally occurring anticoagulant enzyme, prevents the coagulopathic response and lethal effects of LD$_{100}$ concentrations of *E. coli* in baboons.

The ability of an anti-coagulant MoAb of the present invention to inhibit coagulation in vivo was examined using the baboon model of septic shock described by Taylor et al., Supra. Baboons weighing 7–8 were fasted overnight before study and immobilized the morning of the experiment with ketamine (14 mg/kg, intramuscularly). Sodium pentobarbital was then administered in the cephalic vein through a percutaneous catheter to maintain a light level of surgical anesthesia (2 mg/kg about every 45 min). A femoral vein was exposed aseptically and cannulated in one hind limb for sampling blood. The percutaneous catheter was used to infuse the *E. coli* and other agents, including MoAb TF9-5B7, which was shown in Example 20 to crossreact with baboon TF. After an equilibration period of 30 min., animals were infused over a period of about 10 min. with either 500 ug/kg or 150 ug/kg of MoAb TF9-5B7 (MAPS isolated as in Example 7 and then dialyzed against sterile normal saline to a concentration of 0.58 ug/ml) or 500 ug/kg of an irrelevant MoAb.

After MoAb administration and an equilibration period of 30 min., each animal received LD$_{100}$ dose of *E. coli* (about $10^{10}$ organisms, an amount to produce death due to septic shock at about 8–16 hours post-infusion). The *E. coli* were administered by infusion over a 2 hour period. The results of this study are shown in Table 11.

TABLE 11

In vivo Arrest of Lethality of Septic Shock in Baboon

| Group | MoAb | Dose ug/kg | Hemo-stasis[1] | *E. coli* Infused | Death |
|---|---|---|---|---|---|
| I. Control | TF9-5B7 | 500 | Normal | No | No |
| II. Control | HB[2] | 500 | Normal | Yes | Yes |
| III. Study | TF9-5B7 | 500 | Normal | Yes | No |
|  | TF9-5B7 | 150 | Normal | Yes | No |

[1]Various hemostatic parameters, including blood pressure, activation of coagulation and fibrin degradation products, were determined after MoAb administration, but before *E. coli* infusion.
[2]HB is a MoAb of the same class and subclass as TF9-5B7 but immunoreacts with an irrelevant antigen.

As can be seen from Table 11, baboons receiving MoAb TF9-5B7 survived challenge with an LD$_{100}$ dose of *E. coli*. Both the 150 ug/kg and 500 ug/kg doses of MoAb protected. In addition, the profound hypotension, coagulation cascade activation and degradation of fibrin associated with coagulopathy were markedly attenuated in the animals receiving MoAb TF9-5B7.

25. Characterization of the Light Chain of the 58 kDa huTF Heterodimer as Hemoglobin Alpha Chain Immunoaffinity isolated huTF was further characterized by Western blot analysis to identify the component species of the 58 kDa huTF heterodimer, namely the 47 kDa and 12.5 kDa proteins described in Example 4.

Western blot analysis, conducted as described in Example 6c, was performed using immunoaffinity isolated huTF prepared as described in Example 9, purified human hemoglobin, or molecular weight standards as the samples that were electrophoresed. Where indicated, 50 mM dithiolthreitol was included in the sample buffer for reduction of the disulfide bonds. Western blots were immunoreacted as indicated using non-immune rabbit IgG, rabbit anti-huTF IgG prepared using methods well known or rabbit anti-human hemoglobin IgG obtained from Dako (Santa Barbara, Calif.).

The first two IgG preparations were MAPS-II isolated as described in Example 7.

Results from the above Western blot analysis are shown in FIG. 18. Anti-huTF IgG immunoreacted only the 47 kDa band of reduced huTF, and not the 12.5 kDa band (Panel A, lane 3), whereas the same IgG immunoreacted both the 58 kDa and 47 kDa forms of non-reduced huTF (Panel A, lane 4). These results are consistent with an identification of huTF as the 47 kDa component of the 58 kDa heterodimer. Anti-hemoglobin IgG immunoreacted on Western blots only with the 58 kDa band in the non-reduced huTF sample and not with the 47 kDa monomer (panel B, lane 4). However anti-hemoglobin IgG immunoreacted with the 12.5 kDa band in the reduced huTF sample (Panel B, lane 3) and immunoreacted with the 12.5 kDa purified human hemoglobin protein (Panel B, lane 2). There was no reactivity with a non-immune rabbit IgG.

The above results support the conclusion that the 58 kDa form of non-reduced huTF consists of the 47 kDa huTF protein disulfide-linked to hemoglobin.

Thus, it is now believed that the 12.5 kDa light chain component of the 58 kDa heterodimer described in Example 4 is the alpha chain of hemoglobin, and that its association with the 47 kDa huTF protein is an artifact of the huTFh isolation procedure.

26. Simulated Extracorporeal Circulation a. Antibodies

Murine monoclonal antibodies TF8-5G9, TF9-6B4 and TF9-9C3 to human TF (Morrissey, et al., *Thromb. Res.* 52:247, 1988; Ruf, et al. *Biochem J.* 278:729, 1991) and LM2 directed against the leukocyte integrin Mac-1 were prepared by ascites growth of the hybridomas and isolation of the IgG1 antibody using immobilized protein A as previously described (Ruf, supra). Unrelated mouse IgG and FITC labeled sheep anti-mouse IgG was purchased from Sigma, St. Louis, Mo.

b. Simulated Extracorporeal Circuit (SECC)

This model system provides defined and appropriate flow geometry and hemodynamic stresses, proper surface area to blood volume ratios, and ready access to serial blood samples during a single trial. The system has recently been modified to decrease the volume, surface area and flow. Each perfusion circuit has a surface area of 0.4 m$^2$ and is assembled from silastic tubing (Avecor, Inc., Plymouth, Minn.) polycarbonate connectors, a polyvinyl chloride venous reservoir bag (Gish Biomedical, Santa Ana, Calif.) and a 0.4 m$^2$ spiral-coil membrane oxygenator (model 0400-2A, Sci-Med Life Systems, Inc., Minneapolis, Minn.). All components of the circuit were sterilized and blood samples were only exposed to sterile labware throughout cell separation. Three hundred ml of human blood was drawn from healthy male donors (age 24–34) through a 16 G 1.5 in. needle and polyvinyl tubing directly into a venous reservoir bag containing beef lung heparin, 5 units/ml blood (The Upjohn Co., Kalamazoo, Mich.), and dextrose, 2.25 mg/ml blood. Informed written consent was obtained from all donors according to the provisions of the Declaration of Helsinki, and the protocols for the study were approved by the Institutional Review Board of the University of Pennsylvania. Six SECCs were run at 37° C. All donors abstained from all medications for at least two weeks prior to giving blood.

Blood and gas compartments of the circuits were flushed with 100% carbon dioxide for 15 minutes before priming and then were evacuated by applying suction to the sample port. The perfusion circuit was then filled with blood, avoiding bubble formation. Blood was recirculated for 6 hours at 0.3 l/min at 37° C. by a calibrated, barely occlusive roller pump (Sarns, Ann Arbor, Mich.). The oxygenator was ventilated with a mixture of 95% oxygen and 5% carbon dioxide flowing at 0.7 liters/min. The zero an standing (uncirculated) control samples were obtained from the venous reservoir before connection to the circuit. The standing control sample was incubated in the water bath for 6 hours before it was processed. Experimental samples were taken at 2, 4, and 6 hours of recirculation. The blood was drained from the system and replaced with 150 ml of wash solution containing 0.01M EDTA. The wash solution was recirculated for 15 minutes. All blood and wash samples were collected into citric acid-sodium citrate-dextrose (ACD, 9:1 vol/vol).

c. Leukocyte Separation

At each time point, samples were removed for leukocyte count and differential staining. Whole blood was layered onto Ficoll Hypaque (Sigma) and centrifuged at 400 g for 30 min at room temperature. For MAC-1 studies, to avoid upregulation by temperature, cell separation was carried out at 4° C. Mononuclear cells were harvested from the interphase and washed twice in Hanks Balanced Salt Solution (Gibco) without $Ca++$ and $Mg++$. Cell count was adjusted at $0.5 \times 10^7$/ml for flow cytometry analysis and at $1 \times 10^8$/ml for assay of PCA of intact viable cells. Viability was typically greater than 95% as checked by trypan blue exclusion test.

During the 6 hour SECC, leukocyte counts gradually decreased, declining to 57% of initial value by 6 hours, which correlated with the attachment of cells to the large surface area of the membrane oxygenator. Compared to lymphocytes, monocytes and neutrophils, presumably because of different adhesive receptors on their surfaces, and perhaps greater density once activated, are predisposed to adhere to artificial surfaces. Based on differential counts obtained at progressive time points, the number of monocytes and neutrophils progressively decreased relative to lymphocytes in the circulating blood over the 6 hours (FIG. 19). The decrease in circulating monocytes was concordant with the number of monocytes subsequently recovered. This decrease was primarily due to the attachment of neutrophils and monocytes to the surface. The washing procedure typically eluted more than 90% of attached cells from the surfaces. Lymphocyte count was minimally affected by recirculation.

d. Cell Staining for Flow Cytometry

Isolated mononuclear cells ($5 \times 10^6$) were fixed overnight in 1% paraformaldehyde in HBSS and washed twice in HBSS with 0.1% azide. The cells were resuspended in 100 µl of primary antibody at 10 µg/ml final concentration. Cells were either incubated with equal concentrations of the three TF monoclonals—TF8-5G9, TF9-6B4, and TF9-9C3—or with TF9-9C3 alone. For negative controls, the same concentration of nonimmune mouse IgG was used. Incubations were carried out for 45 minutes at 4° C. After centrifugation, supernatant was removed and cells were washed once more in HBSS 0.1% azide. Secondary antibody (sheep antimouse IgG FITC [Sigma]) was diluted in HBSS 1% serum and cells were incubated for 30 min at 4° C. Cells were washed twice and stored in the dark until analysis. Fluorescence was analyzed by a Coulter Epics Elite Flow Cytometer. The fluorescence of lymphocytes and monocytes was analyzed by gating on each respective cell population based on their different forward and side scatters. Log fluorescence values were converted to linear units and a 0 time sample was arbitrarily assigned a value of 100. Mean fluorescence of samples was compared to that of the 0 time sample and the standing control sample that was not recirculated but was incubated at 37° C. for 6 hours in a silastic tube.

Fluorescence reporting by flow cytometry of TF on the surface of circulating monocytes stained with Mabs against TF increased significantly by 6 hours ($p<0.05$) and in cells subsequently recovered from the circuit ($p<0.05$), but remained at baseline levels in the standing controls (FIG. 20). Lymphocytes did not display TF by flow cytometry. Cell preparations incubated with non-specific mouse IgG did not show any increase of TF by surface fluorescence, providing evidence that the observed increase after reaction with TF Mabs was not attributable to Fc receptor upregulation. The increase in fluorescence is due to a relatively small percentage of monocytes, while the majority of the cells show very little change in their staining pattern. This results in a skewing or tail formation on the flow cytometry staining pattern by 6 hours compared to 0 min sample or standing control (FIG. 21). Monocytes expressing TF on their surfaces appear as soon as 2 hours ($p<0.05$) and the percentage of positive cells increase up to 6 hours ($p<0.01$), the highest proportion being in the cells recovered from the surface of the circuit (FIG. 22).

e. Procoagulation Activity Assay (PCA).

Viable cell PCA of the preparations was determined by a one-step recalcification time as described previously (Conkling, et al., *Blood*, 72:128, 1988). Whole cell suspension (0.01 ml) was incubated with pooled normal human plasma or factor deficient plasma (0.01 ml) for 60 seconds. After addition of 0.1 ml 25 mmol/L $CaCl_2$, the clotting times were measured by a Fibrometer (BBL Fibrosystems, Baltimore, Md.). Each sample was run in duplicate. To quantitate PCA, recombinant human TF (Corvas, La Jolla, Calif.) was used and a standard curve was obtained from serial dilutions. PCA values of cell suspensions or cell lysates were derived from the standard curve and expressed as pg TF.

During SECC, there is a preferential adherence of monocytes and neutrophils to the oxygenator interface. Based on the differential counts obtained for each sample, PCA values were normalized for $10^6$ monocytes. PCA analysis was also carried out on lysed cells. For this purpose, mononuclear cells were lysed by resuspending them in 15 mM octyl-β-D-glycopyranoside (Sigma, St. Louis, Mo.) in 25 mM Hepes-saline (pH 7.4). Cells were thoroughly vortexed and incubated for 15 min at 37° C. Lysates were diluted threefold with Hepes saline, vortexed, and placed on ice. PCA was assayed within 10 minutes.

The cells with TF antigen also had functional TF by procoagulant assay (FIG. 23). By 4 hours, mononuclear cell suspension significantly shortened the clotting time of normal plasma ($p<0.05$). Mononuclear cell PCA increased over baseline more than 15-fold ($p<0.05$) by 6 hours and 25-fold in the recovered cells (p<0.01). The activity was factor X dependent, i.e., acceleration of clotting did not occur in factor X deficient plasma. In contrast, there was a variable factor VII dependence since the clotting times using factor VII (FVII) deficient plasma was either prolonged, as would be the case for free TF lacking bound factor VIIa, or similar to normal plasma, consistent with the presence of TF-VIIa complex on cells. However, when mononuclear cells were incubated with 10 mmol/L EDTA for 30 minutes at 37° C. to dissociate FVII/VIIa from tissue factor and added to FVII deficient plasma, prolonged clotting times resulted, as compared to normal plasma. Mononuclear cells incubated with factor XI (FXI) or FIX deficient plasmas gave similar values to normal plasma.

To establish whether the observed PCA is exclusively due to TF, mononuclear cells were incubated for 15 minutes on ice with 25 μg/ml of the TF monoclonal antibody cocktail or mouse IgG as a control. PCA of mononuclear cells was abolished by the TF antibodies, confirming that other procoagulants do not contribute to the observed PCA activity (Table 12).

TABLE 12

Mononuclear Cell Generate PCA After Neutralization by TF Monoclonal Antibodies

|  | Clotting Time (sec) | PCA pg TF/$10^6$ Monocytes | % Inhibition Compared to No Antibody |
|---|---|---|---|
| No Antibody | 25.5 | 1768 | — |
| Mouse IgG | 26.6 | 1664 | 6 |
| TF Monoclonals | 128.5 | 8 | 99.6 |

Mononuclear cells, eluted from the oxygenator surface, were incubated with the TF MAb cocktail (25 μg/ml each) or the same amount of non-immune mouse IgG for 15 minutes on ice. Clotting times were determined by recalcification and PCA derived from standard curves compared to recombinant TF. After blocking with neutralizing TF MAbs, PCA was totally inhibited.

When TF immunoreactive protein and TF functional PCA were compared to a maximal stimulation (10 μg/ml LPS for 6 hours), TF antigen on monocytes from the circuit by 6 hours reached the level of expression of TF on LPS-stimulated cells. However, TF activity of intact monocytes peaked in the recovered cells at only 49% of the LPS-stimulated ones (FIG. 24). Although all TF is on the cell surface, there is a significant different in PCA activity of intact and lysed cells. Mononuclear cell PCA from the same experiment were measured on intact and lysed cells and data were compared to LPS stimulated samples. After lysis, mononuclear cell PCA reached the level of LPS stimulated cells by 6 hours and in the recovered cells similarly to the flow cytometry data (Table 13).

TABLE 13

Mononuclear Cell Generated PCA of Intact and Lysed Cells

|  | Intact | | Lysed | |
|---|---|---|---|---|
| HOUR | A | B | A | B |
| 0 | 13 | 0.2 | 11 | 0.1 |
| 2 | 157 | 2.9 | 414 | 3.1 |
| 4 | 511 | 9.6 | 7300 | 54 |
| 6 | 800 | 15 | 10800 | 81 |
| GR | 2200 | 42 | 12590 | 95 |
| LPS | 5330 | 100 | 13300 | 100 |

Mononuclear cells from the same experiment were either lysed or kept intact and analyzed simultaneously for PCA. Results are expressed as pg TF/$10^6$ monocytes (A) and as percentage of LPS stimulated samples (B).

The occupancy of the integrin Mac-1 by different ligands in the process of adherence augments the TF response (Fan, et al., *J. Clin. Invest.*, 87:50, 1991). Since it has been shown that neutrophils can upregulate Mac-1 during a two hour SECC, monocyte Mac-1 surface expression during the six-hour SECC (FIG. 25) was investigated by flow cytometry. The number of Mac-1 receptors on monocytes increased up to 4 hours, then leveled off. By far, the most Mac-1 was detected in adhered cells. Monocytes from the standing control sample at 6 hours expressed Mac-1 in the same range as monocytes from the circuit by 2 hours.

f. Endotoxin Measurement

Plasma samples were recovered at each time point and kept frozen until endotoxin was measured by a method using the Limulus Amebocyte Lysate chromogenic assay (Whittaker, Walkersville, Md.). Endotoxin concentration remained below the detection limit of 0.01 U/ml throughout the SECCs.

Endotoxin was below the detection level in this highly sensitive assay. Since complement activation has been detected during CPB, it is reasonable to suggest that complement activation fragments such as C5a may be causative. Whether the mechanisms operate directly on monocyte or indirectly through lymphocyte activation is not known at this time.

g. Statistical Analyses

Results are expressed as mean±SEM. Comparisons between values within each run were made using paired t tests compared to initial values. A value of $p<0.05$ was considered statistically significant.

SUMMARY AND DISCUSSION OF THE RESULTS OF EXAMPLES 1–26

A library of twenty-four MoAbs to human brain TF, obtained from 2 different cell-fusions, has been described. The immuno specificity of each MoAb was characterized by dot blot, Western blot and radioimmunoassay. Most MoAbs reacted with human TF under all three conditions, and with both native and denatured TF. One of the MoAbs, TF8-5G9, has been used successfully for routine purification of the TF protein. It quantitatively adsorbs TF activity from tissue extracts and consistently yields purified human TF in milligram quantities.

All but one of the MoAbs strongly neutralized the functional activity of purified human brain TF. Although several MoAbs were found to crossreact with TF from baboon and monkey, none of the antibodies inhibited the coagulation of factor VII-deficient human plasma initiated by rat, rabbit, bovine, canine, ovine, or porcine thromboplastin in the presence of homologous factor VII. Furthermore, the initiation of coagulation of normal human plasma by rabbit brain thromboplastin was not inhibited by any of these MoAbs, which supports the conclusion that the inhibition of human TF procoagulant activity was not due to interference by the antibodies with soluble plasma coagulation proteins, including factor VII/VIIa.

The most straightforward basis for the inhibition of TF procoagulant activity by anti-TF antibodies is blocking of factor VII/VIIa binding. As expected, all twenty-three anticoagulant (neutralizing) MoAbs abolished the specific binding of factor VII/VIIa to J82 cells, consistent with the primary receptor function of TF. This was further substantiated in dose titration of selected purified MoAbs in which half-maximal inhibition of factor VII binding and half-maximal inhibition of the rate of factor Xa formation occurred at similar IgG concentrations.

A MoAb to human TF has recently been described by Carson et al., *Blood*, 70:490 (1987) as inhibiting TF activity, apparently by interfering with factor VII/VIIa binding, although this was not examined directly. The finding that twenty-three out of twenty-four of the presently described MoAbs strongly neutralized TF activity is remarkable. Experience in applicants laboratory with MoAbs to a variety of human coagulation proteins has been that only a minor proportion neutralize functional activity. It is unlikely that the hybridomas are all sibling clones, because of the differences in their reactivities, including cross-reactivities with primate TF. In addition, ongoing epitope mapping studies indicate that at least three distinct, noncompeting antibody binding sites are recognized by this panel of MoAbs. Therefore, the large proportion of neutralizing MoAbs to TF is unlikely the consequence of a few immunodominant epitopes with also participate in function; indeed, the TF amino acid sequence is predicted by the method of Hopp et all., *Mol. Immunol.*, 20:483 (1983) to contain multiple antigenic determinants.

The small size of TF may explain in part why so many anti-TF MoAbs blocked factor VII/VIIa binding. TF is predicted from cDNa cloning to have a 25 kDa extracellular domain, excluding glycosylation. Therefore, antibody and factor VII/VIIa molecules may exhibit steric hindrance in binding to the much smaller extracellular domain of TF. The steric hindrance hypothesis is consistent with the observation that concanavalin A inhibits TF activity, [Pitlick, *J. Clin. Invest.*, 55:175 (1975)] since the carbohydrate groups on TF are probably not required for function [Nakamura, *Throm. Hemost.*, 58:135 (1987)].

It was of some concern that the factor VII-dependent procoagulant activity expressed by different cells and tissues might be attributable to more than one molecular species of TF-like proteins with similar function. However, the MoAb TFS-5G9 quantitatively inhibited the procoagulant activity of crude brain and placental extracts, and of lysed fibroblasts, bladder carcinoma cells and peripheral blood mononuclear cells. While not exhaustive, these results support the conclusion that cellular procoagulant activities currently attributed to TF are antigenically related if not identical. This is consistent with the finding that there is probably a single gene for TF.

Recently, it has been demonstrated that the lethal effects of septic shock can be prevented in baboons by infusion of activated protein C, an anticoagulant protein which acts at intermediate stages in the coagulation protease cascade. The present studies indicate that MoAbs which inhibit TF activity are highly specific in vivo anticoagulant agents since, by blocking the initiation of the coagulation protease cascade, they prevent the consumption of plasma coagulation factors normally associated with pathologic activation of intravascular coagulation.

The 58 kDa form of huTF described in Example 4 was shown here to be a disulfide-linked heterodimer of the 47 kDa TF protein and an approximately 12.5 kDa polypeptide, now identified immunochemically and by partial amino acid sequence as the alpha chain of hemoglobin. Previous speculation that the 58 kDa band might constitute a naturally occurring, heterodimeric form of cellular TF is probably incorrect, as it is likely that the 58 kDa heterodimer is formed during isolation.

The alpha chain of hemoglobin has a single cysteine and TF is predicted from the cDNA to have a single cysteine in its cytoplasmic domain. TF also has four cysteines in its extracellular domain, but at least two must be involved in intrachain disulfide binds since TF function is lost following reduction. The single cysteine in the cytoplasmic domain of TF is probably, like cysteines in most cytosolic proteins, maintained in the reduced state. This (or less likely, another cysteine of TF) may be readily accessible for mixed disulfide formation following cell lysis, and it is proposed that oxidation during the isolation procedure results in the formation of a disulfide bond between the cysteine residue of the cytoplasmic domain of TF and hemoglobin. In support of this conclusion is the observation that heterodimer formation is apparently time dependent, in that minimizing the time between detergent extraction of TF from brain acetone powder and binding to the immunoaffinity matrix diminishes the amount of heterodimeric TF obtained. The presumed 96 kDa TF dimer may also form by a similar mechanism during isolation.

An anti-hemoglobin antibody column specifically bound thee 58 kDa heterodimer, but did not quantitatively remove all of the higher molecular weight species observed in the immunoaffinity-purified TF preparations. Trace amounts of other minor bands with molecular weights in excess of 47 kDa were observed with react with anti-TF antibodies. These minor species, including a portion of the 58 kDa band, may represent mixed disulfides formed between TF and other unidentified proteins.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A method of inhibiting coagulation in an extracorporeal circulation procedure used on a subject extracorporeally, comprising (1) removing blood from a subject and (2) administering to the blood a therapeutically effective amount of a monoclonal antibody which inhibits binding of tissue factor to factor VII/VIIa so that the activity of tissue factor is neutralized in the vasculature.

2. The method of claim 1, wherein the extracorporeal circulation procedure is a cardiopulmonary bypass procedure.

3. The method of claim 1, wherein the subject is a mammal.

4. The method of claim 1, wherein the subject is a primate.

5. The method of claim 3, wherein, the mammal is a human.

6. The method of claim 1, wherein the monoclonal has the specificity of a monoclonal selected from the group consisting of monoclonal antibodies produced by hybridoma cell lines TF8-5G9, and TF9-6B4.

7. The method of claim 6, wherein the monoclonal antibody is selected from the group consisting of monoclonal antibodies produced by hybridoma cell lines TF8-5G9, and TF9-6B4.

8. The method of claim 1, wherein the administration of the monoclonal antibodies is intravenous.

9. The method of claim 1 wherein said monoclonal antibody is administered to a particular patient only once.

* * * * *